(12) United States Patent
Cunningham et al.

(10) Patent No.: US 6,837,858 B2
(45) Date of Patent: Jan. 4, 2005

(54) METHOD AND APPARATUS FOR OBTAINING BLOOD FOR DIAGNOSTIC TESTS

(75) Inventors: David D. Cunningham, Lake Villa, IL (US); Timothy P. Henning, Vernon Hills, IL (US); Eric B. Shain, Glencoe, IL (US); Douglas F. Young, Grayslake, IL (US); Andrew J. Muetterties, Mundelein, IL (US); Thomas G. Schapira, Bristol, WI (US); Geoffrey R. Chambers, Middlesex (GB); Graham J. Hughes, Oxford (GB); Jared L. Watkin, Oxon (GB); Gary F. Prokop, Wheaton, IL (US); Joshua P. Goldfarb, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 239 days.

(21) Appl. No.: 09/972,444

(22) Filed: Oct. 5, 2001

(65) Prior Publication Data

US 2002/0169393 A1 Nov. 14, 2002

Related U.S. Application Data

(63) Continuation of application No. 09/612,722, filed on Jul. 10, 2000, now Pat. No. 6,306,104, which is a division of application No. 08/982,721, filed on Dec. 2, 1997, now Pat. No. 6,093,156, which is a continuation-in-part of application No. 08/759,698, filed on Dec. 6, 1996, now Pat. No. 6,063,039.

(60) Provisional application No. 60/036,395, filed on Jan. 24, 1997.

(51) Int. Cl.[7] ................................................. A61B 5/00
(52) U.S. Cl. ............................................................ 600/573
(58) Field of Search ................................... 600/573, 576, 600/577, 578, 583

(56) References Cited

U.S. PATENT DOCUMENTS 1,934,046 A   11/1933   Demarchi (List continued on next page.)

FOREIGN PATENT DOCUMENTS

AU        3056684        7/1984

(List continued on next page.)

OTHER PUBLICATIONS

Cass et al., "Ferrocene–Mediated Enzyme Electrode for Amperometric Determination of Glucose", *Anal. Chem.*, vol. 56, 1984, pp. 667–671.

(List continued on next page.)

*Primary Examiner*—Eric F. Winakur
(74) *Attorney, Agent, or Firm*—David L. Weinstein

(57) ABSTRACT

Method and apparatus for obtaining a sample of blood from a patient for subsequent diagnostic tests, e.g., glucose monitoring. In one aspect of the invention, the method comprises the steps of:
 (a) placing a blood collection device over a region on the surface of the skin from which said sample is to be obtained,
 (b) forming a seal between said blood collection device and said surface of the skin,
 (c) creating a vacuum sufficient to result in said surface of the skin becoming stretched and engorged with blood,
 (d) triggering a lancing assembly and causing a lancet to penetrate said skin,
 (e) retracting said lancet,
 (f) withdrawing blood toward and onto a fluid collector, and
 (g) releasing the vacuum.

In another aspect of the invention, an apparatus for carrying out the method described previously is provided. The apparatus comprises:
 (a) a housing having a sealable chamber located therein and a sealable opening in fluid communication with said sealable chamber,
 (b) a power source,
 (c) a vacuum pump operably connected to said power source, said vacuum pump in communication with said sealable chamber,
 (d) a lancing assembly positioned within said housing, said lancing assembly capable of moving a lancet towards said sealable opening, and
 (e) a fluid collector positioned in said sealable chamber, said fluid collector in fluid communication with said sealable opening.

29 Claims, 27 Drawing Sheets

U.S. PATENT DOCUMENTS

| | | | |
|---|---|---|---|
| 3,933,439 | A | 1/1976 | McDonald |
| 4,151,832 | A | 5/1979 | Hamer |
| 4,203,446 | A | 5/1980 | Hofert et al. |
| 4,360,016 | A | 11/1982 | Sarrine |
| 4,545,382 | A | 10/1985 | Higgins et al. |
| 4,627,445 | A | 12/1986 | Garcia et al. |
| 4,637,403 | A | 1/1987 | Garcia et al. |
| 4,640,297 | A | 2/1987 | Bates |
| 4,653,513 | A | 3/1987 | Dombrowski |
| 4,711,245 | A | 12/1987 | Higgins et al. |
| 4,775,361 | A | 10/1988 | Jacques et al. |
| RE32,922 | E | 5/1989 | Levin et al. |
| 4,838,855 | A | 6/1989 | Lynn |
| 4,844,098 | A | 7/1989 | Mitchen |
| 4,883,068 | A | 11/1989 | Dechow |
| 4,895,147 | A | 1/1990 | Bodicky et al. |
| 4,929,545 | A | 5/1990 | Freitag |
| 4,935,346 | A | 6/1990 | Phillips et al. |
| 4,981,473 | A | 1/1991 | Rosenblatt |
| 4,990,154 | A | 2/1991 | Brown et al. |
| 5,014,718 | A | 5/1991 | Mitchen |
| 5,037,431 | A | 8/1991 | Summers et al. |
| 5,054,499 | A | 10/1991 | Swierczek |
| 5,070,886 | A | 12/1991 | Mitchen et al. |
| 5,161,532 | A | 11/1992 | Joseph |
| 5,165,418 | A | 11/1992 | Tankovich |
| 5,201,324 | A | 4/1993 | Swierczek |
| 5,231,993 | A | 8/1993 | Haber et al. |
| 5,238,655 | A | 8/1993 | Laible et al. |
| 5,279,294 | A | 1/1994 | Anderson et al. |
| 5,320,607 | A | 6/1994 | Ishibashi |
| 5,368,047 | A | 11/1994 | Suzuki et al. |
| 5,374,556 | A | 12/1994 | Bennett et al. |
| 5,487,748 | A | 1/1996 | Marshall et al. |
| 5,509,410 | A | 4/1996 | Hill et al. |
| 5,554,153 | A | 9/1996 | Costello et al. |
| 5,569,223 | A | 10/1996 | Wandell et al. |
| 5,628,890 | A | 5/1997 | Carter et al. |
| 5,636,640 | A | 6/1997 | Staehlin |
| 5,662,127 | A | 9/1997 | DeVaughn |
| 5,680,872 | A | 10/1997 | Sesekura et al. |
| 5,682,884 | A | 11/1997 | Hill et al. |
| 5,951,493 | A | * 9/1999 | Douglas et al. .............. 600/583 |
| 6,093,156 | A | * 7/2000 | Cunningham et al. ...... 600/573 |

FOREIGN PATENT DOCUMENTS

| | | |
|---|---|---|
| DD | 0242962 | 11/1985 |
| DE | 2803345 | 6/1979 |
| DE | 3708031 | 11/1987 |
| DE | 3806574 | 2/1988 |
| EP | 0021798 | 1/1981 |
| EP | 0127958 | 12/1984 |
| EP | 0212906 | 3/1987 |
| EP | 0230472 | 8/1987 |
| EP | 0254203 | 1/1988 |
| EP | 0351892 | 1/1990 |
| EP | 0371503 | 6/1990 |
| EP | 0453283 | 4/1991 |
| EP | 0449525 | 10/1991 |
| EP | 0451981 | 10/1991 |
| EP | 0520296 | 12/1992 |
| EP | 0367752 | 1/1993 |
| EP | 0595237 | 10/1993 |
| EP | 0575952 | 12/1993 |
| EP | 0671146 | 9/1995 |
| EP | 0732590 | 9/1996 |
| EP | 0797951 | 10/1997 |
| FR | 2574299 | 12/1984 |
| FR | 2577808 | 2/1985 |
| GB | 2222251 | 2/1990 |
| JP | 7-255706 | 10/1995 |
| WO | 8700413 | 7/1986 |
| WO | 9109139 | 6/1991 |
| WO | 9202175 | 2/1992 |
| WO | 9215863 | 9/1992 |
| WO | 9303673 | 3/1993 |
| WO | 9409713 | 5/1994 |
| WO | 9637148 | 11/1996 |
| WO | 9742882 | 11/1997 |

OTHER PUBLICATIONS

Lane et al., "Ultraviolet–Laser Ablation of Skin", *IBM Research Report*, 1984.

* cited by examiner

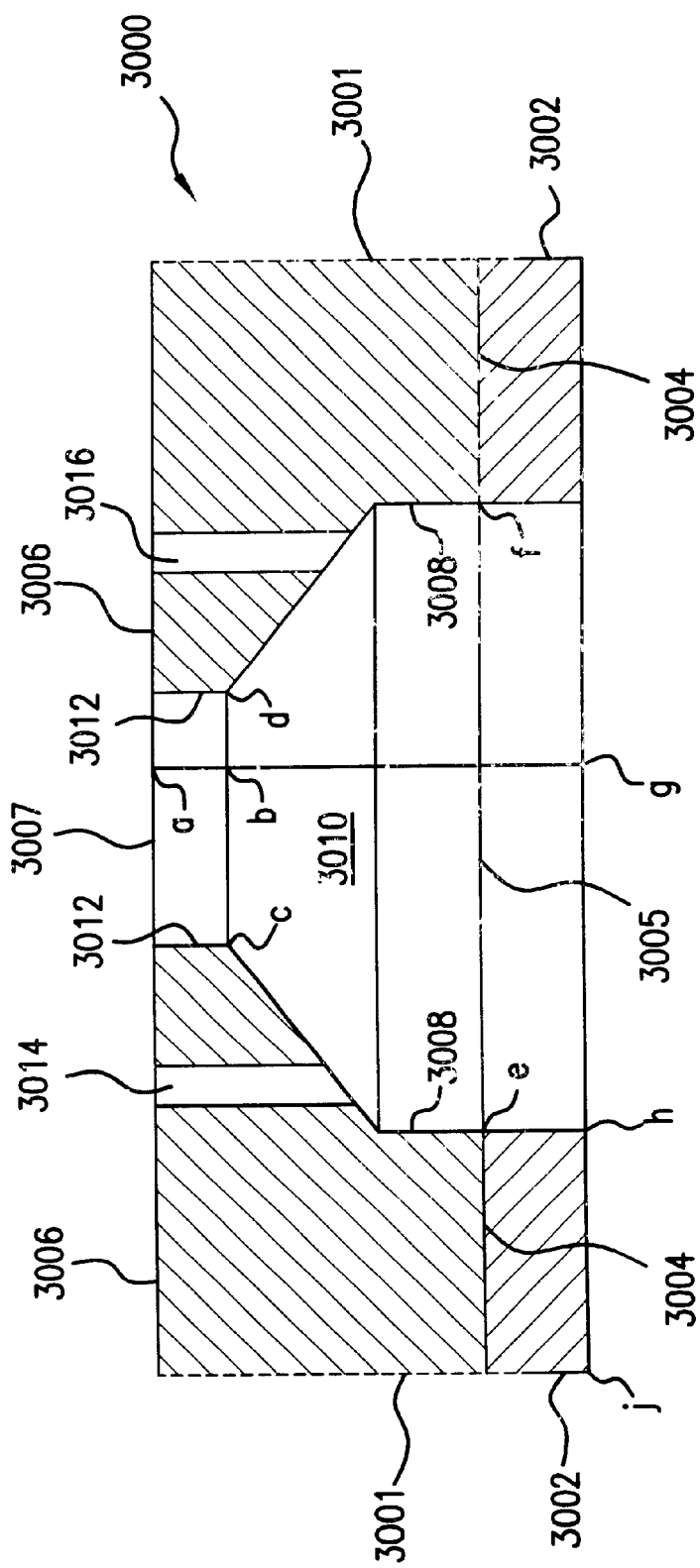

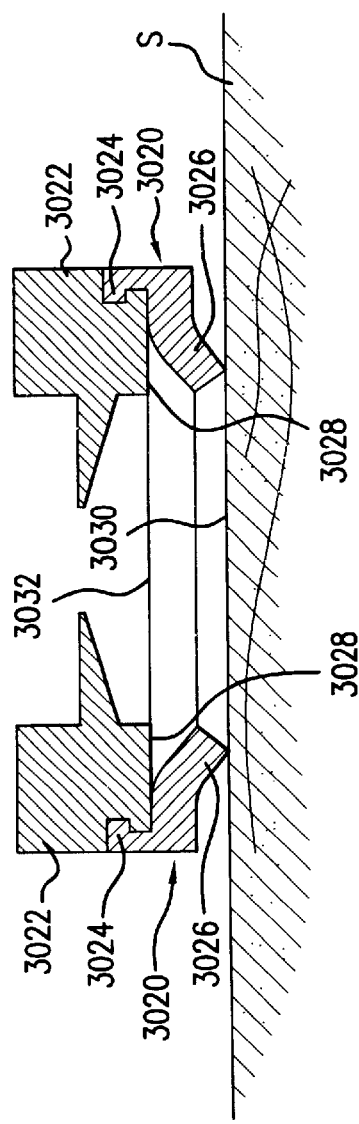
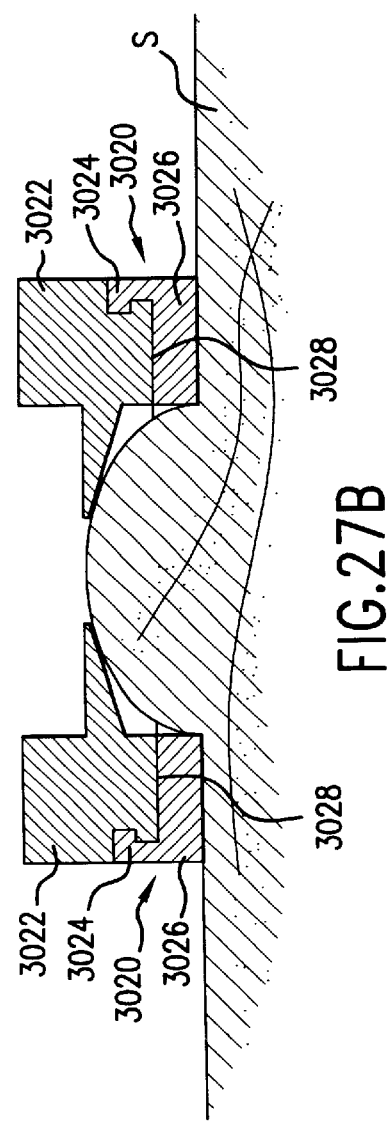
FIG.27A
FIG.27B

METHOD AND APPARATUS FOR OBTAINING BLOOD FOR DIAGNOSTIC TESTS

CROSS REFERENCES TO COPENDING APPLICATIONS

This relates to three patent applications, each entitled METHOD AND APPARATUS FOR OBTAINING BLOOD FOR DIAGNOSTIC TESTS, Ser. Nos. 08/982,561, 08/982,323, and 08/982,324 filed on even date herewith. The specifications, drawings and claims of these applications are incorporated herein by reference. All of the foregoing applications are commonly owned by the assignee of this invention.

This application is a continuation of U.S. Ser. No. 09/612,722, filed Jul. 10, 2000, now U.S. Pat. No. 6,306,104, which is a divisional of U.S. Ser. No. 08/982,721, filed Dec. 2, 1997, now U.S. Pat. No. 6,093,156, which is a continuation-in-part of U.S. Ser. No. 08/759,698, filed Dec. 6, 1996, now U.S. Pat. No. 6,063,039, and claims priority from U.S. Provisional Application No. 60/036,395, filed Jan. 24, 1997.

BACKGROUND OF THE INVENTION

1. Field of the Invention

This invention relates to a method and apparatus for obtaining samples of blood for diagnostic purposes.

2. Discussion of the Art

The prevalence of diabetes has been increasing markedly in the world. At this time, diagnosed diabetics represent about 3% of the population of the United States. It is believed that the total actual number of diabetics in the United States is over 16,000,000. Diabetes can lead to numerous complications, such as, for example, retinopathy, nephropathy, and neuropathy.

The most important factor for reducing diabetes-associated complications is the maintenance of an appropriate level of glucose in the blood stream. The maintenance of the appropriate level of glucose in the blood stream may prevent and even reverse many of the effects of diabetes.

Glucose monitoring devices of the prior art have operated on the principle of taking blood from an individual by a variety of methods, such as by needle or lancet. An individual then coats a paper strip carrying chemistry with the blood, and finally inserts the blood-coated strip into a blood glucose meter for measurement of glucose concentration by determination of change in reflectance.

The medical apparatus of the prior art for monitoring the level of glucose in the blood stream required that an individual have separately available a needle or lancet for extracting blood from the individual, strips carrying blood chemistry for creating a chemical reaction with respect to the glucose in the blood stream and changing color, and a blood glucose meter for reading the change in color indicating the level of glucose in the blood stream. The level of blood glucose, when measured by a glucose meter, is read from a strip carrying the blood chemistry through the well-known process of reading reflectometers for glucose oxidation.

Generally lancets comprise a blade and a pressable end opposed thereto, with the blade having an acute end capable of being thrust into skin of a human. By striking the pressable portion, the acute end of the blade will pierce the skin, for example, of the finger. The finger lancet is primarily used to obtain small volumes of blood, i. e., less than 1 mL. Diabetics use the finger lancet to obtain volumes of blood less than 25 $\mu$L for analysis for glucose. A small amount of blood for the blood test will ooze out of the skin. There are many small blood vessels in each finger so that a finger can be squeezed to cause a larger drop of blood to ooze. The finger is one of the most sensitive parts of the body; accordingly, the finger lancet leads to even more pain than what would be experienced by extracting blood via lancet at a different body site. The finger lancet presents another problem because of the limited area available on the fingers for lancing. Because it is recommended that diabetics monitor their blood glucose levels four to six times per day, the limited area on the fingers calls for repeated lancing of areas that are already sore. Because fingers are sensitive to pain, it is a recent tendency that the arm is subjected to blood sampling. See, for example, U.S. Pat. No. 4,653,513. The device of U.S. Pat. No. 4,653,513 comprises a cylindrical housing and a lancet support, which has a gasket or flexible portion slidably accommodated in the housing. Springs will retract the lancet support to thereby reduce air pressure in the housing so that it sucks a blood sample, automatically and immediately after a lancet pierces the skin. See also U.S. Pat. No. 5,320,607, which discloses a device comprising a sealed vacuum chamber in a state of preexisting reduced pressure, a support member for the sealed vacuum chamber, the support member defining a suction portion adjacent the sealed vacuum chamber, the suction portion, in cooperation with the sealed vacuum chamber, exposing an area of the skin of a patient to a reduced pressure state when the device is actuated, and means arranged within the suction portion for slightly rupturing a portion of the area of skin of the patient exposed to the reduced pressure state.

Because the blood volume requirements for a standard glucose test strip are typically 3 $\mu$L or more, an area of the body that can generate that much blood from a lancet wound must be used. It is believed, however, that improvements in glucose test strip technology will reduce the volume of blood needed to 1 to 3 $\mu$L. Because the finger is well supplied with blood and the amount of blood can be increased by squeezing the finger after lancing, the finger is the currently preferred body site for lancing, even though lancing of the finger is painful.

A less painful technique for obtaining body fluids could be found if a reliable method were found for lancing a body part that is less sensitive to pain than the finger and obtaining a useful amount of blood from that body part. A body part such as the forearm is much less sensitive to pain than the finger, but the amount of blood resulting from the lancing procedure is generally of an inadequate volume for use with current detection technology. Ways of increasing blood flow to the finger are common knowledge. The recommendation is made to diabetics to run their finger under hot water prior to lancing to improve the blood flow in the finger and the amount of blood collected from the finger. Running hot water over a body part to improve blood flow is impractical for areas such as the forearm or thigh. The availability of hot water is also a concern.

It would be desirable to develop a technique and apparatus for obtaining blood for diagnostic purposes in a painless, reliable manner.

SUMMARY OF THE INVENTION

This invention provides a method and apparatus for extracting a sample of blood from a patient for subsequent diagnostic tests, e.g., glucose monitoring. In one aspect of the invention, the method comprises the steps of:

(a) forming an unobstructed opening in the area of the skin from which the sample of blood is to be extracted; and (b) extracting the sample of blood from the unobstructed opening in the skin, with the aid of vacuum and stretching of the skin.

In a preferred embodiment of the method, step (a) is preceded by the step of increasing the availability of blood in the portion of the skin from which the sample is to be extracted. In this preferred embodiment, the availability of blood in the portion of the skin from which the sample is to be extracted can be increased by means of a vacuum, which is applied to the surface of the skin in the vicinity of the opening prior to forming the opening in the skin. The vacuum causes the portion of the skin in the vicinity of the blood extraction site to become engorged with blood. The vacuum also causes the portion of the skin in the vicinity of the blood extraction site to become stretched. An opening in this stretched portion of skin can be formed with a cutting or puncturing device, e.g., a lancet, or other device capable of forming an opening in the skin, e. g., a laser or a fluid jet. If a cutting or puncturing device is used to form the opening, it must be retracted from the opening prior to the step of extracting the sample of blood from the opening. This retraction will allow the unrestricted flow of blood through the opening. After the opening is formed, a vacuum is used to aid in extracting the sample of blood from the opening in the skin. The sample can be analyzed from the drops of blood that collect on the surface of the skin at the site of the opening by applying the blood directly to a glucose detector. It is preferred, however, that the sample be collected in such a manner, e. g., via a capillary tube, that it can be analyzed by conventional diagnostic devices, such as, for example, a biosensor. In another preferred embodiment, the sample can be collected in a collection zone that is integrated with a conventional diagnostic device, e. g., a biosensor. If a glucose detector is used, it may be held stationary within the device throughout the blood collection procedure or may be moved nearer the lancing site after the lancet is retracted by a triggering or other mechanism.

In an alternative of the aforementioned preferred embodiment, the availability of blood in the area of the skin from which the sample is to be extracted can be increased by means of applying thermal energy to that area of skin. The thermal energy causes the blood in that area of the skin to flow more rapidly, thereby allowing more blood to be collected per given unit of time. In this alternative embodiment, steps (a) and (b) can be carried out in the same manner as they were carried out in the aforementioned preferred embodiment.

In another aspect of the invention, an apparatus for collecting a sample of body fluid for analysis in a diagnostic test, e. g., blood, is provided. In a preferred embodiment, the apparatus comprises:

(a) a housing;
(b) a device for forming an unobstructed opening in an area of skin from which said sample is to be extracted, preferably a lancing assembly; and
(c) a vacuum pump. It is also possible to dispense with the housing. However, the housing is preferred for the convenience of the patient and the protection of the components.

The vacuum pump requires a source of power. If the apparatus includes a housing, the source of power can be disposed within the housing. Alternatively, the source of power can be external to the housing.

The preferred device for forming an unobstructed opening in the area of the skin from which the sample of blood is to be extracted is a lancing assembly, which comprises a lancet for forming an opening in the skin. Alternatively, the unobstructed opening in the skin can be formed by a laser or a fluid jet.

The vacuum pump can serve the dual purposes of (1) stretching the skin and (2) enhancing the extraction of the sample of blood from the unobstructed opening in the skin. Preferably, the vacuum pump can serve the triple purposes of (1) stretching the skin, (2) increasing the availability of blood to the area of the skin from which the sample is to be extracted, and (3) enhancing the extraction of the sample of blood from the unobstructed opening in the skin. Preferably, the housing further contains electronics having programmed instructions to switch the vacuum pump on and off to maintain the desired level of vacuum.

The apparatus preferably contains valves, such as, for example, solenoid valves, for triggering the lancet of the lancing assembly and releasing the vacuum at the conclusion of the blood extraction procedure. The apparatus can optionally contain a heating element to increase the availability of blood to the area of the skin from which the sample is to be extracted. The apparatus can also contain a glucose detector integrated with the apparatus, e. g., a biosensor, to analyze the sample of blood collected by the apparatus.

The method and apparatus of this invention provide several advantages over the methods and apparatus of the prior art. First, a sufficient amount of blood can be extracted from parts of the body, other than the finger, for conducting glucose monitoring tests. Second, by rendering other parts of the body suitable for extracting blood, the use of a painful finger lance can be avoided. Third, by increasing the availability of blood at the site where the blood is to be extracted, the period of time required for extracting the sample can be reduced. Because of these advantages, the diabetic patient is more likely to monitor glucose levels in the blood at the intervals prescribed by his doctor.

BRIEF DESCRIPTION OF THE DRAWINGS

FIG. 2 also illustrates the spatial relationship between the nosepiece of lancing assembly and a glucose detector, e.g., a biosensor.

FIG. 11, comprising In FIG. 11A and 11B, the housing of the apparatus is open. In FIG. 11C, the housing of the apparatus is closed.

FIG. 12, comprising In FIG. 12A, the housing of the apparatus is open. In FIG. 12B, the housing of the apparatus is closed.

FIG. 13, comprising In FIG. 13A, the housing of the apparatus is open. In FIG. 13B, the housing of the apparatus is partially open. In FIG. 13C through 13E, the housing of the apparatus is closed.

FIG. 14, comprising In FIG. 14A through 14C, the housing of the apparatus is closed.

FIG. 26 is an elevational view of a cross section of a preferred embodiment of a nosepiece of this invention.

FIG. 27A is an elevational view of a cross section of a preferred embodiment of a nosepiece of this invention, wherein the seal is in a first position. FIG. 27B is an elevational view of the nosepiece of FIG. 27A, wherein the seal is in a second position.

DETAILED DESCRIPTION

Figure 1:
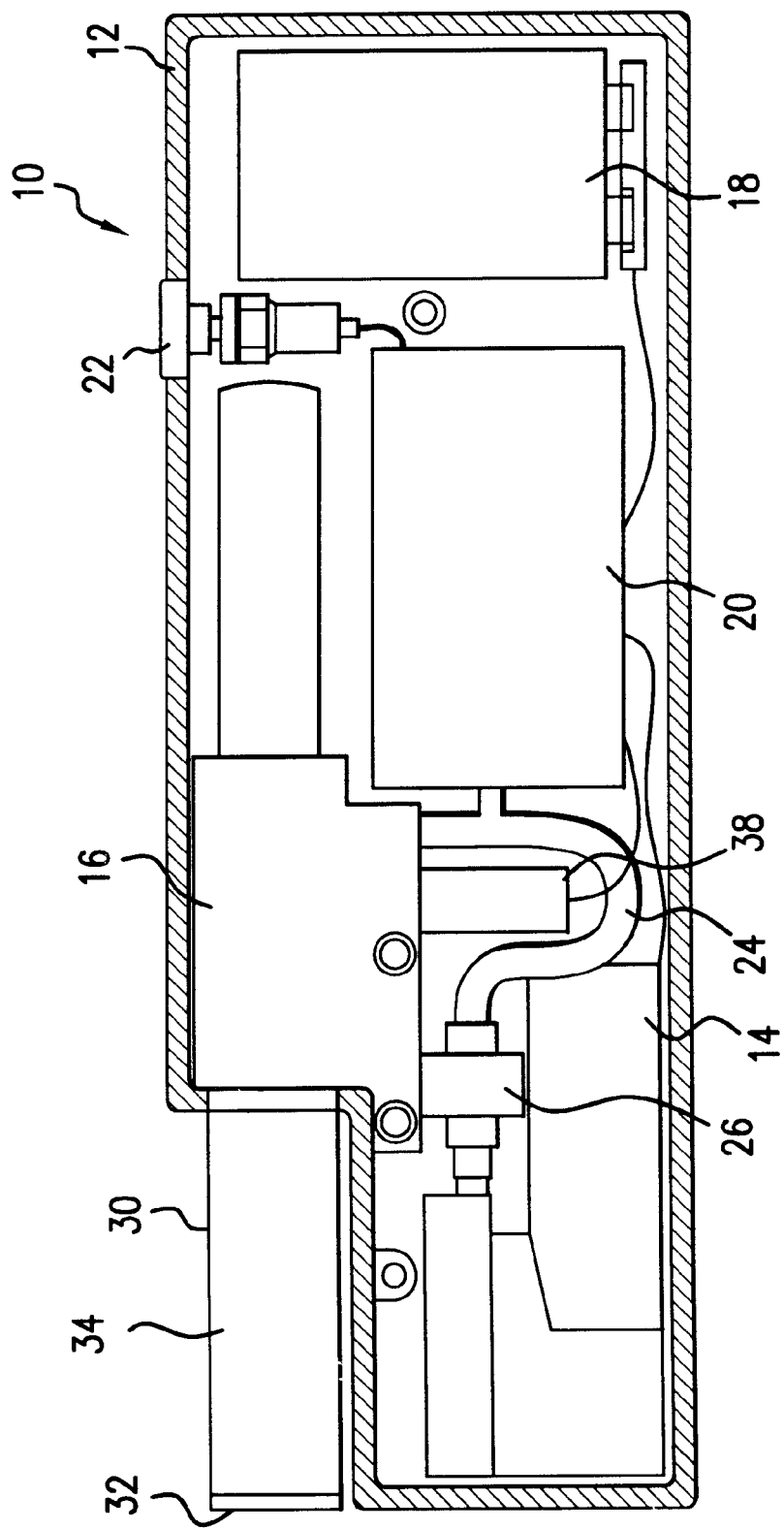
FIG. 1 is a plan view of the components of a preferred embodiment of the apparatus of this invention. In this Figure, the cover of the housing is removed.

The embodiments of this invention require the following steps to carry out the function of obtaining a sample of blood for carrying out a diagnostic test, e. g., glucose monitoring:

(a) a housing having a sealable chamber located therein and a sealable opening in fluid communication with said sealable chamber, (b) a power source, (c) a vacuum pump operably connected to said power source, said vacuum pump in communication with said sealable chamber, (d) a lancing assembly positioned within said sealable chamber, said lancing assembly capable of moving a lancet towards said sealable opening, and (e) a fluid collector positioned in said sealable chamber, said fluid collector in fluid communication with said sealable opening.

An unobstructed opening in the area of the skin from which the sample of blood is to be extracted is formed by a piercing device or some other type of device capable of forming an unobstructed opening in the skin. Piercing devices suitable for this invention include, but are not limited to, mechanical lancing assemblies. Other types of devices capable of forming an unobstructed opening in the skin include, but are not limited to, lasers and fluid jets. Other types of devices capable of forming an unobstructed opening in the skin can be used, and this disclosure should not be construed so as to be limited to the devices listed. Mechanical lancing assemblies are well-known in the art. These assemblies comprise standard steel lancets, serrated devices, and multiple tip devices. The lancets can be made from metal or plastic. Multiple tip devices provide redundancy, which can reduce the number of failures and increase the volume of blood extracted.

Lasers suitable for forming an unobstructed opening in the skin to draw blood are also well-known in the art. See for example, U.S. Pat. Nos. 4,775,361, 5,165,418, 5,374,556, International Publication Number WO 94/09713, and Lane et al. (1984) IBM Research Report—"Ultraviolet-Laser Ablation of Skin", all of which are incorporated herein by reference. Lasers that are suitable for forming an unobstructed opening in the skin include Er:YAG, Nd:YAG, and semiconductor lasers.

Fluid jets suitable for forming an unobstructed opening in the skin employ a high pressure jet of fluid, preferably a saline solution, to penetrate the skin.

Regardless of what type of device is utilized to form an unobstructed opening in the skin, the opening formed by the device must be unobstructed. As used herein, the term "unobstructed" means free from clogging, hampering, blocking, or closing up by an obstacle. More specifically, the expressions "unobstructed opening in the area of the skin from which the sample is to be extracted", "unobstructed opening in the skin", and the like are intended to mean that the portion of the opening below the surface of the skin is free from any foreign object that would clog, hamper, block, or close up the opening, such as, for example, a needle of any type. For example, if a lancet is used to form the opening, it must be retracted from the opening prior to the commencement of the extraction of blood. Because lasers and fluid jets do not require contact with the skin to form openings in the skin, these types of devices typically provide unobstructed openings. However, these expressions are not intended to include foreign objects at the surface of the skin or above the surface of the skin, such as, for example, a glucose monitor. This feature, i. e., the unobstructed opening, can be contrasted with the opening used in the method and apparatus described in U.S. Pat. No. 5,320,607, in which the piercing and cutting means remains in the skin during the duration of the period of blood extraction. By leaving the opening unobstructed, blood can be extracted much more rapidly from the opening than it would be extracted if the piercing and cutting means were allowed to remain in the opening. In addition, the requirement of an unobstructed opening exposes the body to a foreign object either not at all or for only a very short period of time, which is welcomed by the patient.

The step of extracting the sample of blood from the opening in the skin is carried out by a combination of extraction enhancing elements. Extraction enhancing elements suitable for use in this invention include, but are not limited to, vacuum, skin stretching elements, and heating elements. It has been discovered that when these elements are used in combination, the volume of blood extracted is greatly increased, particularly when a vacuum is applied in combination with skin stretching. In this combination, the vacuum not only causes the blood to be rapidly removed from the unobstructed opening by suction, it also causes a portion of the skin in the vicinity of the opening to be stretched. Stretching of the skin can be effected by other means, such as mechanical means or adhesives. Mechanical means include devices for pinching or pulling the skin; adhesives bring about stretching of the skin by means of pulling. It is preferred to use a vacuum to effect stretching of the skin. Like a vacuum, a heating element operates more effectively in combination with other techniques, e. g., stretching of the skin. This feature, i.e., the extraction enhancing element, can be contrasted with the system described in U.S. Pat. No. 5,279,294 in which no such extraction enhancing elements are utilized and the system described in European Patent Applications 0351892 and 0127958, wherein the sensor is either needle-like in nature or fits within a hollow needle.

In the preferred embodiment of this invention, step (a), the step of forming the unobstructed opening, is preceded by the step of increasing the availability of blood at the area of the skin from which the sample is to be extracted. The availability of blood at a given area of the skin can be increased by at least two methods. In one method, a vacuum can be used to cause blood flowing through blood vessels to pool in the area of the skin where the vacuum is applied. In another method, heat can be used to cause blood flowing through blood vessels to flow more rapidly in the area of the skin where heat is applied, thereby allowing a greater quantity of blood to be extracted from the blood extraction site per unit of time. Although the step of increasing the availability of blood in the vicinity of the blood extraction site is not required, the employment of this step can result in a greater volume of blood extracted. Elements for increasing the availability of blood at a blood extraction site that are suitable for use in this invention include, but are not limited to, vacuum, localized heating element, skin stretching element, and chemicals. As stated previously, applying a vacuum to the area of the skin from which blood is to be extracted can increase blood availability under and within the skin at the application site. The vacuum can also be used to stretch the skin upwardly into a chamber, thereby increasing pooling of blood under and within the skin. This combination of vacuum and skin stretching can be an extension of the combination used to extract blood from the opening in the skin, as previously described. It is well-known that heat can increase perfusion on the large scale of a limb or a finger. Chemical means, such as histamine, can be used to cause a physiological response to increase perfusion under and within the skin.

In the preferred embodiments of the invention, the extracted blood is also collected. The step of collecting the sample of blood can be carried out in a variety of ways using a variety of fluid collectors. For example, the blood can be collected in capillary tubes or absorbent paper. Alternatively, the blood can be allowed to remain in the lancet assembly, from which it can used directly in a diagnostic test. Most preferably, the sample of blood is collected on the application zone of a glucose detector, from where it can be used directly to provide an indication of the concentration of glucose in the blood. Such a glucose detector may be held stationary within the device throughout the blood collection procedure or may be moved nearer the lancing site after the lancet is retracted by a triggering or other mechanism. The apparatus of the present invention may contain more than one fluid collector. A sensor pack containing a plurality of blood glucose sensors is disclosed in EPO 0732590A2. Regardless of the manner in which the blood sample is collected, the sample can be analyzed at a time later than the time of collection or at a location remote from the location of collection or both.

A preferred embodiment of the invention will now be described in detail. Blood extraction device 10 comprises a housing 12. Disposed within the housing 12 are a vacuum pump 14, a lancing assembly 16, a battery 18, and electronics 20. A switch 22 is provided to activate electronics 20.

The housing 12 is preferably made from a plastic material. It is preferably of sufficient size to contain all of the components that are required for forming an unobstructed opening in the area of the skin from which the sample of blood is to be extracted, extracting the sample of blood from the unobstructed opening in the skin, preferably with the aid of a vacuum and a stretching of the skin, and collecting the extracted sample in an amount sufficient to carry out a diagnostic test. Methods of preparing the housing 12 are well-known to one of ordinary skill in the art. As stated previously, the housing 12 is not required, but is preferred for the convenience of the patient and the protection of the components.

The vacuum pump 14 must be capable of providing a vacuum that will provide sufficient suction to stretch the portion of the skin in the region from which the sample of blood is to be extracted. Typically, the portion of stretched skin is raised a distance of 1 to 10 mm, preferably 3 to 5 mm, from the plane of the body part of which it is a portion. As the suction provided by the vacuum pump 14 is stretching the appropriate portion of skin, the suction provided by the vacuum pump 14 also causes the stretched portion to become engorged with blood. The level of suction provided must be sufficient to cause a relatively large volume of blood to become engorged at the point that the vacuum is applied. The vacuum pump 14 must also be capable of providing sufficient suction to extract blood from the opening in the skin at a rate sufficient to extract at least 1 $\mu$L of blood within a period of five minutes. A vacuum pump 14 that is suitable for the device of this invention can be a diaphragm pump, a piston pump, a rotary vane pump, or any other pump that will perform the required functions set forth previously. Typically, the vacuum pump 14 employs a self-contained permanent magnet DC motor. Vacuum pumps that are suitable for this invention are well-known to those of ordinary skill in the art and are commercially available. A vacuum pump suitable for use in the present invention is available from T-Squared Manufacturing Company, Nutley, N.J., and has the part number T2-03.08.004.

The vacuum pump 14 is preferably capable of providing a pressure of down to about −14.7 psig, and is more preferably operated at from about −3.0 psig to about −10.0 psig. The area of the skin subjected to vacuum preferably ranges up to about 50 $cm^2$, more preferably from about 0.1 to about 5.0 $cm^2$. The period of vacuum application prior to forming the opening in the skin, i. e., for increasing the availability of blood to the application site, preferably ranges up to about 5 minutes, preferably from about 1 to about 15 seconds. The period of vacuum application subsequent to forming the opening in the skin, i. e., for aiding in the extraction of blood from the unobstructed opening, preferably ranges up to about 5 minutes, preferably from about 1 to about 60 seconds. The vacuum provided by the vacuum pump 14 can be continuous or pulsed. A continuous vacuum is preferred for the reason that it requires fewer components than does a pulsed vacuum. It is preferred that the vacuum applied not cause irreversible damage to the skin. It is preferred that the vacuum applied not produce bruises and discolorations of the skin that persist for several days. It is also preferred that the level of vacuum applied and duration of application of vacuum not be so excessive that it causes the dermis to separate from the epidermis, which results in the formation of a blister filled with fluid.

The vacuum pump feature offers significant advantages over the method and apparatus described in U.S. Pat. No. 5,320,607, in which a sealed vacuum chamber in a state of preexisting reduced pressure is used. The use of a vacuum pump provides the user with greater control of blood extraction conditions than does a sealed vacuum chamber in a state of preexisting reduced pressure. For example, if the vacuum is insufficient, energy can be provided to the vacuum pump to bring about a higher level of vacuum, thereby providing greater suction.

The lancing assembly 16 comprises at least one lancet. Standard lancets can be used in the lancing assembly of this invention. Narrow gauge (28 to 30 gauge) lancets are preferred. Lancets suitable for this invention can be made from metal or plastic. Lancets suitable for this invention can have single points or multiple points. The depth of penetration of the lancet preferably ranges from about 0.4 to about 2.5 mm, more preferably from about 0.4 to about 1.6 mm. The length of the lancet or lancets preferably ranges from about 1 mm to about 5 mm. The lancing assembly is preferably located so that the user can easily replace used lancets. The lancet of the lancing assembly 16 can be cocked manually or automatically, e. g., by means of a vacuum-actuated piston or diaphragm. The lancet of the lancing assembly 16 can be triggered manually or automatically, e. g., by means of a vacuum-actuated piston or diaphragm.

Lancing assemblies are well-known in the art. Representative examples of lancing assemblies suitable for this invention are described in U.S. Pat. Nos. Re. 32,922, 4,203, 446, 4,990,154, and 5,487,748, all of which are incorporated herein by reference. A particularly suitable lancing assembly for this invention is described in U.S. Pat. No. Re. 32,922. However, any lancing assembly selected should operate in conjunction with the other features of the apparatus of this invention. For example, if a vacuum is employed, the lancing assembly must be designed so that a vacuum can be formed and drawn through the assembly. The lancing assembly can be designed to allow automatic cocking and automatic triggering of the lancet.

While conventional lancing assemblies are suitable for use in this invention, a lancing assembly that utilizes differential gas pressure to thrust a lancet into skin tissue has been developed for use with this invention. As used herein, the expression "differential gas pressure" means the difference in gas pressure between a gas source at a high pressure, e. g., ambient air or pressurized air, and a gas source at a low pressure, e. g., air within a vacuum. In any event, the pressure of a gas source at high pressure exceeds the pressure of a gas source at low pressure.

FIGS. 18, 19, 20, and 21 illustrate an embodiment of a lancing assembly suitable for use in this invention. In this embodiment, the gas is air. However, it should be noted that other gases, e. g., nitrogen, carbon dioxide, can be used in place of air for the gas source at low pressure, the gas source at high pressure, or both. The lancing assembly 60 of this embodiment comprises a housing 62, a piston 64 having a lancet holder 66, a lancet assembly 67 comprising a lancet 67a inserted into a body 67b, a piston biasing means 68, which, in this embodiment, is a return spring, and a cap 70. The housing 62 has a manifold 72 into which a three-way valve 74 can be fitted. See FIGS. 20 and 21 for manner of positioning the three-way valve 74 in the manifold 72. The three-way valve 74 selectively allows air from a source external to the housing 62 to pass through an inlet port 76 to a bore port 78, thereby causing the level of pressure in the bore 80 to increase. The increased pressure in the bore 80 causes the piston 64 to be thrust toward the target skin tissue while simultaneously compressing the return spring 68. The piston 64 is halted by the cap 70 or by another structure designed to limit the penetration depth of the lancet 67a in the skin. Such other structure can be a glucose detector in the form of a test strip, which will be described later, or a lancet stop, such as that designated by reference numeral 39 in FIG. 2. The three-way valve 74 then directs the air in the bore 80 to flow out through an exit port 82 to a source of low-pressure air, e. g., an evacuated air cavity in the apparatus, thereby causing the level of pressure in the bore 80 to decrease, and consequently allowing the return spring 68 to force the piston 64 back to its pre-thrust position in the bore 80.

Proper sizing of the components is needed to satisfy both the dimensional limitations of the apparatus and the performance requirements of the lancing process, as explained further below. The lancing assembly of this invention occupies no more space than a conventional spring-powered device and typically requires less distance for the lancet to travel.

The bore 80, typically cylindrical in shape, is the chamber in which differential air pressure is generated to thrust the piston 64 toward the target skin tissue. The bore 80 also functions to guide the piston 64 toward the target skin tissue, while providing a low-friction pneumatic seal against o-ring 84. The o-ring 84 is desirable for preventing high-pressure air from leaking out of the bore 80 during the lancing procedure, because the leakage of high-pressure air will decrease the level of air pressure in the bore 80, with the result that the thrusting speed of the piston 64 would be reduced. The manifold 72 is shaped to fit the three-way valve 74, which selectively connects bore port 78 to either inlet port 76 or exit port 82 to direct the flow of air to or from the bore 80. The exit port 82 is typically plumbed to a source of low-pressure air. The inlet port 76 is typically plumbed to a source of air pressure higher than that of the low-pressure air source. The ports 76, 78, and 82 are positioned to communicate with corresponding ports of the three-way valve 74, and are preferably sized to cause less flow resistance than the ports on the three-way valve 74.

The piston 64 is the moving component of the lancing assembly 60. It is preferably cylindrical in shape, and has a lancet holder 66 and a circumferential gland 83 for a standard o-ring 84. The lancet holder 66 is designed to securely mount a disposable lancet assembly 67, which is inserted by the user in the same manner as is used with a conventional lancing device. The lancet assembly 67 comprises a lancet 67a, which is inserted into a molded plastic body 67b. The function of the o-ring 84 is to act as a seal to maintain air pressure in the bore 80 during lancing. The o-ring should cause negligible sliding friction force along the bore 80 (negligible compared to pressure forces acting on the piston 64). The length of the shaft 64a of the piston 64 is chosen to provide a desired stroke distance, typically 5 mm to 25 mm. The major dimension of the top surface 64b of the piston 64, typically 5 mm to 10 mm in diameter for a cylindrically-shaped piston, is chosen to provide adequate surface area for pressure forces to thrust the piston 64 and the lancet assembly 67.

The return spring 68, typically a metal helical spring, is compressed between the piston 64 and the cap 70. The spring 68 forces the piston 64 to its maximum depth in the bore 80 when substantially no differential air pressure exists in the bore 80. This action properly positions the piston 64 to begin the lancing process. This position of the piston 64 is the position in which the piston 64 is furthest away from the target skin tissue when the apparatus is placed against the target skin tissue. The spring 68 also retracts the lancet assembly 67 in the lancet holder 66 away from the target skin tissue at the end of the lancing process. The spring force must be sufficient to overcome the weight of the piston/lancet system plus the sliding friction of the o-ring 84.

The cap 70 is securely positioned in the housing 62. The cap 70 properly positions the return spring 68 while providing sufficient radial clearance for the spring 68 to compress freely. The cap 70 has a passage 88 through which the lancet holder 66 can move. The cap 70 can also function to help guide the piston 64 toward the target skin tissue.

Figure 22B:
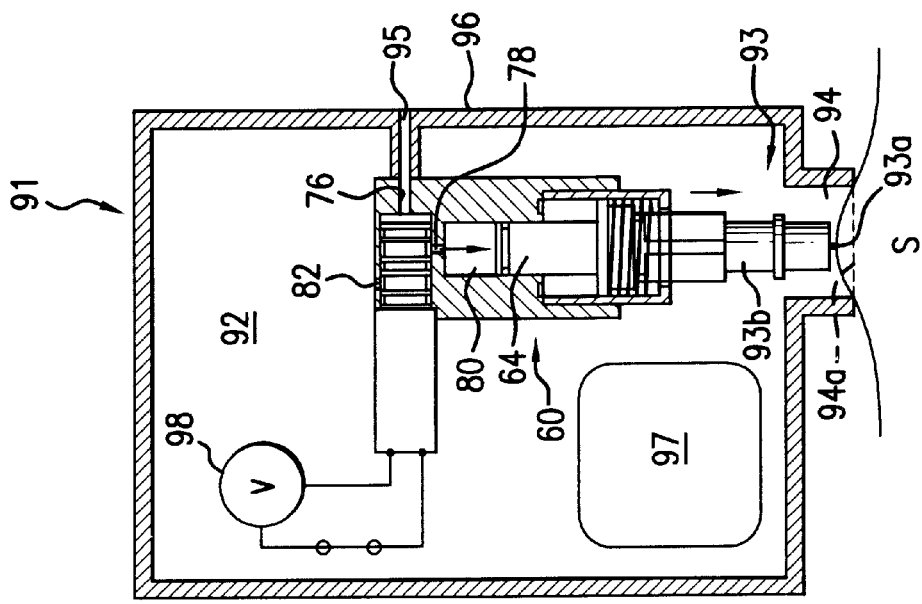
FIGS. 22A, 22B, and 22C are schematic diagrams illustrating the lancing assembly of this invention in the pre-lancing position, the lancing position, and the post-lancing position, respectively.
Figure 22A:
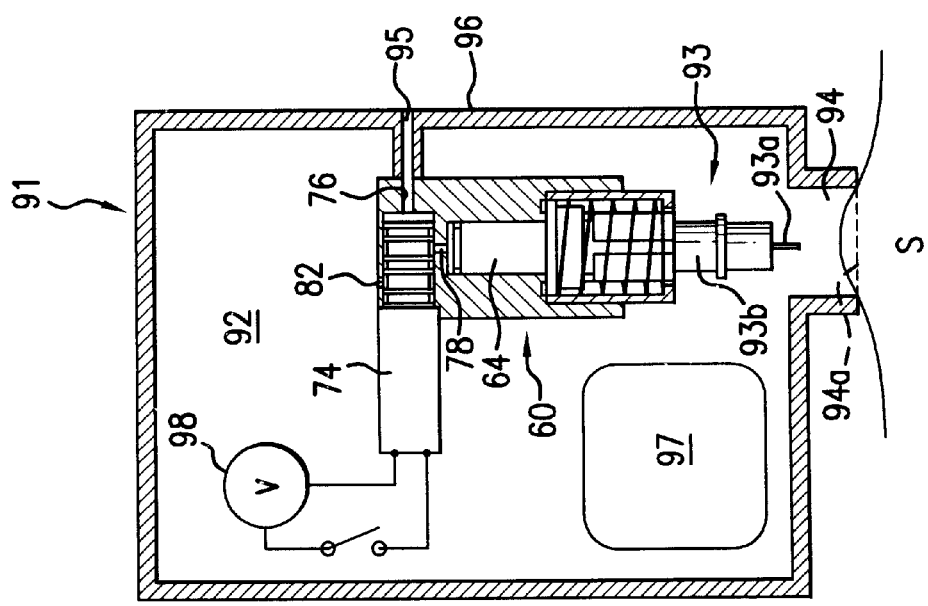
Figure 22C:
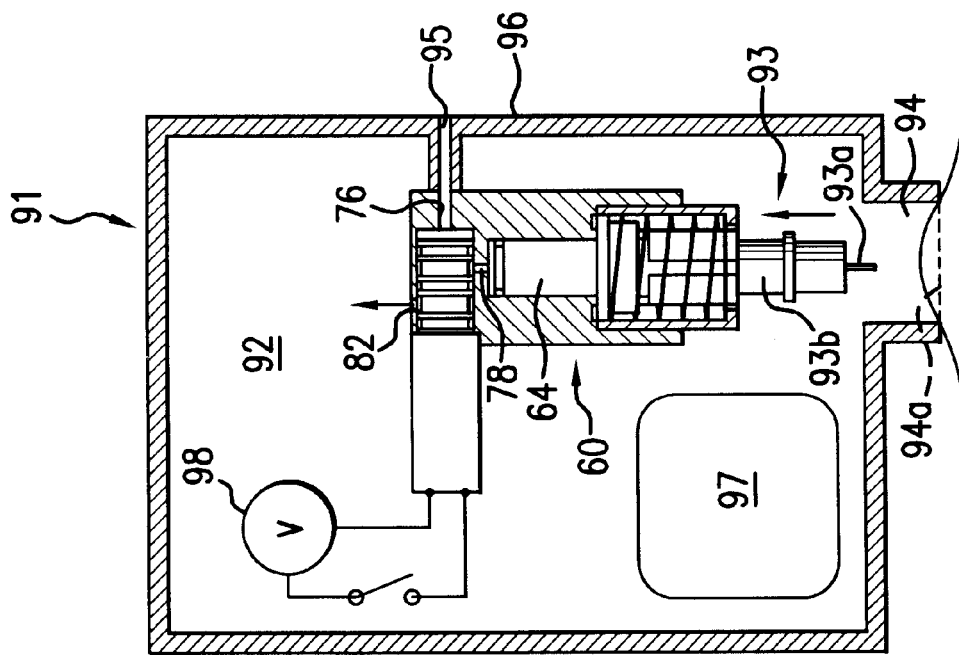

FIGS. 22A, 22B, and 22C illustrate an installation of the lancing assembly of FIGS. 11 and 12 inside a hypothetical apparatus 91. The lancing assembly 60 is fixed inside a cavity 92 of the apparatus 91 and fitted with a three-way solenoid valve 74 and a standard disposable lancet assembly 93 as shown. The lancet assembly 93 comprises a lancet 93a, which is inserted into a molded plastic body 93b. The apparatus 91 has a lower passage 94 through which the lancet assembly 93 can move to form an unobstructed opening in the area of the skin "S" that is circumscribed by a circular opening 94a (shown by dashed line) in the lower passage. A side port 95 on a wall 96 of the apparatus 91 connects inlet port 76 on the lancing assembly 60 to ambient air surrounding the apparatus 91. The apparatus 91 also has a vacuum source 97 to maintain the air pressure in the cavity 92 at the level at which the apparatus operates, and a voltage source 98 to selectively activate the three-way solenoid valve 74. With voltage off, the three-way solenoid valve 74 connects the bore 80 of the lancing assembly 60 with the cavity 92 via exit port 82, causing the piston 64 to experience no differential air pressure.

In the "Ready" mode (FIG. 22A), the lower passage 94 of the apparatus 91 is placed across the target skin. The vacuum pressure of the apparatus reaches operational level $P_v$, which is substantially less than ambient pressure $P_a$ (e.g., $P_v=-7.5$ psig, $P_a=0$ psig). The target skin is partially drawn into the lower passage 94 by vacuum pressure $P_v$. The voltage of the three-way solenoid valve 74 is initially off, thereby preventing ambient air from entering the lancing assembly 60, allowing the return spring 68 to maintain the lancet 93a at its maximum distance (e. g., 10 mm) from the skin.

In the "Lance" mode (FIG. 22B), the three-way solenoid valve 74 is activated by the voltage source 98, which allows ambient air to flow continuously through the side port 95 of the apparatus 91 through the inlet port 76 and then through the bore port 78 into the bore 80 of the lancing assembly 60. The flow of ambient air increases the air pressure in the bore 80, causing a differential air pressure to act on the piston 64. The differential air pressure acting on the piston 64 rapidly increases and overcomes the opposing force of the return spring 68 and the friction of the o-ring 84, causing the combined mass of the piston 64 and lancet assembly 93 (e. g., 1.5 grams) to thrust toward the target skin. The lancet 93a contacts the skin in a short period of time (e.g., 6 msec) and reaches sufficient speed (e.g., 3.5 m/sec) to form an opening in the skin and to penetrate to a specified depth (e. g., 1.5 mm). The opening in the skin is complete when the thrusting motion of the lancet assembly 93 is halted by some halting means. Suitable means for halting the lancet assembly 93 include, but are not limited to, the cap 70 within the lancing assembly 60, which, in effect, limits the stroke distance of the piston 64, and a lancet stop, as will be described in FIG. 25.

In the "Return" mode (FIG. 22C), the lancet 93a begins retracting from the skin when the voltage of the solenoid is shut off, which occurs after a predefined dwell time (e. g., 10 msec). With voltage off, the three-way solenoid valve 74 reconnects the bore 80 to exit port 82 in the lancing assembly 60 via the bore port 78, causing air from the bore 80 to vent quickly (e.g., 15 msec) through the three-way solenoid valve 74 and out through exit port 82 into the cavity 92, which contains low-pressure air, provided in the apparatus by the vacuum source 97. During venting, the compressed return spring 68 overcomes the combined force of the differential air pressure and the friction of the o-ring 84 to move the piston 64 and the lancet assembly 93 back to the starting position. The lancing cycle, which requires a total of 25 msec in this hypothetical apparatus, is then complete.

The solenoid is driven by the voltage system of the apparatus. Each time the voltage is turned on and then turned off (i. e., one pulse), the three-way solenoid valve 74 switches internally, first directing flow of air into the lancing assembly 60 and then away from the lancing assembly 60. This switching causes the lancet to be thrust into the target skin tissue, then to be retracted away from the target skin tissue. By pulsing the solenoid repeatedly with voltage, the lancing process is repeated. This feature has been termed "repetitive lancing."

Figure 23:
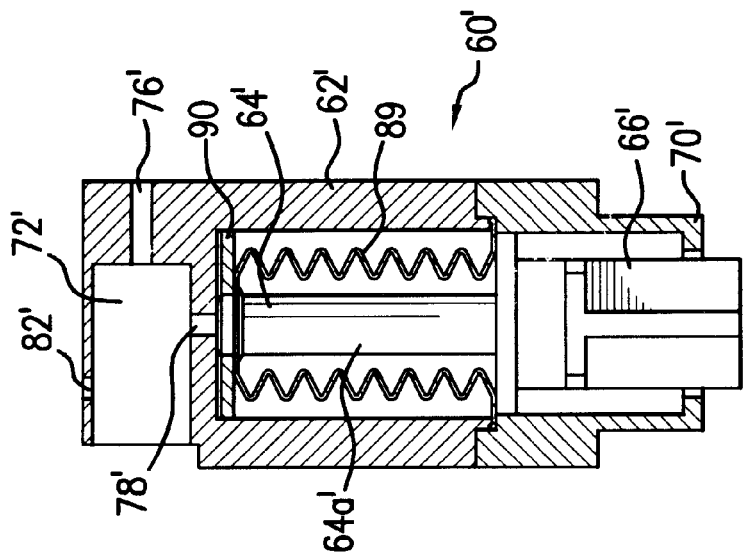
FIG. 23 is an elevational view, in cross section, of another embodiment of the lancing assembly of this invention in assembled configuration.
Figure 24:
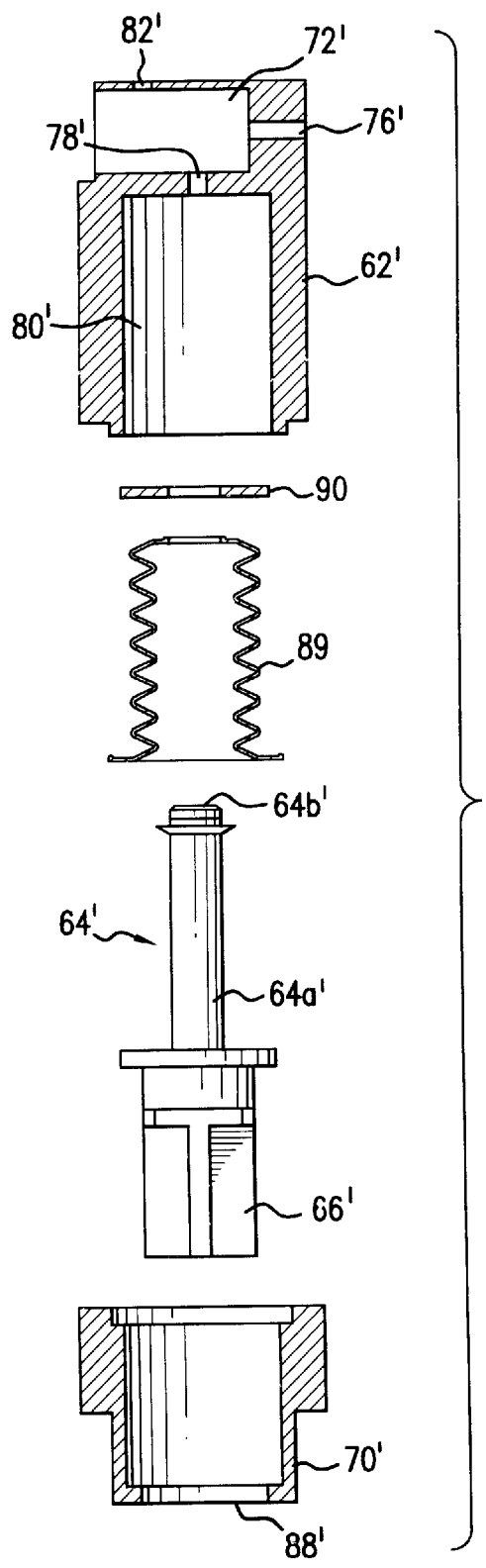
FIG. 24 is an exploded view, in cross section, of the lancing assembly of FIG. 23.

FIGS. 23 and 24 illustrate another embodiment of the lancing assembly. In these figures, prime reference numerals (i. e., reference numerals 60', 62', 64', 64a', 64b', 66', 70', 72', 76', 78', 80', 82', 88') indicate components that are identical or at least substantially similar to components designated by the same reference numerals, but with no prime marking (i. e., reference numerals 60, 62, 64, 66, 70, 72, 76, 78, 80, 82, 88) in FIGS. 18 and 19. In FIGS. 23 and 24, bellows 89, typically a cylindrical molded elastomer, functions as both the pneumatic seal for bore 80' and the means for biasing piston 64'. The bellows 89 effectively replaces the o-ring seal 84 and the return spring 68 shown in FIGS. 18 and 19. To accommodate the bellows 89, the shaft 64a' of the piston 64' must have a radial cross-section dimension sufficiently smaller than that of the bore 80' to provide sufficient clearance for the bellows 89. A plate 90 fastens and seals the bellows 89 to the shaft 64a' of the piston 64', and provides a means of guiding the piston 64' through the bore 80'. A cap 70' and a housing 62' are shaped to fasten and seal the base of the bellows 89 as shown. This embodiment can be used in a manner identical to the embodiment shown in FIGS. 18, 19, 20, 21, 22A, 22B, and 22C. It is clear that the embodiment employing the bellows 89 offers the potential advantage of reduced sliding friction when compared to the embodiment employing the o-ring 84. The bellows does not rub against the surface of the bore in the manner that the o-ring does; therefore, the bellows may result in reduced friction force. The friction force has the undesired effect of reducing the speed of the piston. It is also clear that the bellows requires less dimensional tolerance to be accommodated in the bore 80' than is required to accommodate the o-ring 84 in the bore 80. The bellows does not need to be precisely fitted into the bore, as does the o-ring. If the bore fits too tightly around the o-ring, then excessive sliding friction may result. If the bore fits too loosely around the o-ring, then excessive air leakage may result. By using the bellows in place of the o-ring, the manufacturing tolerances in the bore can be relaxed, with the result that manufacturing costs will be reduced and fewer parts will be rejected. The bellows 89 is preferably made of a material having sufficient stiffness and sufficient flexibility so that the bellows can perform the following functions: (1) act as a seal; (2) resist radial collapse under pressure; (3) allow the lancing assembly to retract to its initial pre-thrust position after the thrusting step; and (4) have its force overcome by differential gas pressure during operation.

The vacuum pump 14 is connected to the lancing assembly 16 by an evacuation tube 24. The air that is evacuated from the lancing assembly 16 by the vacuum pump 14 is removed via the evacuation tube 24. The evacuation tube 24 is typically made from a polymeric material. A check valve 26 is placed between the vacuum pump 14 and the lancing assembly 16 at a point in the evacuation tube 24 to prevent air removed from the lancing assembly 16 by the vacuum pump 14 from flowing back to the lancing assembly 16 and adversely affecting the vacuum.

A source of power for the vacuum pump 14 can be disposed within the housing 12. A source of power suitable for the device of this invention is a battery 18. Alternatively, an external source of power can be used to operate the vacuum pump 14. The power source is actuated by the electronics 20, which, in turn, is actuated by the switch 22.

The electronics 20 may incorporate a microprocessor or microcontroller. The function of the electronics 20 is to switch power on and off to operate the various components in the apparatus. These components include, but are not limited to, the vacuum pump 14. The electronics 20 can also be use to switch power on and off to operate components in alternative embodiments, e. g., heating elements, lancets, indicating devices, and valves. Electronics suitable for this invention is the "TATTLETALE MODEL 5F" controller/ data logger, commercially available from Onset Computer Corporation, 536 MacArthur Blvd. P. O. Box 3450, Pocasset, Mass. 02559-3450. Auxiliary electronic devices, such as power transistors, pressure monitors, and OP-Amps (operational amplifiers), may also be required in order to provide an interface between the controller and the operational components. All electronics required for this invention are well-known to one of ordinary skill in the art and are commercially available. Auxiliary electronic devices suitable for use in this invention include the following components:

| Component | Source | Catalog Number |
|---|---|---|
| Mosfet Drivers | International Rectifier El Segundo, CA | IRLD024 |
| Op-Amp | National Semiconductor Santa Clara, CA | LM358 |
| Status LED | Hewlett-Packard Newark Electronics Schaumburg, IL | HLMPD150 |
| Pressure Sensor | Sensym, Inc. Milpitas, CA | SDX15D4 |

Figure 3:
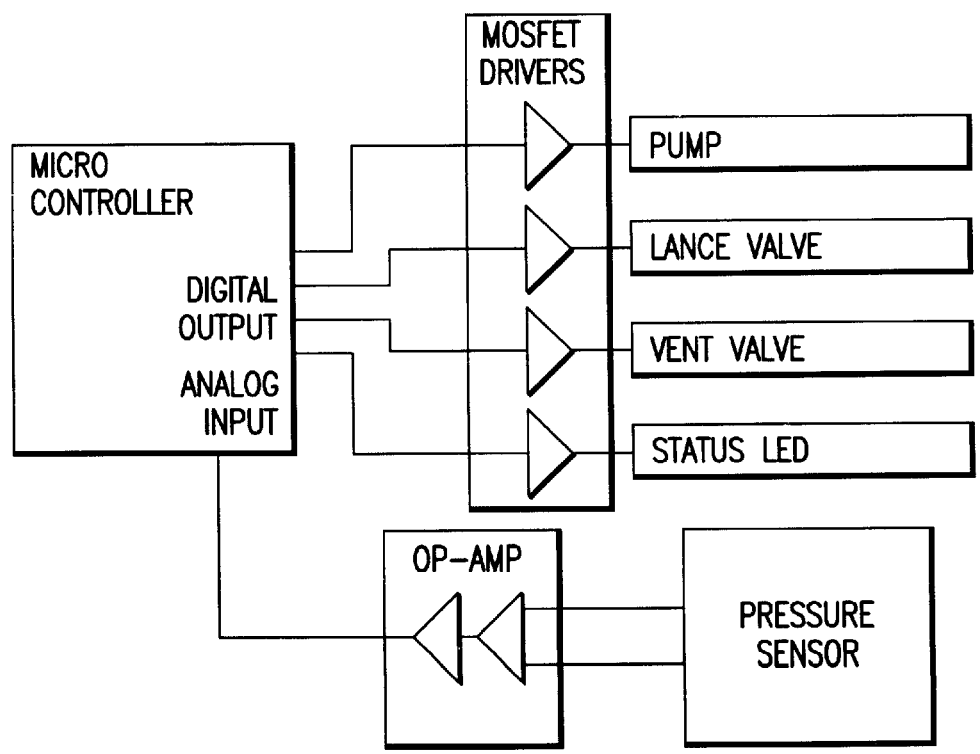
FIG. 3 is a block diagram illustrating the electronics of the preferred embodiment.

FIG. 3 illustrates by way of a block diagram how the foregoing electronic components can be arranged to carry out the method of the present invention.

Figure 2:
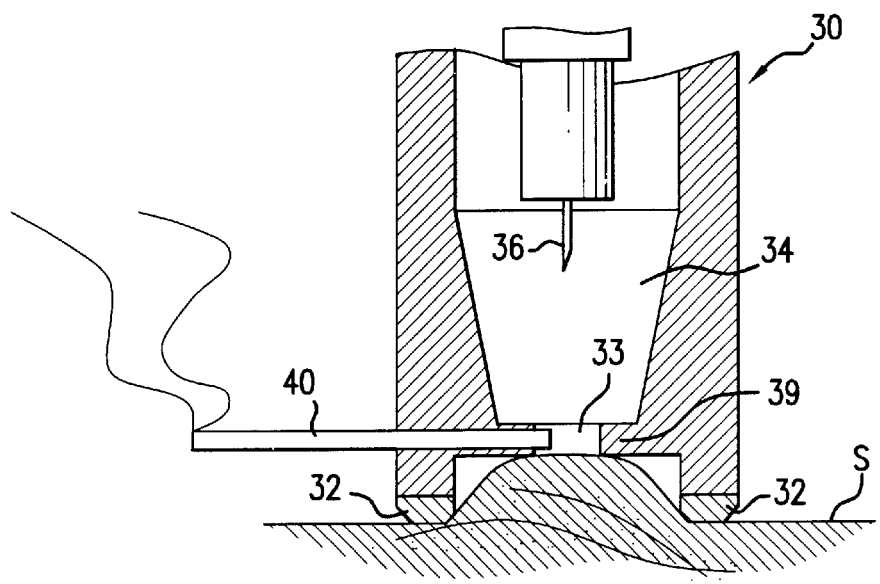
FIG. 2 is a schematic diagram illustrating how a vacuum causes a portion of the skin to become stretched prior to the formation of an opening in the skin from which the sample of blood is extracted.
Figure 4:
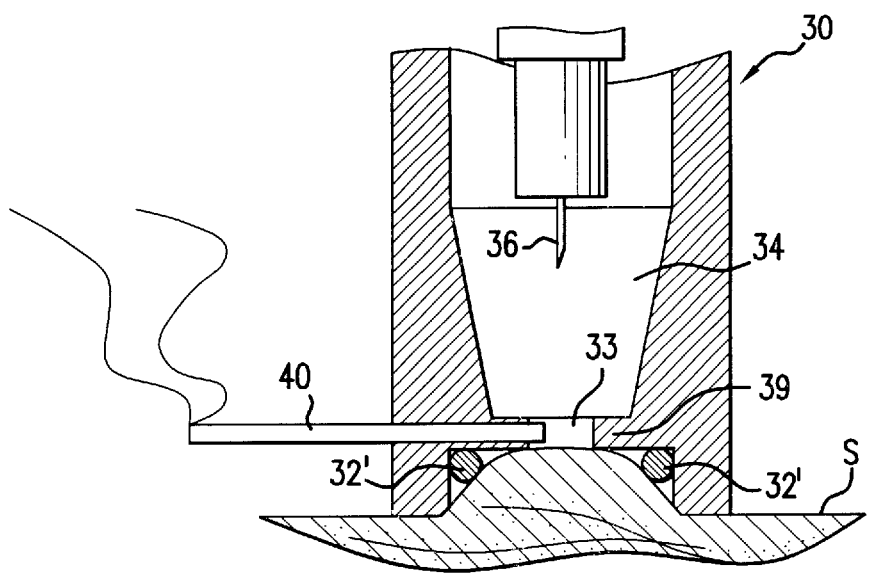
FIG. 4 is a schematic diagram illustrating an alternative seal for the vacuum of the device of the present invention.

Operation of the blood extraction device 10 will now be described. Referring now to FIGS. 1, 2 and 3, the nosepiece 30 of the lancing assembly 16 is applied to the surface of the skin, designated herein by the letter "S". The end of the nosepiece 30 that contacts the skin is equipped with a seal 32. The purpose of the seal 32 is to prevent air from leaking into blood extraction chamber 34, so that the vacuum pump 14 can provide sufficient suction action for increasing the availability of blood to the area of the skin from which the sample is to be extracted, stretching the skin, and extracting the sample of blood from the unobstructed opening in the skin. The seal 32 surrounds an opening 33 in the nosepiece 30. The opening 33 in the nosepiece allows communication between the surface of the skin and a blood extraction chamber 34 in the nosepiece 30. The seal 32 is preferably made of a rubber or an elastomeric material. FIG. 4 illustrates an alternative position for the seal 32. In FIG. 4, the seal is designated by the reference numeral 32'. The remaining parts of FIG. 4 are the same as those of FIG. 2, and, accordingly, retain the same reference numerals as were used in FIG. 2.

It has been discovered that an improved design and construction of the nosepiece 30 can provide enhanced collection of blood from the unobstructed opening in the skin. In FIG. 2, it is shown that the interior walls of the nosepiece form a shape that is essentially cylindrical. While this design is capable of providing adequate performance in the method of this invention, it has been discovered that by changing the construction of the interior cavity of the nosepiece, collection of blood can be accelerated.

A nosepiece assembly 3000 is illustrated in FIG. 26. The nosepiece assembly 3000 comprises a nosepiece 3001 and a seal 3002. The nosepiece 3001 comprises a lower base 3004 having an opening 3005 therein. Above the lower base 3004 is an upper base 3006 having an opening 3007 therein. The features of the exterior of the nosepiece, other than the lower base 3004 and the upper base 3006, are not critical to this invention, and one of ordinary skill in the art can design the exterior walls of the nosepiece in any manner that does not adversely affect the operation of the nosepiece of this invention. The features of the interior of the nosepiece, the lower base 3004, the upper base 3006, and, in some cases, the seal 3002 are critical and, consequently, they will be described in greater detail. An interior wall 3008 encloses a cavity 3010 of the nosepiece 3001. It is critical that the interior wall 3008 of the nosepiece 3001 be structured in such a manner that the opening 3007 in the upper base 3006 be of an equal or smaller area than the opening 3005 in the lower base 3004. It is desired that the area of the opening 3007 be reduced to as small of a size as possible, but not so small as to interfere with the collection of blood by a glucose monitor (see FIG. 2) or with the path of a lancet. An optional rim 3012 can surround the opening 3007 in the upper base 3006.

There are several ways of causing the area of the opening 3007 to be less than the area of the opening 3005. As shown in FIG. 26, the interior wall 3008 can be tapered so as to bring about a reduction in the area of the opening 3007. The tapering can begin at any point along the interior wall 3008 of the nosepiece 3001. If the tapered portion runs all the way from the beginning of the tapered portion to the upper base 3006, the optional rim 3012 will have a depth of zero, and thus be eliminated from the nosepiece. Alternatively, the area of the opening 3007 can merely be made smaller than the area of the opening 3005, such as through the use of step-wise cylindrical sections.

Ports 3014 and 3016 can be included in the nosepiece 3001 to give the cavity 3010 more exposure to a vacuum, if needed.

In order to more accurately describe the construction of the nosepiece assembly 3000, reference points, designated by alphabetical letters, have been placed on FIG. 26 so that typical distances between these reference points can be disclosed. The optional rim 3012 has a depth designated by the line "ab". This depth typically ranges from 0 to about 1.5 mm, preferably from 0 to about 1.0 mm. The opening 3007 in the upper base 3006 has a major dimension designated by the line "cd". The area of the opening 3007 typically ranges from about 1 to about 500 mm$^2$, preferably from about 1 to about 150 mm$^2$. The opening 3005 in the lower base 3004 has a major dimension designated by the line "ef". The area of the opening 3005 typically ranges from about 10 to about 500 mm$^2$, preferably from about 50 to about 150 mm$^2$. The distance from the lowermost point of the rim 3012 to to lowermost point of the seal 3002 (hereinafter "rim-to-seal distance") is designated by the line "bg" This distance typically ranges from about 1.5 to about 8.0 mm, preferably from about 3 to about 6 mm. It is preferred that the distance be selected so that the skin, when stretched into the nosepiece 3001, comes as close as possible to the rim 3012 or the upper base 3006 of the nosepiece 3001. If the rim 3012 is not present, the point "d" will be located at the level of the upper base 3006. The thickness of the seal 3002 is represented by the line "eh". The width of the sealing surface and the width of the sealed surface of the lower base 3004 are designated by the line "hj". One of ordinary skill in the art would have sufficient expertise to optimize the dimensions of the nosepiece without undue experimentation. Additional details regarding the nosepiece 3001 and the seal 3002 are dealt with in the examples.

This improved nosepiece has several advantages. The improved design and construction of the nosepiece can provide enhanced collection of blood from the unobstructed opening in the skin. In addition, The nosepiece brings about a better seal to the body than do the nosepieces previously used. A better seal reduces the amount of vacuum leakage, with the result that a less expensive vacuum pump can be used. In addition, the improved nosepiece allows a seal to be maintained on those individuals having excessively hairy skin.

A particularly preferred type of nosepiece may have a seal of the type shown in FIGS. 27A and 27B in cross section, referred to hereinafter as a flex seal. The flex seal contacts a larger area of skin than does a planar seal. The flex seal can then cause more skin to be brought into the internal space of the nosepiece when vacuum is applied than can a planar seal. The flex seal can be made out of a silicone, 40A durometer.

The flex seal 3020 can be attached to the nosepiece 3022 by a mechanical attachment 3024 or by an adhesive. The portion 3026 of the flex seal that is not attached to the nosepiece 3022 is capable of moving between a first position, as shown in FIG. 27A, and a second position, as shown in FIG. 27B. In the first position, the unattached portion 3026 of the flex seal 3020 depends from the lower base 3028 of the nosepiece 3022 as shown in FIGS. 27A. In the second position, the unattached portion 3026 of the flex seal 3020 contacts the lower base 3028 of the nosepiece 3022 such that one major surface of the unattached portion of the seal is in face-to-face contact with the lower base 3028 of the nosepiece as shown in FIG. 27B. The flex seal is made of a material having a coefficient of friction that reduces the tendency of skin in contact with it to slide. The seal should be sufficiently flexible so that it can move between the first position and the second position and sufficiently stiff to hold the skin in an immovable position. The opening 3030 in the flex seal has an area greater than the area of the opening 3032 in the lower base 3028 of the nosepiece 3022, when the flex seal is in the first position, as shown in FIG. 27A.

In operation, the flex seal, is placed against the skin "S" of the patient. The area of skin contacted by the flex seal is greater than the area of the opening in the lower base of the nosepiece. Consequently, the volume of skin lifted into the nosepiece is greater than the volume of skin that would have been lifted into the nosepiece with a planar seal. Thus, the flex seal would be beneficial for a patient having below normal skin flexibility.

The switch 22 is actuated, typically by being pressed, thereby activating the electronics 20, which starts the vacuum pump 14. The vacuum pump 14 then provides a suction action. The suction action of the vacuum pump 14 causes the skin circumscribed by the seal 32 to become engorged with blood. Engorgement of the skin with blood is accompanied by a stretching of and rising up of the skin up to opening 33.

After an appropriate period of time, which is typically pre-set by the programmer of the electronics, the lancing assembly 16 is triggered, thereby causing the lancet 36 to penetrate the skin that has risen up to the opening 33 and that is engorged with blood. The lancet 36 is preferably triggered automatically, by a solenoid valve 38 that causes a vacuum-actuated piston (not shown) to trigger the lancet 36. The lancet 36 is then retracted, preferably automatically. Thereupon, the blood flows out of the unobstructed opening resulting from the lancet 36, and, aided by the vacuum generated by the vacuum pump 14, is collected. When sufficient blood has been collected or a pre-set time interval has passed, the electronics 20 causes the vacuum pump 14 to stop. The device 10 can then be removed from the surface of the skin after another solenoid valve (not shown because it is hidden under solenoid valve 38) is opened to vent the vacuum to allow ease of removal of the device from the surface of the skin. Solenoid valves suitable for use with the apparatus described herein are commercially available from The Lee Company, Essex, Conn. and have the part number LHDA0511111H.

The blood is preferably directly collected on the application zone of a glucose detector, e. g., a reflectance strip or biosensor. The blood can then be used as the sample for a determination of glucose concentration in blood. Alternatively, the blood can be collected by other collection devices, such as, for example, a capillary tube or absorbent paper.

The apparatus of the present invention can include a glucose detector for analyzing the blood sample extracted by the apparatus. Glucose detectors are well-known in the art. With respect to glucose monitoring, there are two major categories of glucose detectors—reflectometers and biosensors. Representative examples of reflectometers suitable for this invention are described in U.S. Pat. No. 4,627,445, incorporated herein by reference. Representative examples of biosensors suitable for this invention are described in U.S. Pat. No. 5,509,410, incorporated herein by reference.

The glucose detector is preferably disposed in the nosepiece 30 of the lancing assembly 16. The glucose detector must be located at a position sufficiently close to the site of blood extraction so that the quantity of extracted blood collected will be sufficient to carry out a standard glucose monitoring test. Typically, this distance will preferably be no more than 5 mm from the site of blood extraction, more preferably no more than 3 mm from the site of blood extraction, most preferably no more than 1 mm from the site of blood extraction. Alternatively, the glucose detector may be maintained at a distance greater than 5 mm from the site of blood extraction until shortly after the lancet has been triggered, preferably about 50 milliseconds but at least long enough to allow the lancet to be retracted. If the glucose detector is so positioned, it may then be triggered, for example by a solenoid valve that causes a vacuum actuated piston to trigger the glucose detector. Other triggering mechanisms may also be used. The triggering action propels the glucose detector towards the skin, preferably no more than 5 mm from the site of blood extraction, more preferably no more than 3 mm from the site of blood extraction, most preferably no more than 1 mm from the site of blood extraction. Care must be taken in the placement of the glucose detector so that the detector does not adversely affect the vacuum, when a vacuum is employed to aid in the extraction of blood. In addition, the glucose detector 40 should be modified, if necessary, so that the blood collected in the collection zone of the glucose detector is capable of being used to activate the glucose detector.

FIG. 2 also illustrates a manner for disposing a glucose detector 40 in the nosepiece 30 of the lancing assembly 16.

Figure 5:
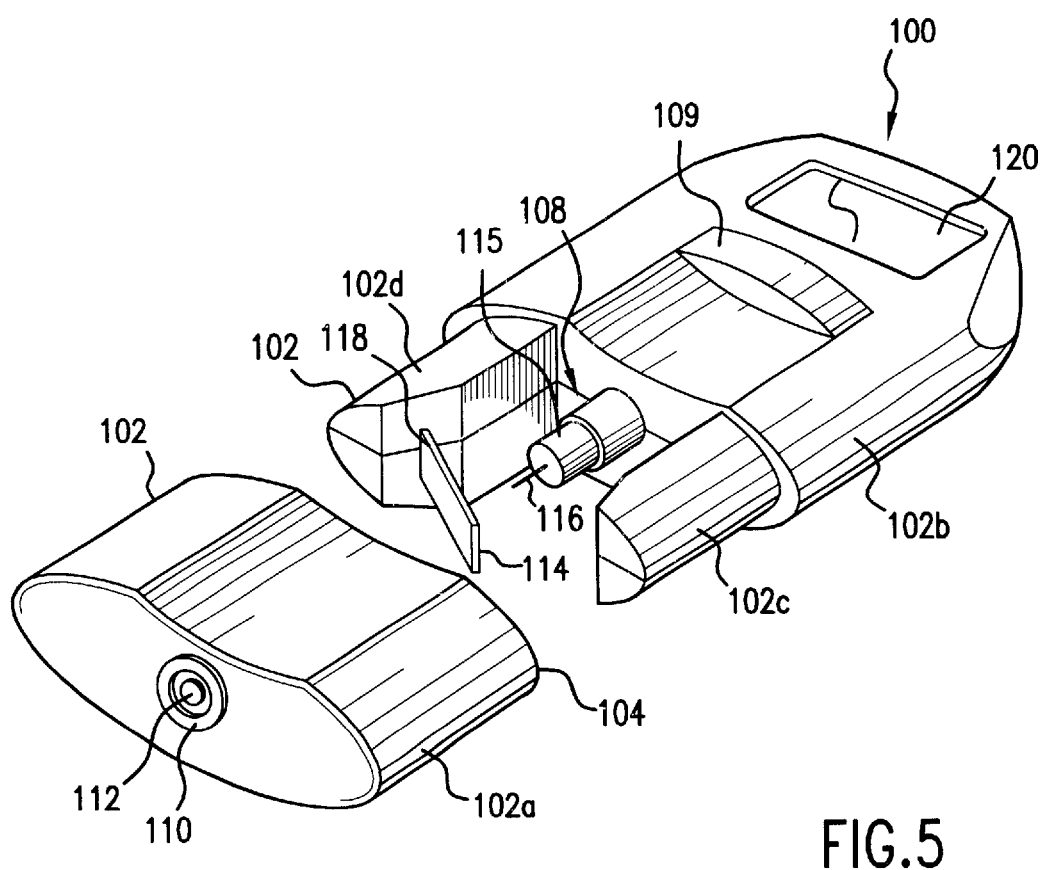
FIG. 5 is a perspective view of an embodiment of the apparatus of this invention. In this figure, the housing of the apparatus is open.

FIGS. 5–14 illustrate various alternative embodiments of the apparatus of this invention. In FIG. 5, blood extraction device 100 comprises a housing 102. The housing 102 is separable into two portions, a receiving portion 102*a* and a projecting portion 102*b*. A gasket 104 is provided to seal the portions 102*a* and 102*b* of the housing 102 and to aid in separation of the receiving portion 102*a* from the projecting portion 102*b*. The receiving portion 102*a* forms a tight fit with the projecting portion 102*b* by means of friction. Projecting elements 102*c* and 102*d* are used to guide the projecting portion 102*b* into the receiving portion 102*a*. Disposed within the housing 102 are a vacuum pump (not shown), a lancing assembly 108, a battery (not shown), and electronics (not shown). A switch 109 is provided to activate the electronics. The vacuum pump is connected to the lancing assembly 108 by an evacuation tube (not shown). A check valve (not shown) is placed between the vacuum pump and the lancing assembly 108.

During the process of obtaining the sample, the receiving portion 102*a* and the projecting portion 102*b* are fitted tightly together. The area of the receiving portion 102*a* of the housing 102 of the device 100 that is to contact the skin is equipped with a seal 110. The seal 110 surrounds an opening 112 in the receiving portion 102*a*. The opening 112 in the receiving portion 102*a* allows communication between the surface of the skin and a blood extraction chamber adjacent to a glucose detector 114, shown here in the shape of a strip. When in use, the device 100 is positioned so that the lancing assembly 108 is placed over the region on the surface of the skin from which the sample is to be obtained. In order to obtain the sample of blood, the receiving portion 102*a* of the housing 102 of the device 100 is placed against the skin, whereby the seal 110 allows a satisfactory vacuum to be effected. The switch 109 is actuated, typically by being pressed, thereby activating the electronics, which starts the vacuum pump. The vacuum pump then provides a suction action. The suction action of the vacuum pump causes the skin circumscribed by the seal 110 to become engorged with blood. Engorgement of the skin with blood is accompanied by a stretching of and rising up of the skin up to the opening 112. After an appropriate period of time, which is typically pre-set by the programmer of the electronics, the lancing assembly 108 is triggered, thereby causing the lancet 116 to penetrate the skin that has risen up to the opening 112 and that is engorged with blood. The lancet 116 is preferably triggered automatically, by a solenoid valve (not shown) that causes a vacuum-actuated piston (not shown) to trigger the lancet 116. The remaining steps of the process relating to collection of a sample of blood are substantially similar to the steps described in the embodiment shown in FIGS. 1, 2, 3, and 4.

In the embodiment shown in FIG. 5, the glucose detector 114 is inserted into a slot 118 in the projecting portion 102*b* of the housing 102. The receiving portion 102*a* of the housing 102 causes the glucose detector 114 to be moved into its proper position for testing. The results obtained from the glucose detector 114 can be displayed on a screen 120, typically a conventional liquid crystal digital display. The receiving portion 102*a* is separated from the projecting portion 102*b* when the lancet 116 or glucose detector 114 is being replaced. The receiving portion 102*a* is fitted tightly to the projecting portion 102*b* during the process of obtaining a sample of blood.

The relative positions of the vacuum pump, the battery, the electronics, the evacuation tube, the check valve, the solenoid valves, and the vacuum-actuated piston are substantially similar to the relative positions of these components as described in the embodiments shown in FIGS. 1 and 2.

Figure 6:
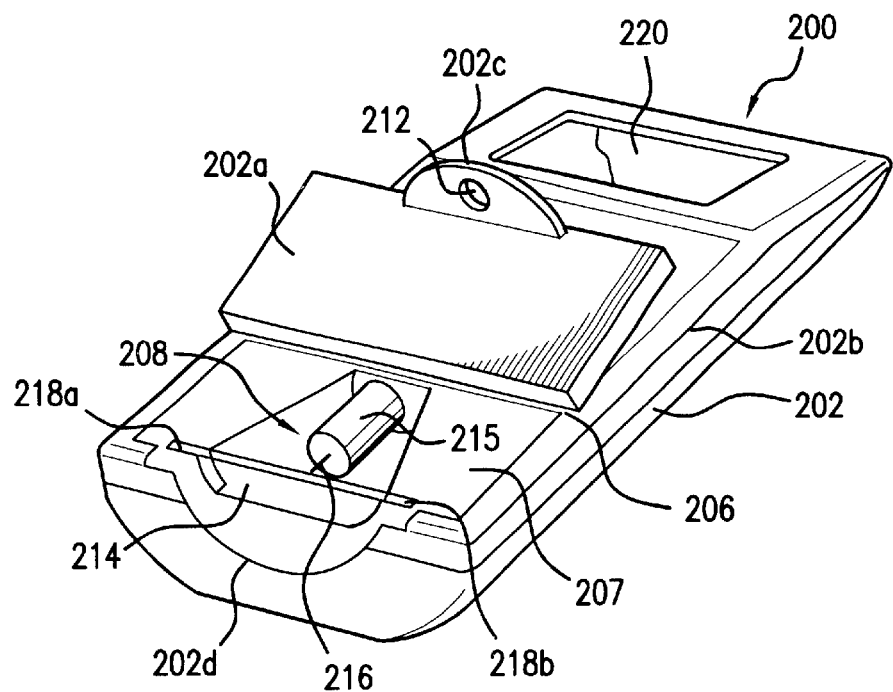
FIG. 6 is a perspective view of an embodiment of the apparatus of this invention. In this figure, the housing of the apparatus is open.

In FIG. 6, blood extraction device 200 comprises a housing 202. The housing 202 comprises a door portion 202*a* that is attached to the remaining portion 202*b* of the housing 202 by a hinge 206. A gasket 207 is provided to seal the housing 202 when the door portion 202*a* is closed. The door portion 202*a* can be closed by pivoting it around the hinge 206. When the door portion 202*a* is closed, the convex portion 202*c* of the door portion 202*a* fits precisely into the concave portion 202*d* of the remaining portion 202*b* of the housing 202. The remaining edges of the door portion 202*a* fit tightly against the remaining edges of the remaining portion 202*b* of the housing 202. Disposed within the housing 202 are a vacuum pump (not shown), a lancing assembly 208, a battery (not shown), and electronics (not shown). A switch (not shown) is provided to activate the electronics. The vacuum pump is connected to the lancing assembly 208 by an evacuation tube (not shown). A check valve (not shown) is placed between the vacuum pump and the lancing assembly 208.

During the process of obtaining the sample, the door portion 202*a* is closed. The area of the door portion 202*a* of the housing 202 of the device 200 that is to contact the skin is equipped with a seal (not shown). The seal surrounds an opening 212 in the door portion 202*a*. The opening 212 in the door portion 202*a* allows communication between the surface of the skin and a blood extraction chamber adjacent to a glucose detector 214, shown here in the shape of a strip. When in use, the device 200 is positioned so that the lancing assembly 208 is placed over the region on the surface of the skin from which the sample is to be obtained. In order to obtain the sample of blood, the door portion 202*a* of the housing 202 of the device 200 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 212. After an appropriate period of time, which is typically pre-set by the programmer of the electronics, the lancing assembly 208 is triggered, thereby causing the lancet 216 to penetrate the skin that has risen up to the opening 212 and that is engorged with blood. The lancet 216 is preferably triggered automatically, by a solenoid valve (not shown) that causes a vacuum-actuated piston (not shown) to trigger the lancet 216. The remaining steps of the process relating to collection of a sample of blood are substantially similar to the steps described in the embodiment shown in FIGS. 1, 2, 3, and 4.

In the embodiment shown in FIG. 6, the glucose detector 214 is inserted into slots 218*a* and 218*b* of the housing 202. The results obtained from the glucose detector 214 can be displayed on screen 220, typically a conventional liquid crystal digital display. The door portion 202*a* is opened when the lancet 216 or glucose detector 214 is being replaced. The door portion 202*a* is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 7:
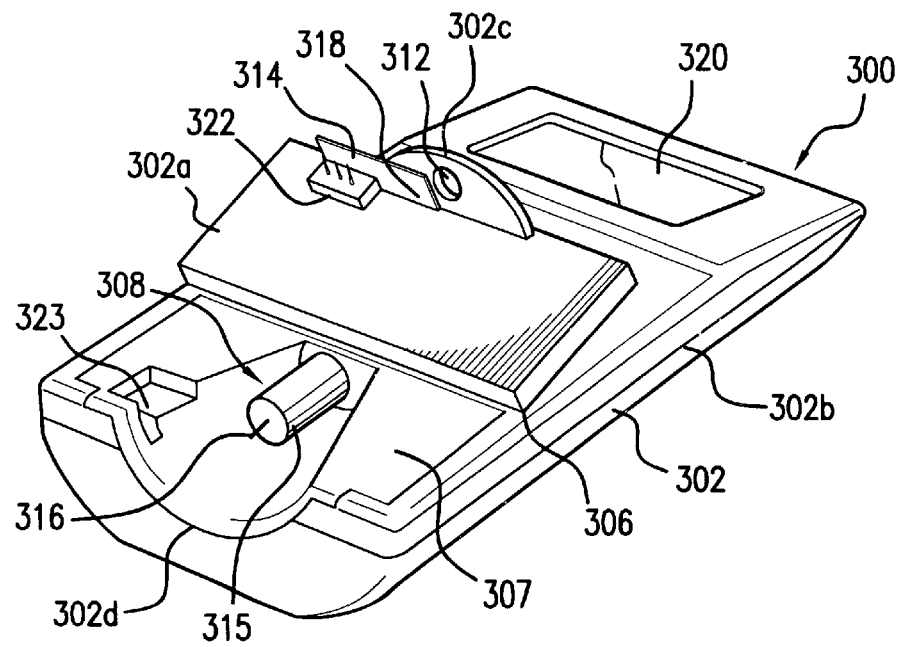
FIG. 7 is a perspective view of an embodiment of the apparatus of this invention. In this figure, the housing of the apparatus is open.

In FIG. 7, blood extraction device 300 comprises a housing 302. The housing 302 comprises a door portion 302*a* that is attached to the remaining portion 302*b* of the housing 302 by a hinge 306. A gasket 307 is provided to seal the housing 302 when the door portion 302*a* is closed. The door portion 302*a* can be closed by pivoting it around the hinge 306. When the door portion 302*a* is closed, the convex portion 302*c* of the door portion 302*a* fits precisely into the concave portion 302*d* of the remaining portion 302*b* of the housing 302. The remaining edges of the door portion 302*a* fit tightly against the remaining edges of the remaining portion 302*b* of the housing 302. Disposed within the housing 302 are a vacuum pump (not shown), a lancing assembly 308, a battery (not shown), and electronics (not shown). A switch (not shown) is provided to activate the electronics. The vacuum pump is connected to the lancing assembly 308 by an evacuation tube (not shown). A check valve (not shown) is placed between the vacuum pump and the lancing assembly 308.

During the process of obtaining the sample, the door portion 302*a* is closed. The area of the door portion 302*a* of the housing 302 of the device 300 that is to contact the skin is equipped with a seal (not shown). The seal surrounds an opening 312 in the door portion 302*a*. The opening 312 in the door portion 302*a* allows communication between the surface of the skin and a blood extraction chamber adjacent to a glucose detector 314, shown here in the shape of a strip. When in use, the device 300 is positioned so that the lancing assembly 308 is placed over the region on the surface of the skin from which the sample is to be obtained. In order to obtain the sample of blood, the door portion 302*a* of the housing 302 of the device 300 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 312. After an appropriate period of time, which is typically pre-set by the programmer of the electronics, the lancing assembly 308 is triggered, thereby causing the lancet 316 to penetrate the skin that has risen up to the opening 312 and that is engorged with blood. The lancet 316 is preferably triggered automatically, by a solenoid valve (not shown) that causes a vacuum-actuated piston (not shown) to trigger the lancet 316. The remaining steps of the process relating to collection of a sample of blood are substantially similar to the steps described in the embodiment shown in FIGS. 1, 2, 3, and 4.

In the embodiment shown in FIG. 7, the glucose detector 314 is inserted into a slot 318 of the housing 302. The results obtained from the glucose detector 314 can be displayed on screen 320, typically a conventional liquid crystal digital display. In FIG. 7, connections 322 for the electronics are shown. The door portion 302*a* is opened when the lancet 316 or glucose detector 314 is being replaced. The door portion 302*a* is closed during the process of obtaining a sample of blood.

The relative positions of the vacuum pump, the battery, the electronics, the switch, the evacuation tube, the check valve, the seal, the solenoid valves, and the vacuum-actuated piston are substantially similar to the relative positions of these components as described in the embodiments shown in FIGS. 1 and 2.

Figure 8:
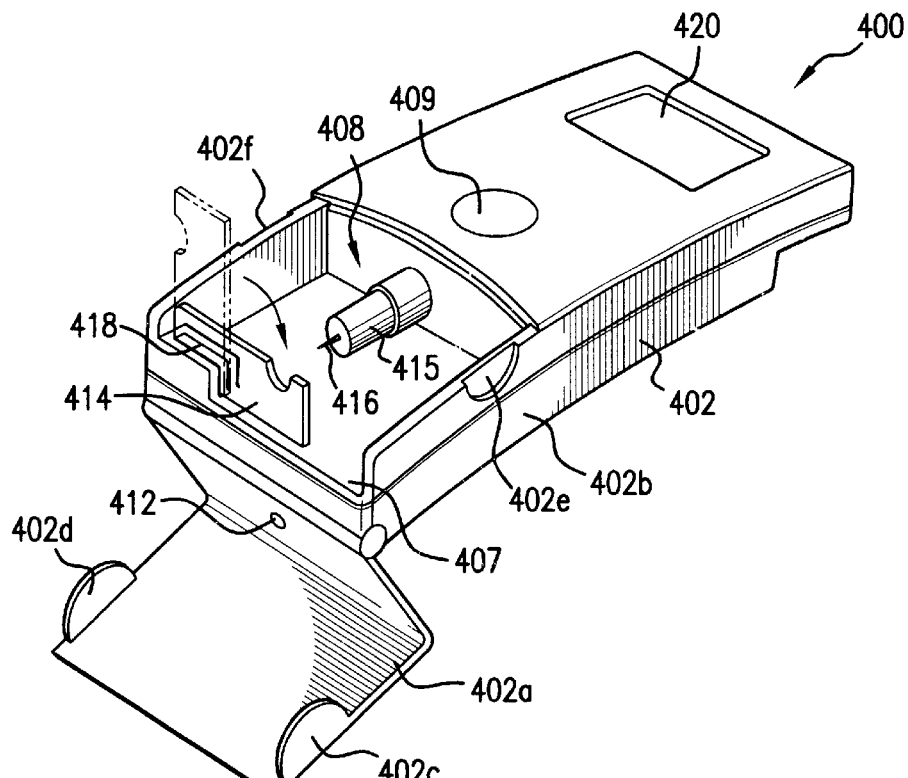
FIG. 8 is a perspective view of an embodiment of the apparatus of this invention. In this figure, the housing of the apparatus is open.

In FIG. 8, blood extraction device 400 comprises a housing 402. The housing 402 comprises a door portion 402*a* that is attached to the remaining portion 402*b* of the housing 402 by a hinge 406. A gasket 407 is provided to seal the housing 402 when the door portion 402*a* is closed. The door portion 402*a* can be closed by pivoting it around the hinge 406. When the door portion 402*a* is closed, the convex portions 402*c* and 402*d* of the door portion 402*a* fit precisely into the concave portions 402*e* and 402*f*, respectively, of the remaining portion 402*b* of the housing 402. The remaining edges of the door portion 402*a* fit tightly against the remaining edges of the remaining portion 402*b* of the housing 402. Disposed within the housing 402 are a vacuum pump (not shown), a lancing assembly 408, a battery (not shown), and electronics (not shown). A switch 409 is provided to activate the electronics. The vacuum pump is connected to the lancing assembly 408 by an evacuation tube (not shown). A check valve (not shown) is placed between the vacuum pump and the lancing assembly 408.

During the process of obtaining the sample, the door portion 402*a* is closed. The area of the door portion 402*a* of the housing 402 of the device 400 that is to contact the skin is equipped with a seal (not shown). The seal surrounds an opening 412 in the door portion 402*a*. The opening 412 in the door portion 402*a* allows communication between the surface of the skin and a blood extraction chamber adjacent to a glucose detector 414, shown here in the shape of a strip. When in use, the device 400 is positioned so that the lancing assembly 408 is placed over the region on the surface of the skin from which the sample is to be obtained. In order to obtain the sample of blood, the door portion 402*a* of the housing 402 of the device 400 is placed against the skin, whereby the seal allows a satisfactory vacuum to be effected. The switch 409 is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 412. After an appropriate period of time, which is typically pre-set by the programmer of the electronics, the lancing assembly 408 is triggered, thereby causing the lancet 416 to penetrate the skin that has risen up to the opening 412 and that is engorged with blood. The lancet 416 is preferably triggered automatically, by a solenoid valve (not shown) that causes a vacuum-actuated piston (not shown) to trigger the lancet 416. The remaining steps of the process relating to collection of a sample of blood are substantially similar to the steps described in the embodiment shown in FIGS. 1, 2, 3, and 4.

In the embodiment shown in FIG. 8, the glucose detector 414 is inserted into a slot 418 of the housing 402. In this embodiment, it is shown that glucose detector 14 can be rotated 90° between two positions to simplify insertion and replacement thereof. The results obtained from the glucose detector 414 can be displayed on screen 420, typically a conventional liquid crystal digital display. The door portion 402a is opened when the lancet 416 or glucose detector 414 is being replaced. The door portion 402a is closed during the process of obtaining a sample of blood.

The relative positions of the vacuum pump, the battery, the electronics, the evacuation tube, the check valve, the seal, the solenoid valves, and the vacuum-actuated piston are substantially similar to the relative positions of these components as described in the embodiments shown in FIGS. 1 and 2.

Figure 9:
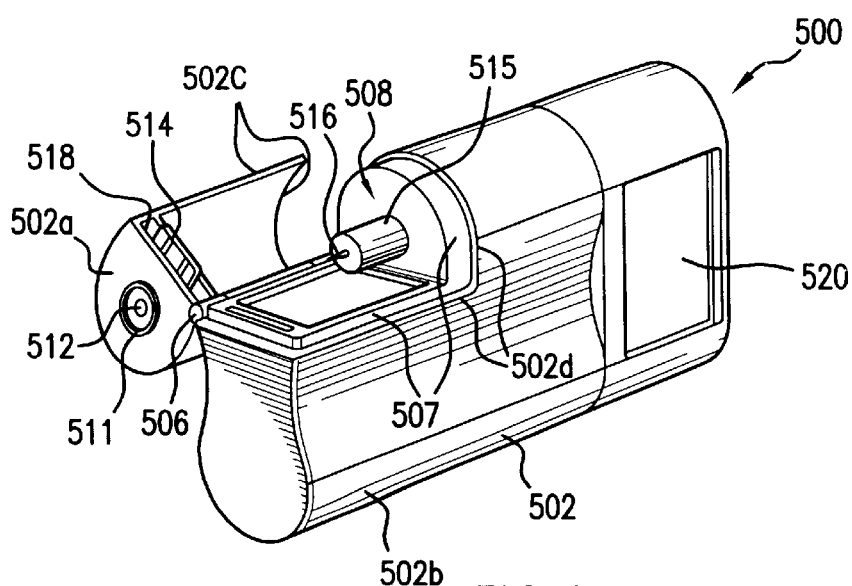
FIG. 9 is a perspective view of an embodiment of the apparatus of this invention. In this figure, the housing of the apparatus is open.

In FIG. 9, blood extraction device 500 comprises a housing 502. The housing 502 comprises a cover portion 502a that is attached to the remaining portion 502b of the housing 502 by a hinge 506. A gasket 507 is provided to seal the housing 502 when the cover portion 502a is closed. The cover portion 502a can be closed by pivoting it around the hinge 506. When the cover portion 502a is closed, edges 502c of the cover portion 502a tightly fit against edges 502d of the remaining portion 502b of the housing 502. Disposed within the housing 502 are a vacuum pump (not shown), a lancing assembly 508, a battery (not shown), and electronics (not shown). A switch (not shown) is provided to activate the electronics. The vacuum pump is connected to the lancing assembly 508 by an evacuation tube (not shown). A check valve (not shown) is placed between the vacuum pump and the lancing assembly 508.

During the process of obtaining the sample, the cover portion 502a is closed. The cover portion 502a of the housing 502 of the device 500 that is to contact the skin is equipped with a seal 511. The seal 511 surrounds an opening 512 in the cover portion 502a. The opening 512 in the cover portion 502a allows communication between the surface of the skin and a blood extraction chamber adjacent to a glucose detector 514, shown here in the shape of a strip. When in use, the device 500 is positioned so that the lancing assembly 508 is placed over the region on the surface of the skin from which the sample is to be obtained. In order to obtain the sample of blood, the cover portion 502a of the housing 502 of the device 500 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 512. After an appropriate period of time, which is typically pre-set by the programmer of the electronics, the lancing assembly 508 is triggered, thereby causing the lancet 516 to penetrate the skin that has risen up to the opening 512 and that is engorged with blood. The lancet 516 is preferably triggered automatically, by a solenoid valve (not shown) that causes a vacuum-actuated piston (not shown) to trigger the lancet 516. The remaining steps of the process relating to collection of a sample of blood are substantially similar to the steps described in the embodiment shown in FIGS. 1, 2, 3, and 4.

In the embodiment shown in FIG. 9, the glucose detector 514 is inserted into a slot 518 of the housing 502. The results obtained from the glucose detector 514 can be displayed on screen 520, typically a conventional liquid crystal digital display. The cover portion 502a is opened when the lancet 516 or glucose detector 514 is being replaced. The cover portion 502a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

Figure 10:
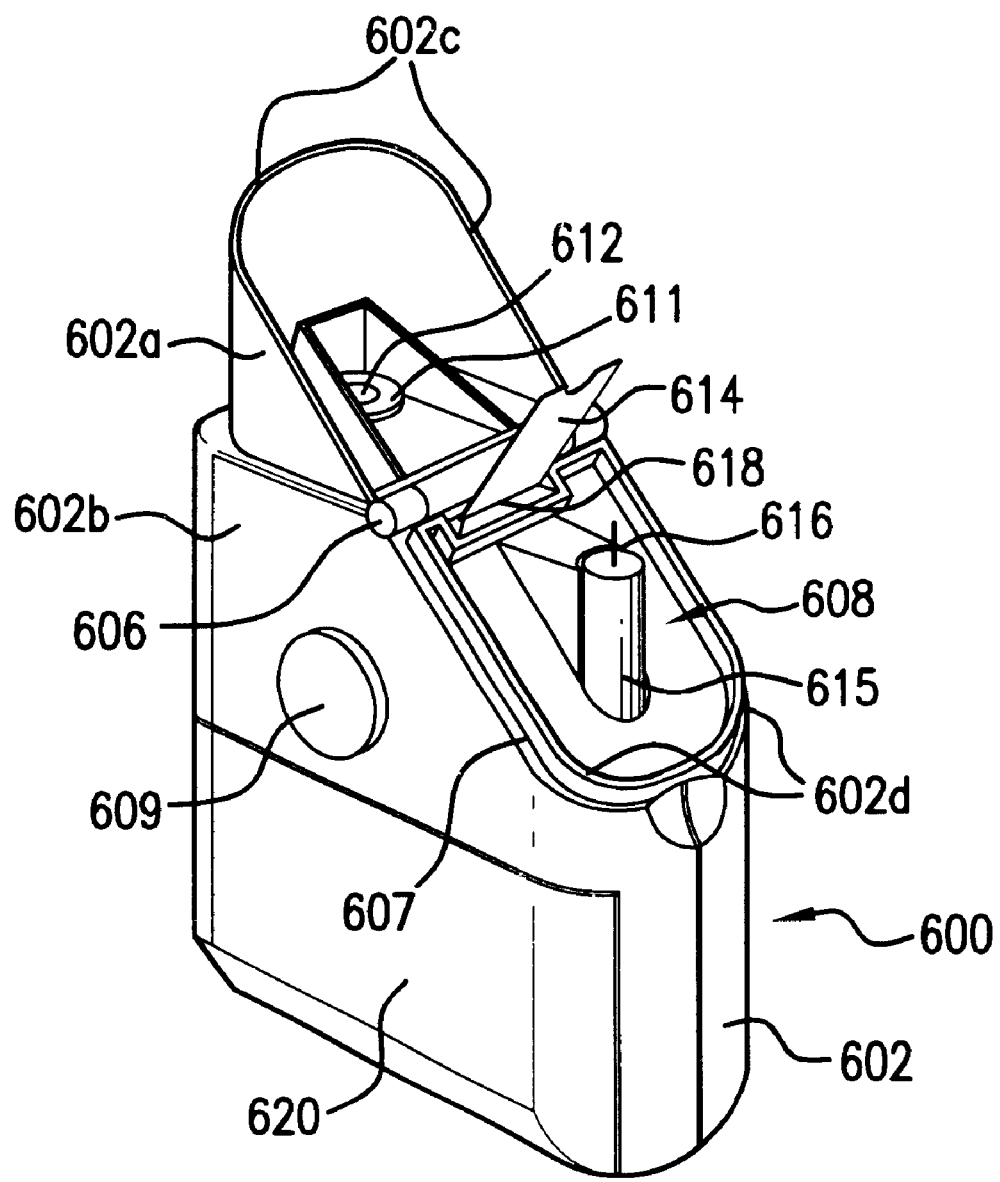
FIG. 10 is a perspective view of an embodiment of the apparatus of this invention. In this figure, the housing of the apparatus is open.

In FIG. 10, blood extraction device 600 comprises a housing 602. The housing 602 comprises a cover portion 602a that is attached to the remaining portion 602b of the housing 602 by a hinge 606. A gasket 607 is provided to seal the housing 602 when the cover portion 602a is closed. The cover portion 602a can be closed by pivoting it around the hinge 606. When the cover portion 602a is closed, edges 602c of the cover portion 602a tightly fit against edges 602d of the remaining portion 602b of the housing 602. Disposed within the housing 602 are a vacuum pump (not shown), a lancing assembly 608, a battery (not shown), and electronics (not shown). A switch 609 is provided to activate the electronics. The vacuum pump is connected to the lancing assembly 608 by an evacuation tube (not shown). A check valve (not shown) is placed between the vacuum pump and the lancing assembly 608.

During the process of obtaining the sample, the cover portion 602a is closed. The cover portion 602a of the housing 602 of the device 600 that contacts the skin is equipped with a seal 611. The seal 611 surrounds an opening 612 in the cover portion 602a. The opening 612 in the cover portion 602a allows communication between the surface of the skin and a blood extraction chamber adjacent to a glucose detector 614, shown here in the shape of a strip. When in use, the device 600 is positioned so that the lancing assembly 608 is placed over the region on the surface of the skin from which the sample is to be obtained. In order to obtain the sample of blood, the cover portion 602a of the housing 602 of the device 600 is placed against the skin, whereby the seal allows a satisfactory vacuum to be effected. The switch is actuated, typically by being pressed, thereby activating the electronics, which starts the vacuum pump. The vacuum pump then provides a suction action. The suction action of the vacuum pump causes the skin circumscribed by the seal to become engorged with blood. Engorgement of the skin with blood is accompanied by a stretching of and rising up of the skin up to the opening 612. After an appropriate period of time, which is typically pre-set by the programmer of the electronics, the lancing assembly 608 is triggered, thereby causing the lancet 616 to penetrate the skin that has risen up to the opening 612 and that is engorged with blood. The lancet 616 is preferably triggered automatically, by a solenoid valve (not shown) that causes a vacuum-actuated piston (not shown) to trigger the lancet 616. The remaining steps of the process relating to collection of a sample of blood are substantially similar to the steps described in the embodiment shown in FIGS. 1, 2, 3, and 4.

In the embodiment shown in FIG. 10, the glucose detector 614 is inserted into a slot 618 of the housing 602. The results obtained from the glucose detector 614 can be displayed on screen 620, typically a conventional liquid crystal digital display. The cover portion 602a is opened when the lancet 616 or glucose detector 614 is being replaced. The cover portion 602a is closed during the process of obtaining a sample of blood.

The relative positions of the vacuum pump, the battery, the electronics, the switch, the evacuation tube, the check valve, the solenoid valves, and the vacuum-actuated piston are substantially similar to the relative positions of these components as described in the embodiments shown in FIGS. 1 and 2.

Figure 11A:
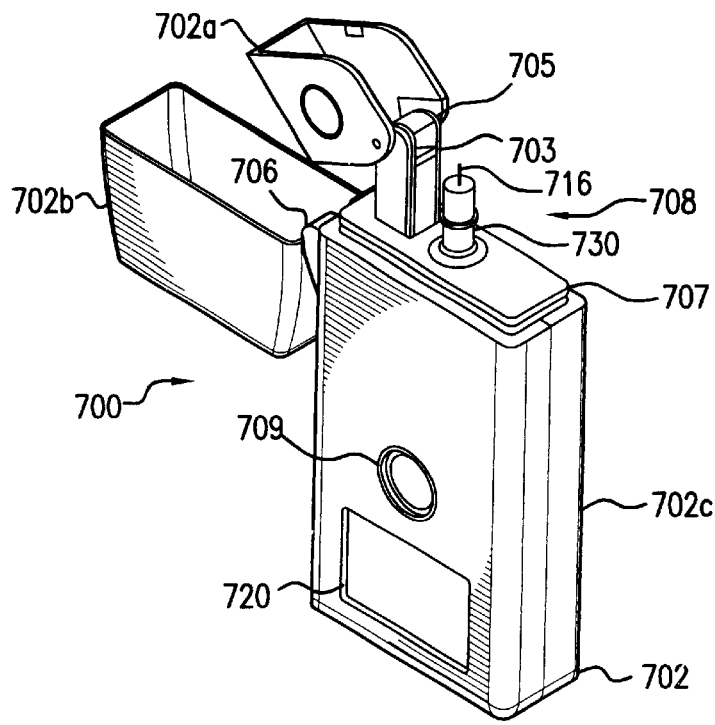
FIGS. 11A through 11C, depicts a perspective view of an embodiment of the apparatus of this invention.
Figure 11B:
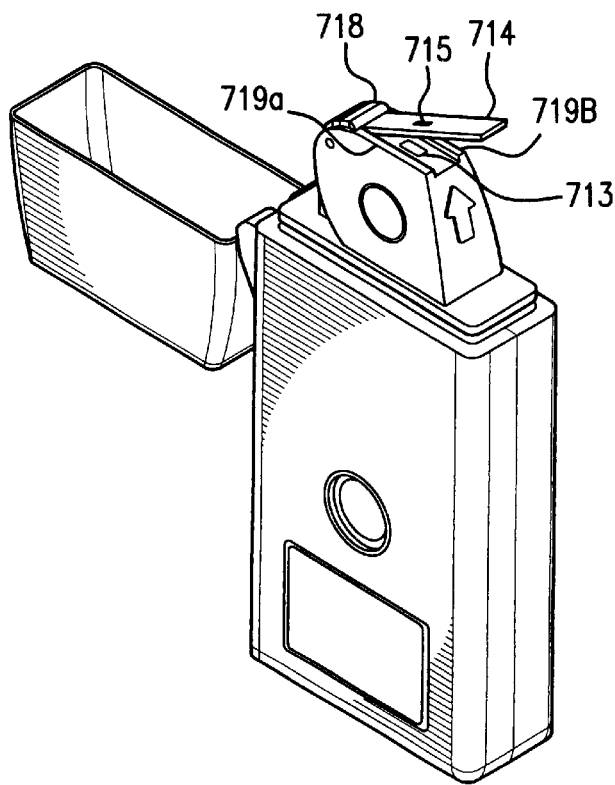
Figure 11C:
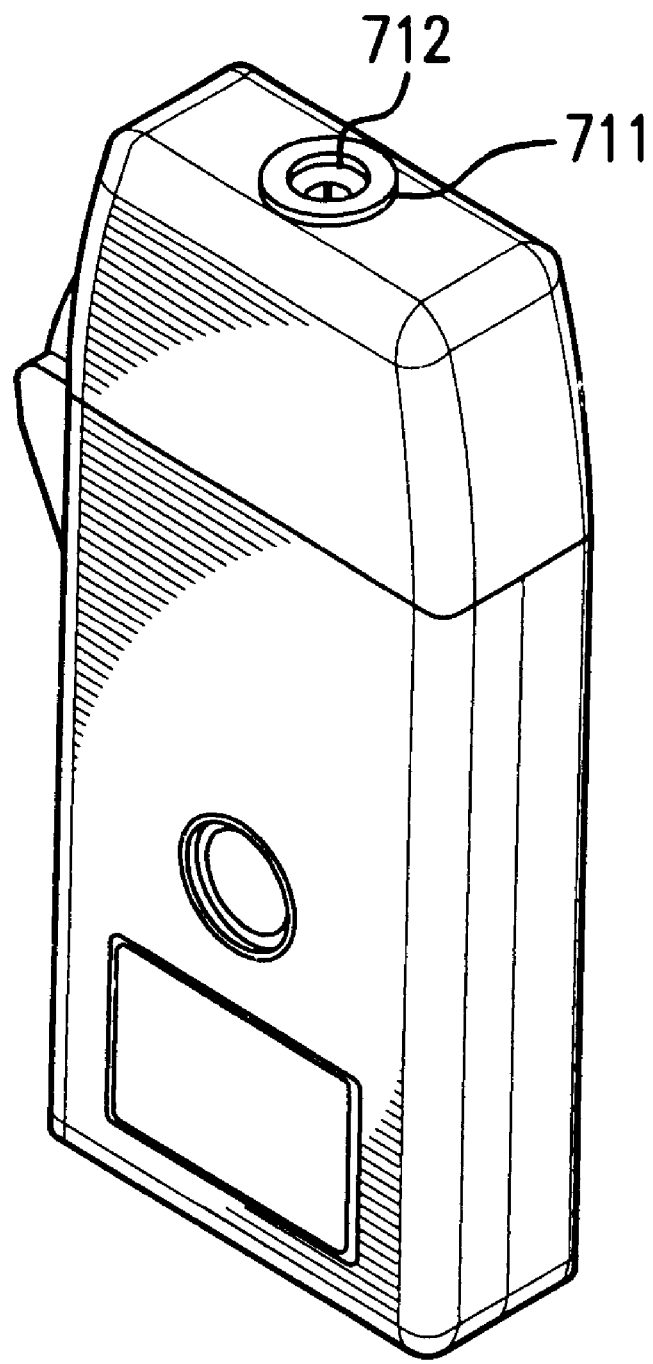

Referring now to FIGS. 11A through 11C, which depict another embodiment of the present invention, blood extraction device 700 comprises a housing 702 having an interior cover portion 702a (shown in the open position in FIG. 11A and in the closed position in FIG. 11B), a door portion 702b (shown in the open position in FIGS. 11A and 11B and in the closed position in FIG. 11C), and a body portion 702c. The interior cover portion 702a advantageously may be positioned, via projection 703, above the body portion 702c by an attachment in the form of hinge 705. Alternatively the interior cover portion 702a may be attached to the body portion 702c by frictional engagement, a detent (not shown), or any combination of a hinge 705, frictional engagement, and a detent. When a hinge 705 is used, it may optionally be spring biased to retain the interior cover portion 702a in the open or closed position. A detent (not shown) may be provided on the interior cover portion 702a to engage with a protrusion (not shown) on the projection 703, or vice versa, to maintain the interior cover portion 702a in the open or closed position when desired. Although a hinge 705 is provided in the embodiment shown in FIGS. 11A through 11C, any other attachment or combination of attachments that allows the interior cover portion 702a to attach to the body portion 702c and alternate between an open and closed position is acceptable. The door portion 702b is attached to the body portion 702c of the housing 702 by a hinge 706. Alternatively, the door portion 702b may be attached to the body portion 702c by frictional engagement, a detent, or any combination of a hinge 706, frictional engagement, and a detent. When a hinge 706 is used, it may optionally be spring biased to retain the door portion 702b in the open or closed position. A detent (not shown) may be provided on the door portion 702b to engage with a protrusion (not shown) on the body portion 702c, or vice versa, to maintain the door portion 702b in the open or closed position when desired. Although a hinge 706 is provided in the embodiment shown in FIGS. 11A through 11C, any other attachment or combination of attachments that allows the door portion 702b to attach to the body portion 702c and alternate between an open and closed position is acceptable. A gasket or other seal arrangement 707 is provided to seal the housing 702 when the interior cover portion 702a and the door portion 702b are closed. Additionally, a latch mechanism (not shown) may be provided to prevent accidental opening of the door portion 702b when the device 700 is in use. Typically, the latch mechanism would provide locking engagement of the door portion 702b with the body portion 702c.

Disposed within the housing 702 are a vacuum pump (not shown), a lancet assembly 708 generally comprising a molded plastic piece 730 to which a lancet 716 is affixed, a lancing assembly (not shown) into which the lancet assembly 708 is inserted, a battery (not shown), and electronics (not shown) for purposes described hereinafter. A switch 709 is provided to activate the electronics, which may take the form shown in FIG. 3. The vacuum pump communicates by an evacuation tube (not shown) with the volume enclosed by the door portion 702b when the door portion 702b is in the closed position. Optionally, a check valve (not shown) may be placed in the evacuation tube between the vacuum pump and the volume enclosed by the door portion 702b when the door portion 702b is in the closed position.

During the process of obtaining the sample, the interior cover portion 702a and the door portion 702b are closed together with the body portion 702c to form a seal. The seal should be sufficiently tight so that a sufficient vacuum can be obtained by removing air from the volume enclosed by the door portion 702b when the door portion 702b is in the closed position.

When the interior cover portion 702a is closed, the lancet 716 is fully enclosed within the interior cover portion 702a, thus preventing the individual being tested from accidentally coming into contact with the lancet 716. The interior cover portion 702a contains an opening 713, FIG. 11B that allows the lance 716 to extend therethrough and contact the skin as described hereinafter. The opening 713 may be round, oval, rectangular or any other shape. The interior cover portion 702a may also contain a shoulder portion (not shown) on the interior of the interior cover portion 702a that surrounds all or a portion of the opening 713. When preferably included, the shoulder portion stops the lancet assembly 708 from extending beyond the shoulder portion and prevents the lancet 716 from extending more than is desired into the skin. The preferred lancing depth typically ranges from about 0.5 mm to about 3 mm into the skin.

The area of the door portion 702b of the housing 702 that is to contact the skin is equipped with a seal 711, FIG. 11C. The seal 711 surrounds an opening 712 in the door portion 702b that aligns with the opening 713 in the interior cover portion 702a when both the interior cover portion 702a and the door portion 702b are in the closed position, as disclosed in co-pending application entitled METHOD AND APPARATUS FOR OBTAINING BLOOD FOR DIAGNOSTIC TESTS, Ser. No. 08/982,324. The opening 712 may be round, oval, rectangular or any other shape. The opening 712 in the door portion 702b allows communication between the surface of the skin and a blood extraction chamber adjacent to a fluid collector, shown here in the form of a glucose detector 714, FIG. 11B, which may take the shape of a strip. Other types of fluid collectors may also be used, and those of skill in the art will recognize that the present embodiment could easily be modified to include more than one fluid collector. Preferably, the glucose detector 714 used in the embodiment shown in FIGS. 11A through 11C contains a opening 715 in approximately the middle of glucose detector 714 for the lancet 716 to pass through, as disclosed in co-pending application entitled METHOD AND APPARATUS FOR OBTAINING BLOOD FOR DIAGNOSTIC TESTS, Ser. No. 08/982,323. The opening 715 is preferably in alignment with openings 712 and 713 and the lancet 716. The opening 715 may be covered with a mesh.

When in use, the device 700 is positioned so that the lancing assembly is placed over the region on the surface of the skin from which the fluid sample is to be obtained such that the lancing assembly is approximately perpendicular to the surface of the skin. In order to obtain the sample of blood, the door portion 702b of the housing 702 is placed against the skin, whereby the seal 711 surrounding opening 712 allows a satisfactory vacuum to be effected. The switch 709 is actuated, typically by being pressed, thereby activating the electronics, described in FIG. 3 and discussed above, which starts the vacuum pump. The action of the vacuum pump withdraws air from the volume enclosed by the door portion 702b when the door position 702b is in the closed position and causes the skin circumscribed by the seal 711 to be drawn toward the opening 712. This results in the skin becoming engorged with blood. Engorgement of the skin with blood is accompanied by a stretching of and rising up of the skin to the opening 712 in the door portion 702b.

After an appropriate period of time, which is typically pre-set by the programmed electronics, the lancing assembly is triggered, thereby causing the lancet 716 to penetrate the skin that has been pulled up into the opening 712 of the door portion 702b. The lancet 716 is preferably triggered automatically by activation of a solenoid valve (not shown) that causes a vacuum-actuated piston (not shown) to trigger the lancet 716, as disclosed in co-pending application entitled METHOD AND APPARATUS FOR OBTAINING BLOOD FOR DIAGNOSTIC TESTS Ser. No. 08/982,561. The remaining steps of the process relating to collection of a sample of blood are substantially similar to the steps described when using the embodiment shown in FIGS. 1 through 4.

In the embodiment shown in FIGS. 11A through 11C, the glucose detector 714 is inserted into a slot 718 of the projection 703 of the housing 702. Glucose detector 714 contains one or more electrical contacts (not shown) on the end inserted into the slot 718 which engage one or more electrical contacts (not shown) positioned within the slot 718. In the embodiment shown in FIGS. 11A through 11C, the slot 718 may be designed in such a manner that the glucose detector 714 is placed into the slot 718 at an angle that advantageously allows for easier and cleaner removal of the glucose detector 714 at the conclusion of the test. Alternatively, the slot 718 may be designed in such a manner that the glucose detector 714 is placed into the slot 718 substantially parallel to the upper surface of the interior cover portion 702a when the interior cover portion 702a is in the closed position. Alignment channels 719a and 719b on either side of the exterior of the interior cover portion 702a may be provided to align the glucose detector 714 so that the glucose detector 714 is properly aligned with the lancet 716. Alignment features (not shown) within the interior of the door portion 702b may also be provided to assist in the alignment of the glucose detector 714 over the lancet 716 when the door portion 702b is closed. Both the interior cover portion 702a and the door portion 702b are closed during the process of obtaining a sample of blood.

After the lancet 716 pierces the skin and is retracted, blood is withdrawn, under the aid of the vacuum, toward and onto the glucose detector 714. When a sufficient amount of blood has been collected, the glucose detector 714 generates a signal which results in deactivation of the vacuum pump and the vacuum is released by, for example, an electronically controlled valve. Alternatively, the vacuum pump may be stopped after a pre-set time interval. The blood collection device 700 may then be removed from the individual's skin. Thereafter, the glucose detector 714 generates a signal, as described above, indicative of glucose level, which signal is transmitted via electrical circuitry to the electronics housed in the blood collection device 700. The signal is processed by such electronics, in the manner described above, and the results obtained from the glucose detector 714 can be displayed on a screen 720, typically a conventional liquid crystal digital display. Other manners of display may also be used.

Upon completion of the measurement, the door portion 702b may be opened and the glucose detector 714 may be replaced. When it is desired to replace the lancet 716, both the door portion 702b and the interior cover 702a are opened, as described above. The lancet 716 and the glucose detector 714 may be replaced immediately after use, immediately before use, or may be replaced at any other time.

Figure 12A:
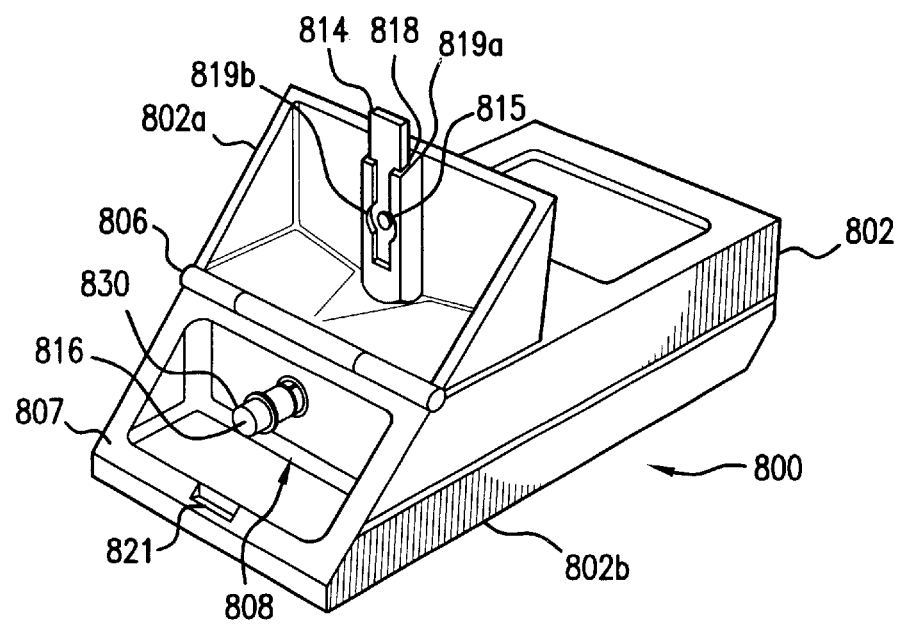
FIGS. 12A and 12B, depicts a perspective view of an embodiment of the apparatus of this invention.
Figure 12B:
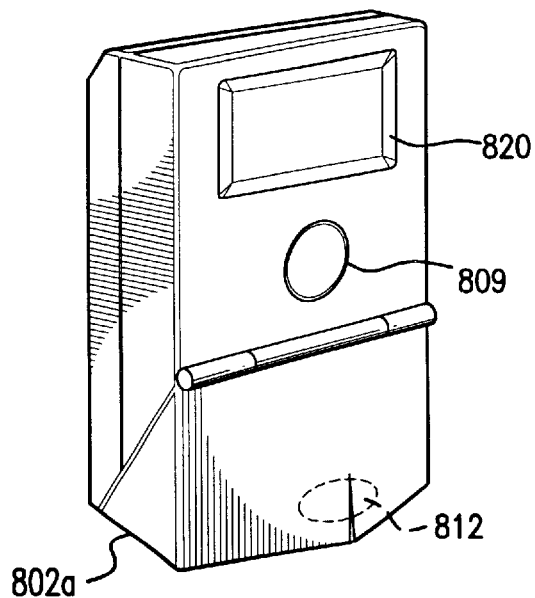

Referring now to FIGS. 12A and 12B, which depict another embodiment of the present invention, blood extraction device 800 comprises a housing 802. The housing 802 includes a door portion 802a (shown in the open position in FIG. 12A and in the closed position in FIG. 12B) that is attached to the body portion 802b of the housing 802 by an attachment in the form of a hinge 806. Alternatively, the door portion 802a may be attached to the body portion 802b by frictional engagement, a detent (not shown), or any combination of a hinge 806, frictional engagement, and a detent. When a hinge 806 is used, it may optionally be spring biased to retain the door portion 802a in the open or closed position. A detent (not shown) may be provided on the door portion 802a to engage with a protrusion (not shown) on the body portion 802b, or vice versa, to maintain the door portion 802a in the open or closed position when desired. Although a hinge 806 is provided in the embodiment shown in FIGS. 12A and 12B, any other attachment or combination of attachments that allows the door portion 802a to attach to the body portion 802b and alternate between open and closed positions is acceptable. The hinge 806 may be located on the body portion 802b as shown in FIGS. 12A and 12B or may alternatively be located on one side of the body portion 802b. A gasket or other seal arrangement 807 is provided to seal the housing 802 when the door portion 802a is closed. Additionally, a latch mechanism may be included to prevent accidental opening of the door portion 802a when the blood collection device 800 is in use. Typically, the latch mechanism would provide locking engagement of the door portion 802a with the body portion 802b.

Disposed within the housing 802 are a vacuum pump (not shown), a lancet assembly 808 generally comprising a molded plastic piece 830 to which a lancet 816 is affixed, a lancing assembly (not shown) into which the lancet assembly 808 is inserted, a battery (not shown), and electronics (not shown). A switch 809, FIG. 12B, is provided to activate the electronics, which may take the form as shown in FIG. 3. The vacuum pump communicates by an evacuation tube (not shown) with the volume enclosed by the door portion 802a when the door portion 802a is in the closed position. Optionally a check valve (not shown) may be placed in the evacuation tube between the vacuum pump and the volume enclosed by the door portion 802a when the door portion 802a is in the closed position.

During the process of obtaining the sample, the door portion 802a is closed to form a seal. The seal should be sufficiently tight so that a sufficient vacuum can be obtained by removing air from the volume enclosed by the door portion 802a when the door portion 802a is in the closed position.

The area of the door portion 802a of the housing 802 that is to contact the skin is equipped with a seal (not shown). The seal surrounds an opening 812 (shown in dotted lines in FIG. 12B) in the door portion 802a as disclosed in co-pending application entitled METHOD AND APPARATUS FOR OBTAINING BLOOD FOR DIAGNOSTIC TESTs Ser. No. 08/982,324. The opening 812 may be round, oval, rectangular or any other shape. The opening 812 in the door portion 802a allows communication between the surface of the skin and a blood extraction chamber adjacent to a fluid collector, shown here in the form of a glucose detector 814, which may take the shape of a strip. Other types of fluid collectors may also be used, and those of skill in the art will recognize that the present embodiment could easily be modified to include more than one fluid collector. Preferably, the glucose detector 814 used in the embodiment shown in FIGS. 12A and 12B contains an opening 815 in approximately the middle of glucose detector 814 for the lancet 816 to pass through, as disclosed in co-pending application entitled METHOD AND APPARATUS FOR OBTAINING BLOOD FOR DIAGNOSTIC TESTS, Ser. No. 08/982,323. The opening 815 is preferably in alignment with opening 812 and the lancet 816. The opening 815 may be covered with a mesh.

When in use, the blood collection device 800 is positioned so that the lancing assembly is placed over the region on the surface of the skin from which the fluid sample is to be obtained such that the lancing assembly is approximately perpendicular to the surface of the skin. In order to obtain the sample of blood, the door portion 802$a$ of the housing 802 is placed against the skin, whereby the seal surrounding opening 812 allows a satisfactory vacuum to be effected. The switch 809 is actuated, typically by being pressed, thereby activating the electronics, described in FIG. 3 and discussed above, which starts the vacuum pump. The vacuum pump then provides a suction action. The action of the vacuum pump withdraws air from the volume enclosed by the door portion 802$a$ when the door portion 802$a$ is in the closed position, and causes the skin circumscribed by the seal to be drawn toward the opening 812. This results in the skin becoming engorged with blood. Engorgement of the skin with blood is accompanied by a stretching of and rising up of the skin to the opening 812 in the door portion 802$a$.

After an appropriate period of time, which is typically pre-set by the programmed electronics, the lancing assembly is triggered, thereby causing the lancet 816 to penetrate the skin that has been pulled up into the opening 812 of the door portion 802$a$ and that is engorged with blood. The lancet 816 is preferably triggered automatically by activation of a solenoid valve (not shown) that causes a vacuum-actuated piston (not shown) to trigger the lancet 816, as disclosed in co-pending application entitled METHOD AND APPARATUS FOR OBTAINING BLOOD FOR DIAGNOSTIC TESTS, Ser. No. 08/982,561. The remaining steps of the process relating to collection of a sample of blood are substantially similar to the steps described when using the embodiment shown in FIGS. 1 through 4.

In the embodiment shown in FIGS. 12A and 12B, the glucose detector 814 is inserted into slot 818 of the door portion 802$a$ of the housing 802. Alignment channels 819$a$ and 819$b$, preferably C-shaped, along either side of slot 818 can be used to align the glucose detector 814 so that the glucose detector 814 is properly aligned with the lancet 816. Preferably, the alignment channels 819$a$ and 819$b$ cover only a small portion of each side of glucose detector 814 to minimize the chance of blood being left in the slot 818 and alignment channels 819$a$ and 819$b$ when the glucose detector 814 is removed. In a preferred embodiment, some portion of the glucose detector 814 should extend beyond the top of the door portion 802$a$ to ensure easy removal of the glucose detector 814. In the embodiment shown in FIGS. 12A and 12B, glucose detector 814 contains one or more electrical contacts (not shown) on the end opposite the end inserted into slot 818 that engage one or more electrical contacts (not shown) positioned within a slot 821 on the body portion 802$b$. The end of the glucose detector 814 with the electrical contacts is inserted into slot 821 on the body portion 802$b$ by the movement of the door portion 802$a$ when the door portion 802$a$ is closed. Alternatively, the blood extraction device 800 may be designed in such a way that the end of the glucose detector 814 containing one or more electrical contacts is inserted into slot 818 to engage with one or more electrical contacts positioned within slot 818 and the end of the glucose detector 814 opposite the end containing the electrical contacts is inserted into slot 821 by the movement of the door portion 802$a$ when the door portion 802$a$ is closed. Alignment channels 819$a$ and 819$b$ preferably may also stop the lancet assembly 808 from extending beyond the alignment channels 819$a$ and 819$b$ and prevent the lancet 816 from extending more than is desired into the skin. The preferred lancing depth typically ranges from about 0.5 mm to about 3 mm into the skin. The door portion 802$a$ is closed during the process of obtaining a sample of blood.

After the lancet 816 pierces the skin and is retracted, blood is withdrawn, under the aid of the vacuum, toward and onto the glucose detector 814. When a sufficient amount of blood has been collected, the glucose detector 814 generates a signal that results in deactivation of the vacuum pump and the vacuum is released by, for example, an electronically controlled valve. Alternatively, the vacuum pump may be stopped after a pre-set time interval. The blood collection device 800 may then be removed from the individual's skin. Thereafter the glucose detector 814 generates a signal, as described above, indicative of glucose level, which signal is transmitted via electrical circuitry to the electronics housed in the blood collection device 800. The signal is processed by such electronics, in the manner described above, and the results obtained from the glucose detector 814 can be displayed on a screen 820, typically a conventional liquid crystal digital display. Other manners of display may also be used.

Upon completion of the measurement, the door portion 802$a$ may be opened and the glucose detector 814 and the lancet 816 may be replaced. The lancet 816 and the glucose detector 814 may be replaced immediately after use, immediately before use or may be replaced at any other time.

Referring now to FIGS. 13A through 13E, which depict another embodiment of the present invention, blood extraction device 900 comprises a housing 902 having a door portion 902$a$ (shown in the open position in FIG. 13A, in a partially closed position in FIG. 13B, and in the closed position in FIGS. 13C through 13E) that is attached to the body portion 902$b$ of the housing 902 by an attachment in the form of a hinge 906. Alternatively, the door portion 902$a$ may be attached to the body portion 902$b$ by frictional engagement, a detent (not shown) or any combination of a hinge 906, frictional engagement, and a detent. When a hinge 906 is used, it may optionally be spring biased to retain the door portion 902$a$ in the open or a closed position. A detent (not shown) may be provided on the door portion 902$a$ to engage with a protrusion (not shown) on the body portion 902$b$, or vice versa, to maintain the door portion 902$a$ in the open or closed position when desired. Although a hinge 906 is provided in the embodiment shown in FIGS. 13A through 13E, any other attachment or combination of attachments that allows the door portion 902$a$ to attach to the body portion 902$b$ and alternate between an open and closed position is acceptable. A gasket or other seal arrangement (not shown) is provided to seal the housing 902 when the door portion 902$a$ is closed. Additionally, a latch mechanism may be included to prevent accidental opening of the door portion 902$a$ when the blood collection device 900 is in use. Typically, the latch mechanism would provide locking engagement of the door portion 902$a$ with the body portion 902$b$.

Disposed within the housing 902 are a vacuum pump (not shown), a lancet assembly 908 generally comprising a molded plastic piece 930 to which a lancet 916 is affixed, a lancing assembly (not shown) into which the lancet assembly 908 is inserted, a battery (not shown), and electronics (not shown) for purposes described hereinafter. A switch 909 is provided to activate the electronics, which may take the form as shown in FIG. 3. The vacuum pump communicates by an evacuation tube (not shown) with the volume enclosed by the door portion 902a when the door portion 902a is in the closed position. Optionally a check valve (not shown) may be placed in the evacuation tube between the vacuum pump and the volume enclosed by the door portion 902a when the door portion 902a is in the closed position.

During the process of obtaining the sample, the door portion 902a is closed to form a seal. The seal should be sufficiently tight so that a sufficient vacuum can be obtained by removing air from the volume enclosed by the door portion 902a when the door portion 902a is in the closed position.

Figure 13A:
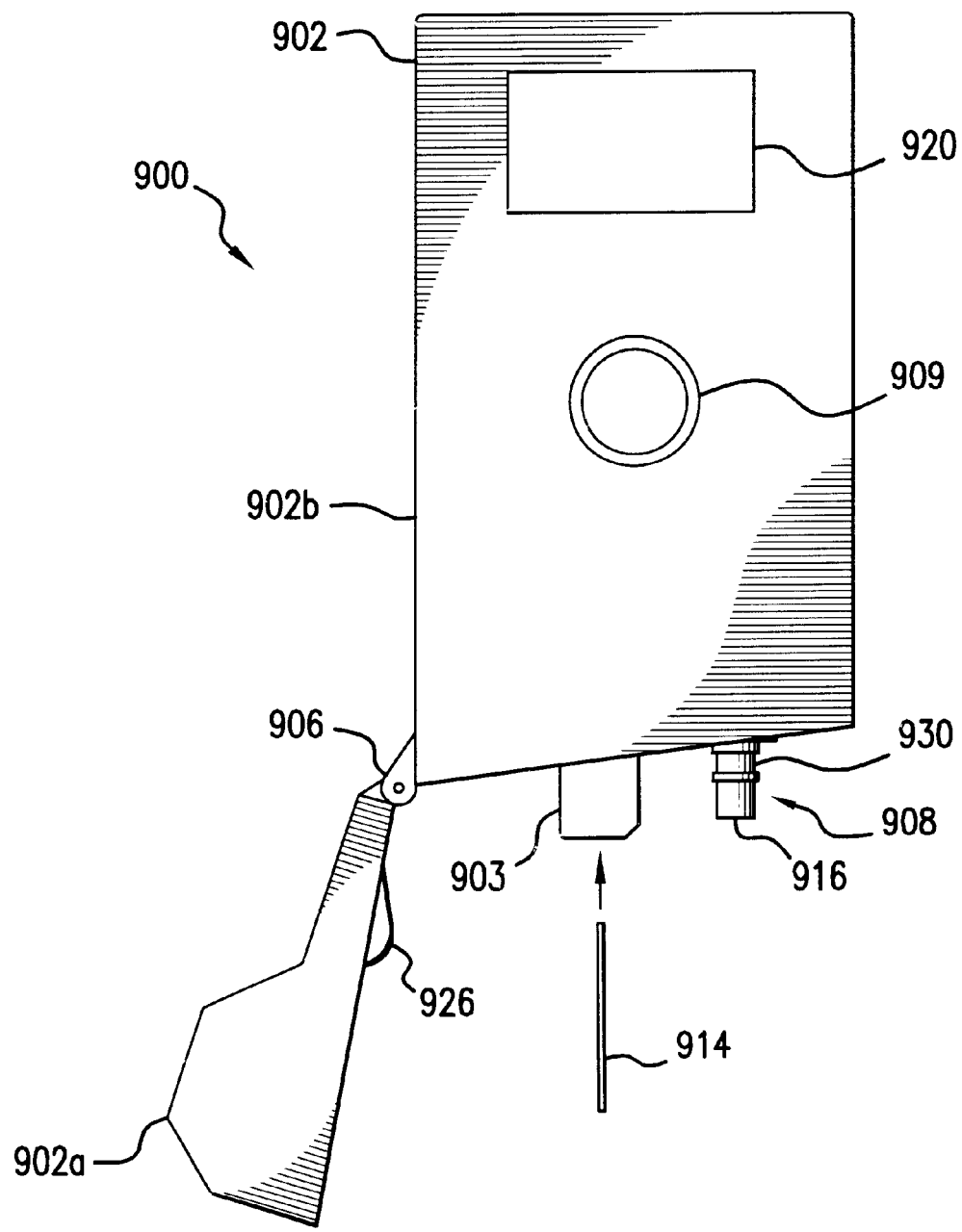
FIGS. 13A through 13E, depicts a partial cross-sectional drawing of an embodiment of the apparatus of this invention.
Figure 13B:
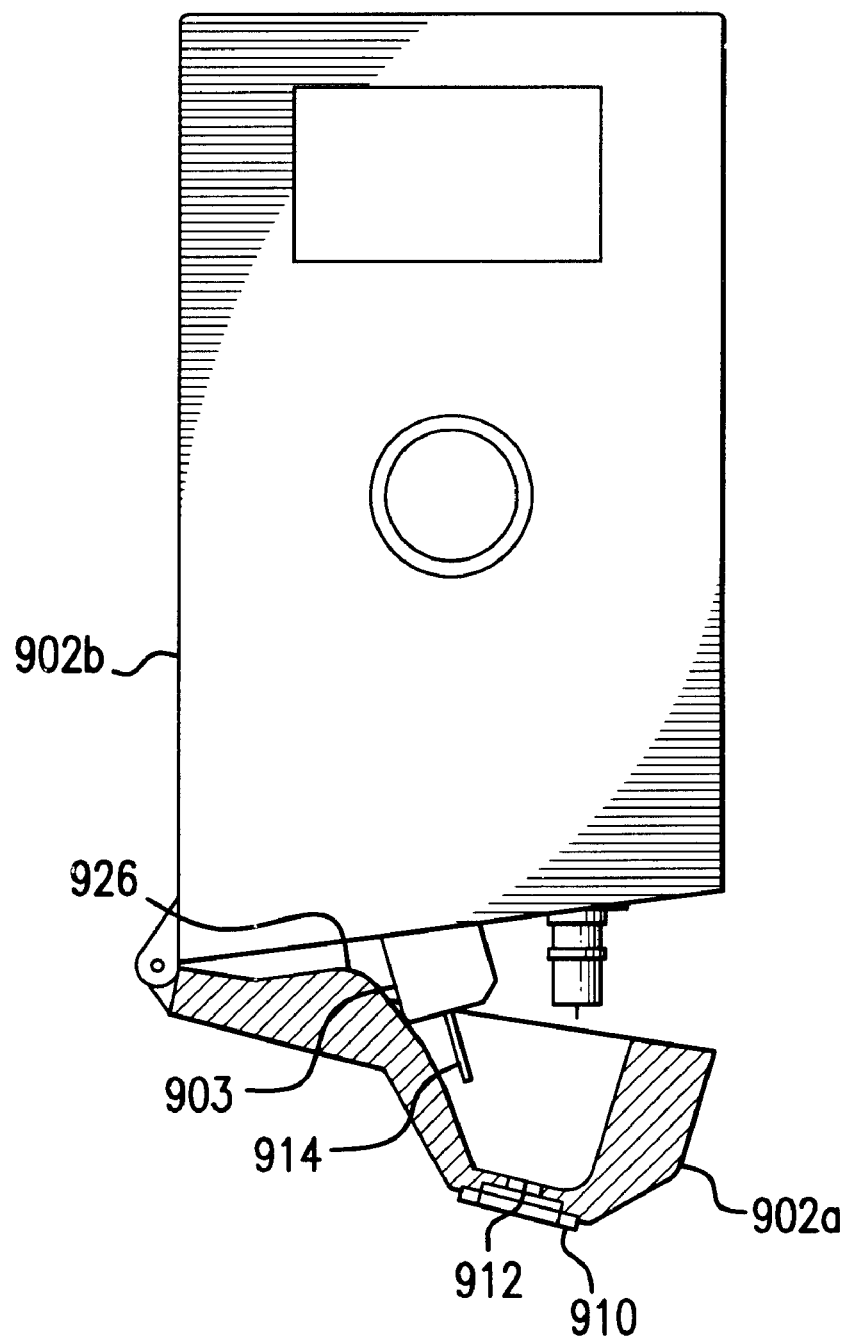

The area of the door portion 902a of the housing 902 that is to contact the skin is equipped with a seal 910, FIG. 13B. The seal 910 surrounds an opening 912 in the door portion 902a, as disclosed in a co-pending application entitled METHOD AND APPARATUS FOR OBTAINING BLOOD FOR DIAGNOSTIC TESTS, Ser. No. 08/982,324. The opening 912 may be round, oval, rectangular or any other shape. The opening 912 in the door portion 902a allows communication between the surface of the skin and a blood extraction chamber adjacent to a fluid collector, shown here in the form of a glucose detector 914, which may take the shape of a strip. Other types of fluid collectors may also be used, and those of skill in the art will recognize that the present embodiment could easily be modified to include more than one fluid collector. Preferably, the glucose detector 914 used in the embodiment shown in FIGS. 13A through 13E contains a semi-circular notch (not shown) in the region of the glucose detector 914 that comes into contact with the blood, as disclosed in co-pending application entitled METHOD AND APPARATUS FOR OBTAINING BLOOD FOR DIAGNOSTIC TESTS, Ser. No. 08/982,323. The semi-circular notch may be covered with mesh.

Figure 13C:
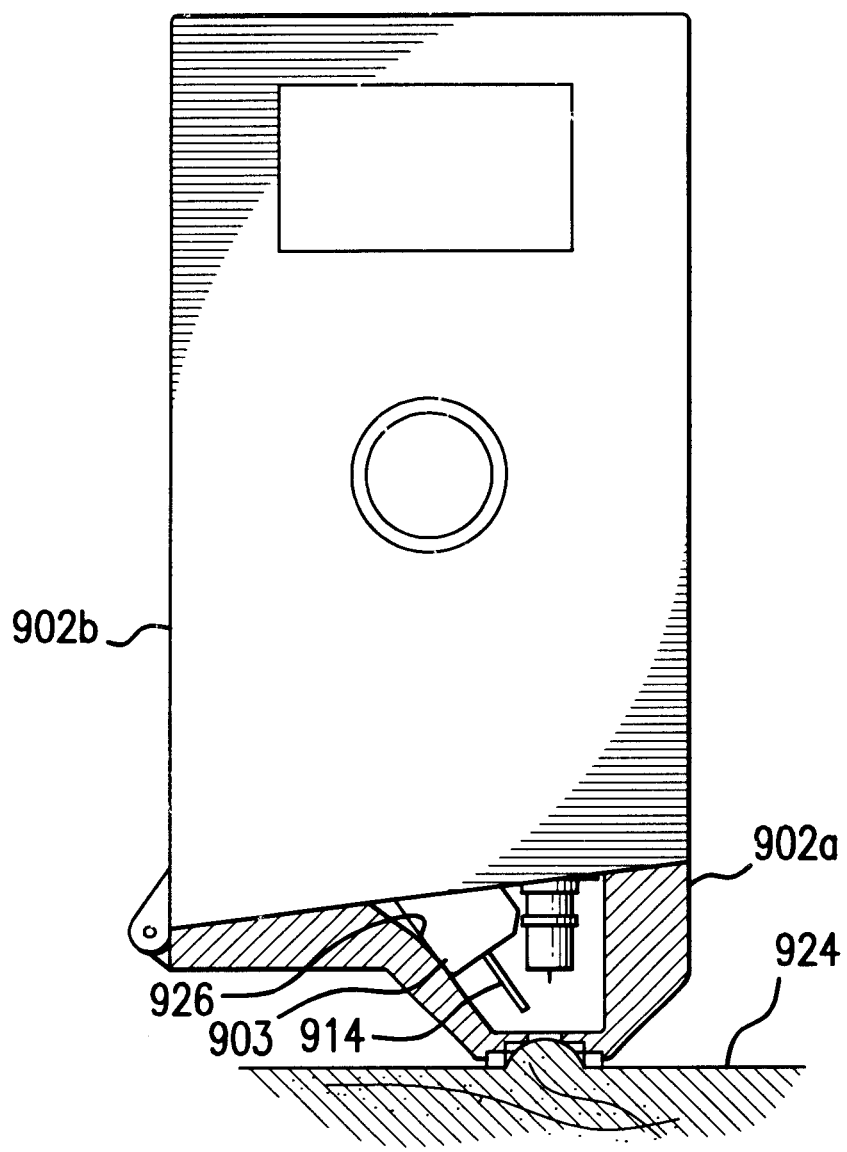
Figure 13D:
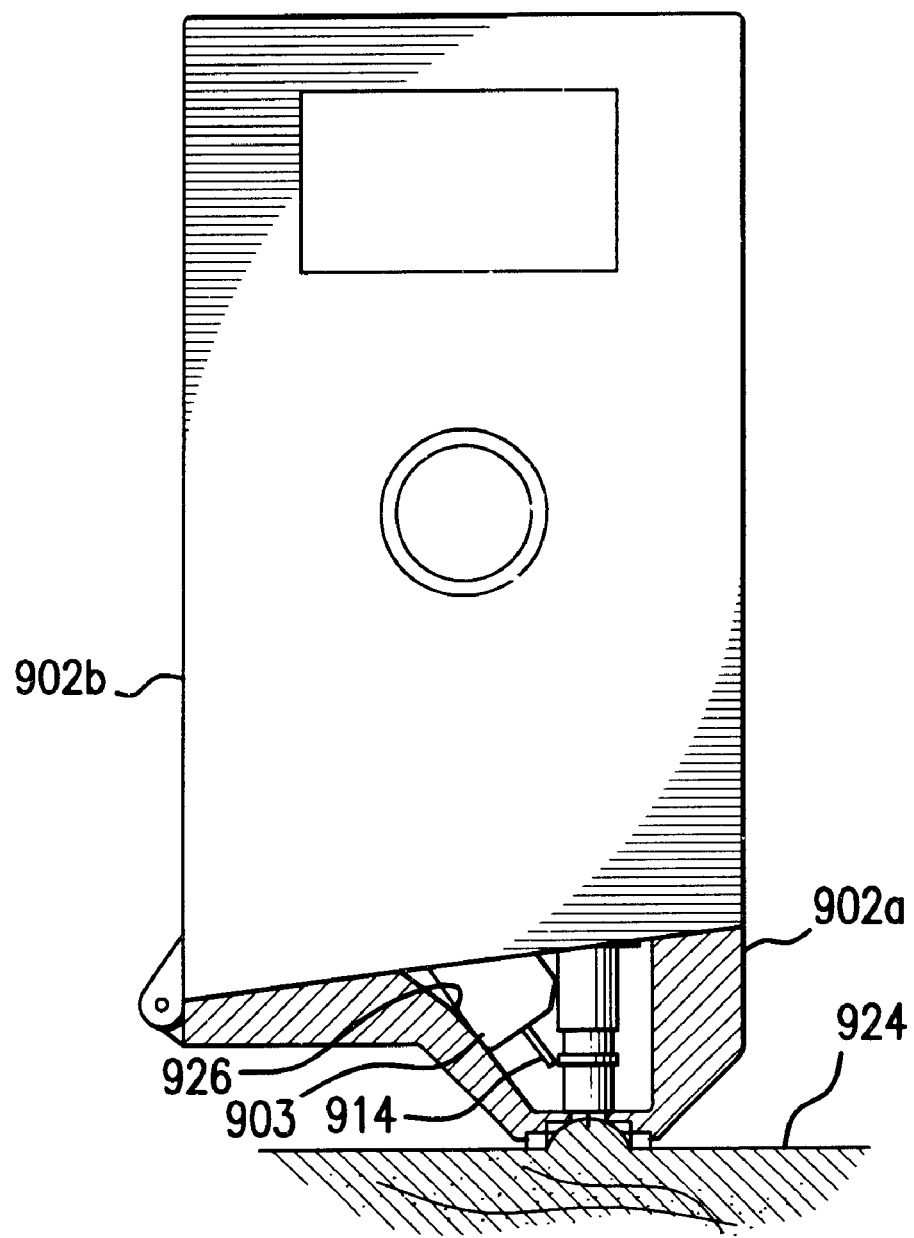
Figure 13E:
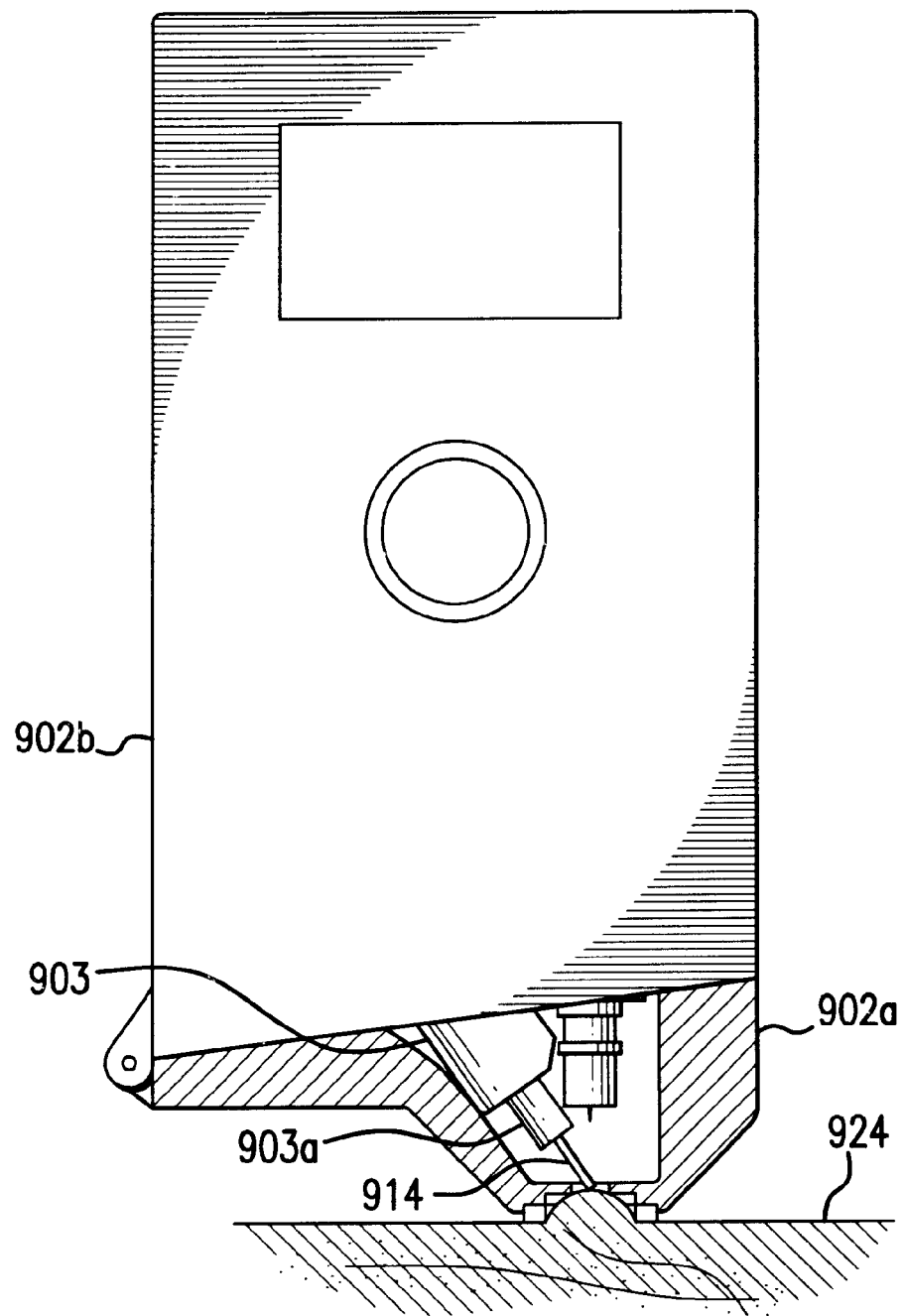

When in use, the blood collection device 900 is positioned so that the lancing assembly is placed over the region on the surface of the skin 924, FIG. 13C, from which the fluid sample is to be obtained such that the lancing assembly is approximately perpendicular to the surface of the skin 924. In order to obtain the sample of blood, the door portion 902a of the housing 902 is placed against the skin 924, whereby the seal 910 surrounding opening 912 allows a satisfactory vacuum to be effected. The switch 909 is actuated, typically by being pressed, thereby activating the electronics, described in FIG. 3 and discussed above, which starts the vacuum pump. The action of the vacuum pump withdraws air from the volume enclosed by the door portion 902a when the door portion 902a is in the closed position and causes the skin circumscribed by the seal 910 to be drawn toward the opening 912. This results in the skin becoming engorged with blood. Engorgement of the skin with blood is accompanied by a stretching of and rising up of the skin to the opening 912 in the door portion 902a, as depicted in FIGS. 13C through 13E.

After an appropriate period of time, which is typically pre-set by the programmed electronics, the lancing assembly is triggered, thereby causing the lancet 916 to penetrate the skin that has been pulled up into the opening 912 of the door portion 902a. The lancet 916 is preferably triggered automatically by activation of a solenoid valve (not shown) that causes a vacuum-actuated piston (not shown) to trigger the lancet 916, as disclosed in co-pending application entitled METHOD AND APPARATUS FOR OBTAINING BLOOD FOR DIAGNOSTIC TESTS, Ser. No. 08/982,561.

In the embodiment shown in FIGS. 13A through 13E, the glucose detector 914 is inserted into a slot (not shown) of a movable projection 903 of the body portion 902b of the housing 902. Glucose detector 914 contains one or more electrical contacts (not shown) on the end inserted into the slot which engage one or more electrical contacts (not shown) positioned within the slot. After the glucose detector 914 is positioned within the slot of the movable projection 903, movable projection 903 is pushed inwardly. A latch or other mechanism holds the movable projection 903 in the inward position until triggered, as discussed below.

As shown in FIGS. 13B through 13C, when the door portion 902a is closed, a cam surface 926 on the interior of the door portion 902a moves the movable projection 903 and the glucose detector 914 in a direction towards the lancing assembly and lancet assembly 908. Although a cam surface 926 is shown in FIG. 13A, other alignment approaches may also be utilized. The lancet 916 is then triggered, penetrates the skin 924, as shown in FIG. 13D, and is quickly retracted. Shortly after the lancet 916 is triggered, as discussed above, the movable projection 903 is triggered, preferably electronically such as by the release of a latch or other mechanism, causing an interior portion 903a of the movable projection 903 to move outwardly, such as by a sliding mechanism, and thereby causing the glucose detector 914 to move to a position near the position where the lancet contacted the skin 924, as shown in FIG. 13E, causing the glucose detector 914 to come into contact with the blood. The area of the interior of the door portion 902a immediately adjacent to the opening 912 may also preferably stop the lancet assembly 908 from extending beyond the door portion 902a and prevents the lancet 916 from extending more than is desired into the skin. The preferred lancing depth typically ranges from about 0.5 mm to about 3 mm into the skin. The door portion 902a is closed during the process of obtaining a sample of blood.

After the lancet 916 pierces the skin 924 and is retracted, blood is withdrawn, under the aid of the vacuum, toward and onto the glucose detector 914. When a sufficient amount of blood has been collected, the glucose detector 914 generates a signal which results in deactivation of the vacuum pump and the vacuum is released by, for example, an electronically controlled valve. Alternatively, the vacuum pump may be stopped after a pre-set time interval. The blood collection device 900 may then be removed from the individual's skin. Thereafter, the glucose detector 914 generates a signal, as described above, indicative of glucose level, which signal is transmitted via electrical circuitry to the electronics housed in the blood collection device 900. The signal is processed by such electronics, in the manner described above, and the results obtained from the glucose detector 914 can be displayed on a screen 920, typically a conventional liquid crystal digital display. Other manners of display may also be used.

Upon completion of the measurement, the door portion 902a may be opened and the glucose detector 914 and the lancet 916 may be replaced. The lancet 916 and the glucose detector 914 may be replaced immediately after use, immediately before use or may be replaced at any other time.

Figure 14A:
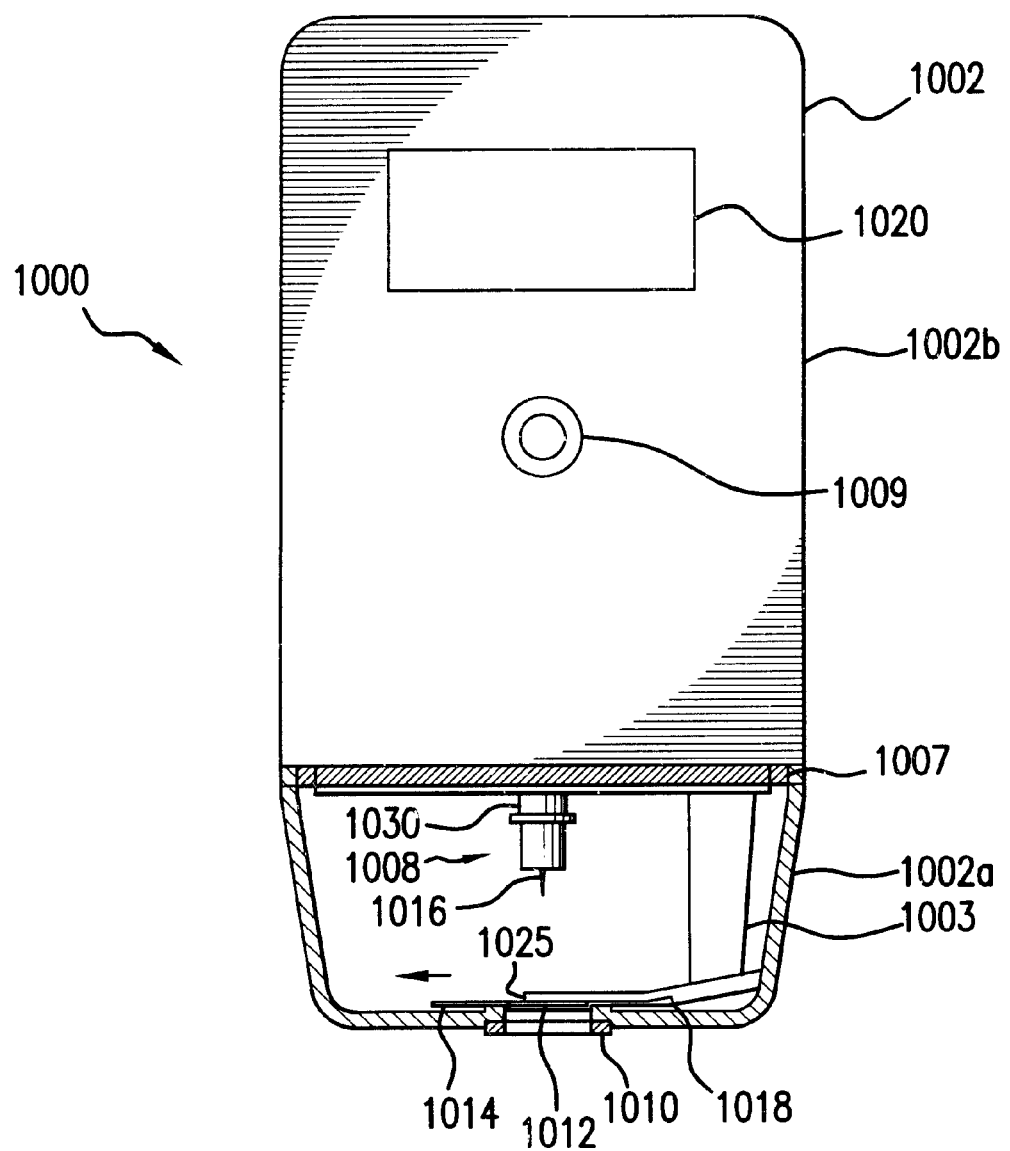
FIGS. 14A through 14C, depicts a partial cross-sectional drawing of an embodiment of the apparatus of this invention.
Figure 14B:
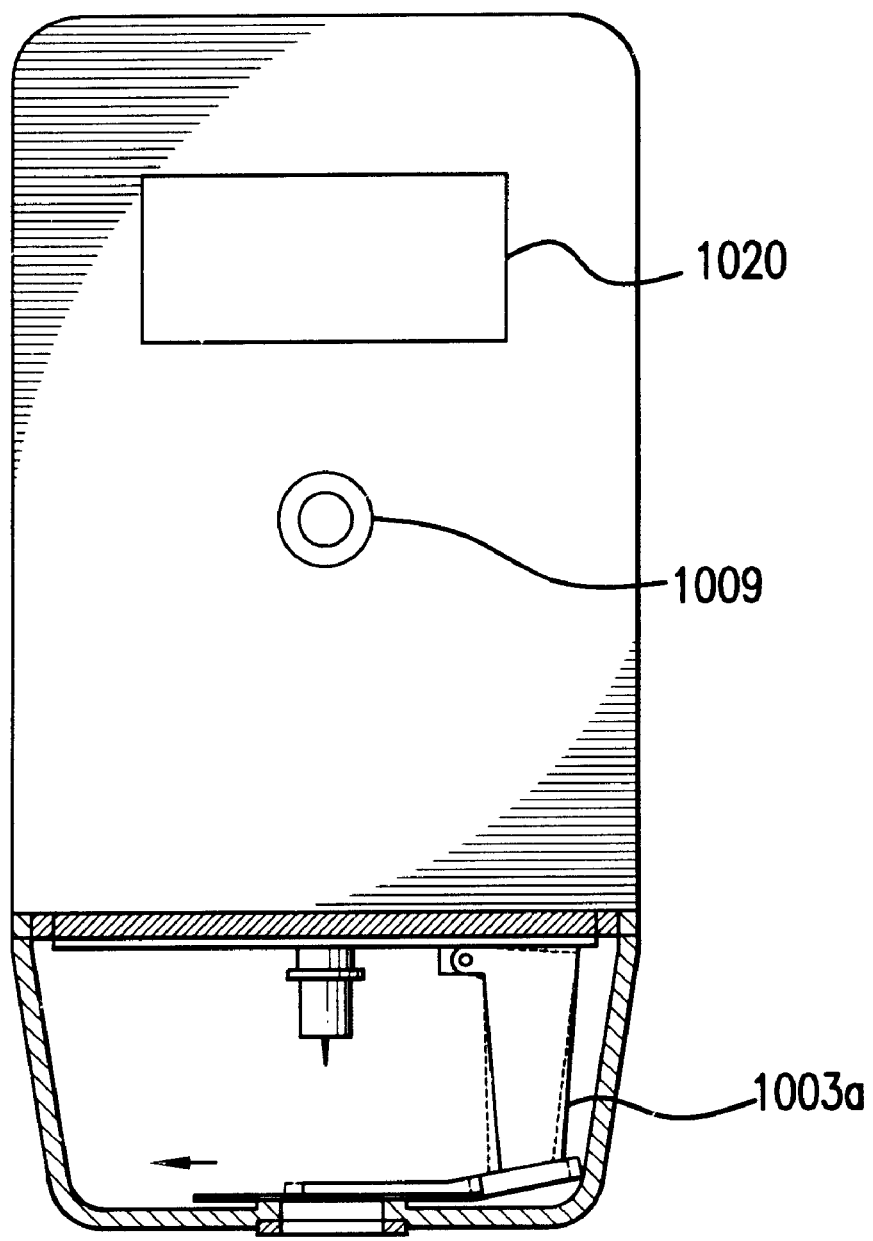
Figure 14C:
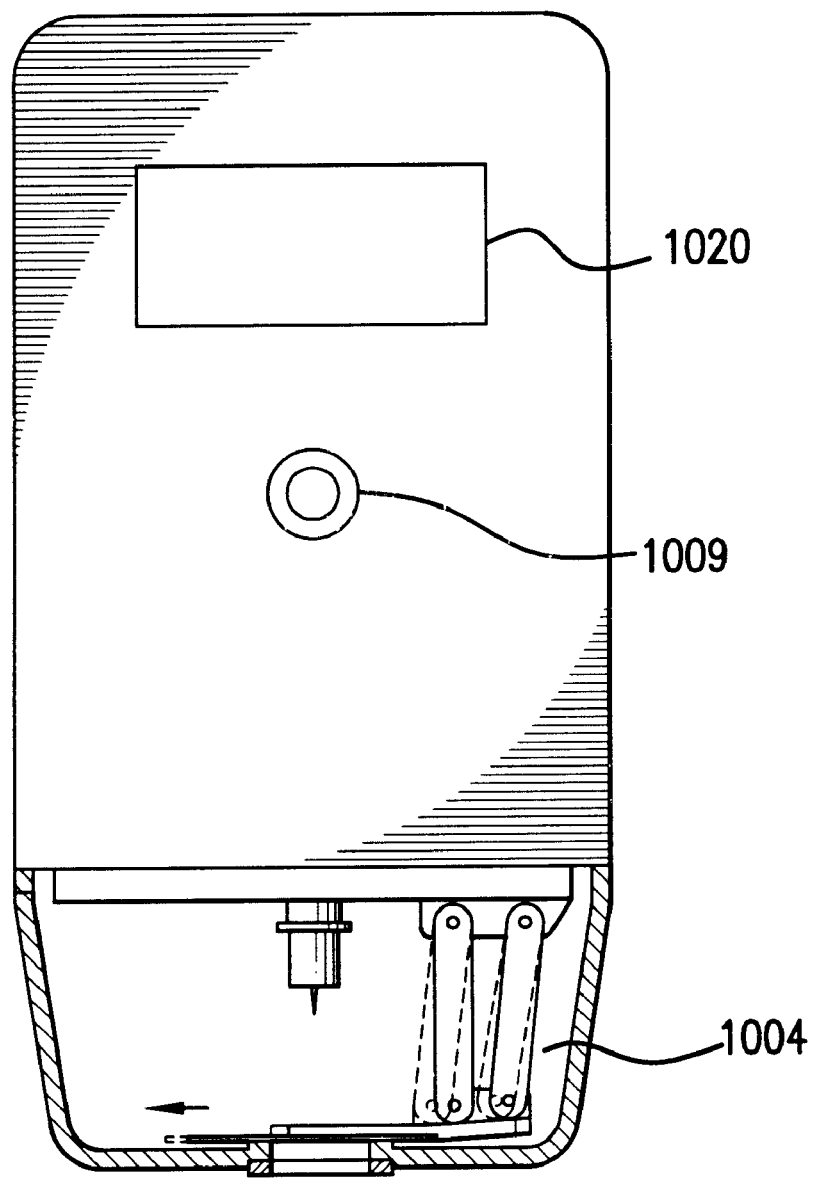

Referring now to FIGS. 14A through 14C, which depict another embodiment of the present invention, blood extraction device 1000 comprises a housing 1002 having a door portion 1002a (shown in the closed position in FIGS. 14A through 14C) that is attached to the body portion 1002b of the housing 1002 by an attachment in the form of a hinge (not shown). Alternatively, the door portion 1002a may be attached to the body portion 1002b by frictional engagement, a detent (not shown), or any combination of a hinge, frictional engagement, and a detent. When a hinge is used, it may optionally be spring biased to retain the door portion 1002a in the open or closed position. A detent (not shown) may be provided on the door portion 1002a to engage with a protrusion (not shown) on the body portion 1002b, or vice versa, to maintain the door portion 1002a in the open or closed position when desired. Although a hinge (not shown) is provided in the embodiment shown in FIGS. 14A through 14C, any other attachment or combination of attachments that allows the door portion 1002a to attach to the body portion 1002b and alternate between an open and closed position is acceptable. A gasket or other seal arrangement 1007 is provided to seal the housing 1002 when the door portion 1002a is closed. Alternatively, the housing 1002 may also include a movable interior cover portion (not shown), similar to that described in the embodiment shown in FIGS. 1 1A through 11C, that advantageously may be positioned around the lancing assembly (not shown) in a manner to allow the movable interior cover portion to be opened and closed. Any attachment that allows the movable interior cover portion to attach to the body portion 1002b and alternate between an open and closed position is acceptable. Additionally, a latch mechanism may be included to prevent accidental opening of the door portion 1002a when the blood collection device 1000 is in use. Typically, the latch mechanism would provide locking engagement of the door portion 1002a with the body portion 1002b.

Disposed within the housing 1002 are a vacuum pump (not shown), a lancet assembly 1008 generally comprising a molded plastic piece 1030 to which a lancet 1016 is affixed, a lancing assembly (not shown) into which the lancet assembly 1008 is inserted, a battery (not shown), and electronics (not shown) for purposes described hereinafter. A switch 1009 is provided to activate the electronics, which may take the form as shown in FIG. 3. The vacuum pump communicates by an evacuation tube (not shown) with the volume enclosed by the door portion 1002a when the door portion 1002a is in the closed position. Optionally a check valve (not shown) may be placed in the evacuation tube between the vacuum pump and the volume enclosed by the door portion 1002a when the door portion 1002a is in the closed position.

During the process of obtaining the sample, the door portion 1002a is closed to form a seal. The seal should be sufficiently tight so that a sufficient vacuum can be obtained by removing air from the volume enclosed by the door portion 1002a when the door portion 1002a is in the closed position.

The area of the door portion 1002a of the housing 1002 that is to contact the skin is equipped with a seal 1010. The seal 1010 surrounds an opening 1012 in the door portion 1002a as disclosed in co-pending application entitled METHOD AND APPARATUS FOR OBTAINING BLOOD FOR DIAGNOSTIC TESTS, Ser. No. 08/982,324. The opening 1012 may be round, oval, rectangular or any other shape. The opening 1012 in the door portion 1002a allows communication between the surface of the skin and a blood extraction chamber adjacent to a fluid collector, shown here in the form of a glucose detector 1014, which may take the shape of a strip. Other types of fluid collectors may also be used, and those of skill in the art will recognize that the present embodiment could easily be modified to include more than one fluid collector. Preferably, the glucose detector 1014 contains at least one opening (not shown) in approximately the middle of glucose detector 1014 for the lancet 1016 to pass through, as disclosed in co-pending application entitled METHOD AND APPARATUS FOR OBTAINING BLOOD FOR DIAGNOSTIC TESTS, Ser. No. 08/982,323. In this embodiment, at least one opening in approximately the middle of glucose detector 1014 is preferably in alignment with opening 1012 and lancet 1016 and may be covered with a mesh. Alternatively, the glucose detector 1014 used in the embodiment shown in FIGS. 14A through 14C may contain a semi-circular notch (not shown) in the region of the glucose detector 1014 that comes into contact with the blood, as disclosed in co-pending application entitled METHOD AND APPARATUS FOR OBTAINING BLOOD FOR DIAGNOSTIC TESTS, Ser. No. 08/982, 323. The semi-circular notch may be covered with a mesh.

When in use, the blood collection device 1000 is positioned so that the lancing assembly is placed over the region on the surface of the skin from which the fluid sample is to be obtained such that the lancing assembly is approximately perpendicular to the surface of the skin. In order to obtain the sample of blood, the door portion 1002a of the housing 1002 is placed against the skin, whereby the seal 1010 surrounding opening 1012 allows a satisfactory vacuum to be effected. The switch 1009 is actuated, typically by being pressed, thereby activating the electronics, described in FIG. 3 and discussed above, which starts the vacuum pump. The action of the vacuum pump withdraws air from the volume enclosed by the door portion 1002a when the door portion 1002a is in the closed position and causes the skin circumscribed by the seal 1010 to be drawn toward the opening 1012. This results in the skin becoming engorged with blood. Engorgement of the skin with blood is accompanied by a stretching of and rising up of the skin to the opening 1012 in the door portion 1002a.

After an appropriate period of time, which is typically pre-set by the programmed electronics, the lancing assembly is triggered, thereby causing the lancet 1016 to penetrate the skin that has been pulled up into the opening 1012 of the door portion 1002a. The lancet 1016 is preferably triggered automatically by activation of a solenoid valve (not shown) that causes a vacuum-actuated piston (not shown) to trigger the lancet 1016, as disclosed in co-pending application entitled METHOD AND APPARATUS FOR OBTAINING BLOOD FOR DIAGNOSTIC TESTS, Ser. No. 08/982,561.

In the embodiment shown in FIGS. 14A through 14C, the glucose detector 1014 is inserted into a slot 1018 of a movable projection 1003 of the body portion 1002b of the housing 1002. Glucose detector 1014 contains one or more electrical contacts (not shown) on the end inserted into the slot 1018 which engage one or more electrical contacts (not shown) positioned within the slot 1018. Preferably, after the glucose detector 1014 is positioned within the slot 1018 of movable projection 1003, movable projection 1003 is pushed in a retract manner. A latch or other mechanism holds the projection in the retracted position until triggered, as discussed below.

To obtain a sample of blood, the door portion 1002a is closed. As discussed above, a vacuum is created and the skin becomes engorged with blood. After an appropriate period of time, the lancet 1016 is then triggered and, depending on the type of glucose detector 1014 being used, the lancet 1016 contacts the skin by moving through an opening in approximately the middle of glucose detector 1014 or moving beyond the end of the glucose detector 1014 containing a semi-circular notch. The lancet 1016 then penetrates the skin, and is quickly retracted. Shortly after the lancet 1016 is triggered and retracted, as discussed above, the movable projection 1003 is triggered, causing the glucose detector 1014 to extend laterally across the width of the blood collection device 1000, as shown by the arrow in FIG. 14A, in order to come into contact with the blood. This movement may be caused by the release of a latch. Alternatively, the glucose detector 1014 may be moved incrementally through the action of a solenoid or other electromechanical device. In one embodiment, the glucose detector 1014 may be moved via a pivoting projection 1003a, FIG. 14B. In another embodiment, the glucose detector 1014 may be moved via a four-bar linkage 1004, FIG. 14C.

The movable projection 1003 may also comprise an extension 1025 that extends laterally across the width of the blood collection device 1300. When present, extension 1025 stops the lancet assembly 1008 from extending beyond the extension 1025 and prevents the lancet 1016 from extending more than is desired into the skin. The preferred lancing depth typically ranges from about 0.5 mm to about 3 mm into the skin.

After the lancet 1016 pierces the skin and is retracted, the movable projection 1003 is triggered and the glucose detector 1014 is moved, as discussed above, so that a wicking portion (not shown) of glucose detector 1014 is above the opening created in the skin. Blood is then withdrawn, under the aid of the vacuum, toward and onto the detector 1014. When a sufficient amount of blood has been collected, the glucose detector 1014 then generates a signal which results in deactivation of the vacuum pump and the vacuum is released by, for example, an electronically controlled valve. Alternatively, the vacuum pump may be stopped after a pre-set time interval. The blood collection device 1000 may then be removed from the individual's skin. Thereafter, the glucose detector 1014 generates a signal, as described above, indicative of glucose level, which signal is transmitted via electrical circuitry to the electronics housed in the blood collection device 1000. The signal is processed by such electronics, in the manner described above, and the results obtained from the glucose detector 1014 can be displayed on a screen 1020, typically a conventional liquid crystal digital display. Other manners of display may also be used.

Upon completion of the measurement, the door portion 1002a may be opened and the glucose detector 1014 and the lancet 1016 may be replaced. The lancet 1016 and the glucose detector 1014 may be replaced immediately after use, immediately before use or may be replaced at any other time.

In each of the embodiments shown in the foregoing FIGS. 5–14 the housing, vacuum pump, lancing assembly, lancet assembly, battery, electronics, evacuation tube, check valve, nosepiece assembly, blood extraction chamber, lancet, and solenoid valve can be made of the same materials as the corresponding components of the apparatus shown in FIGS. 1, 2, and 3. The seals 104, 207, 307, 407, 507, 607, 707, 807, 907, and 1007 can be made of the same material as the seal of the nosepiece assembly. The components shown in the foregoing FIGS. 5–14 function in the same manner as do the corresponding components of the apparatus shown in FIGS. 1, 2, and 3.

Figure 18:
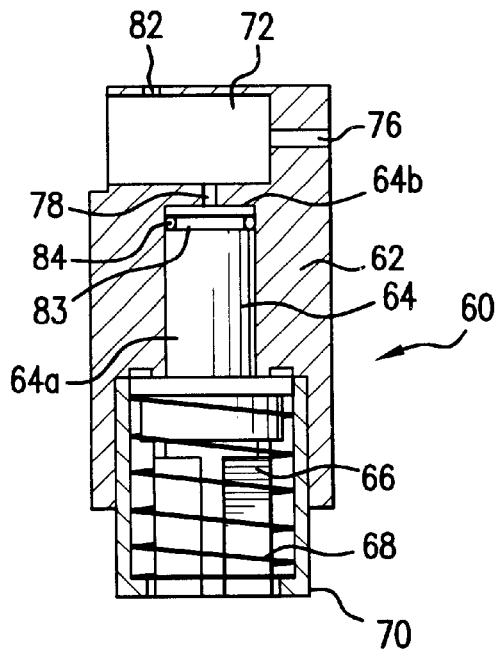
FIG. 18 is an elevational view, in cross section, of one embodiment of the lancing assembly of this invention in assembled configuration.
Figure 19:
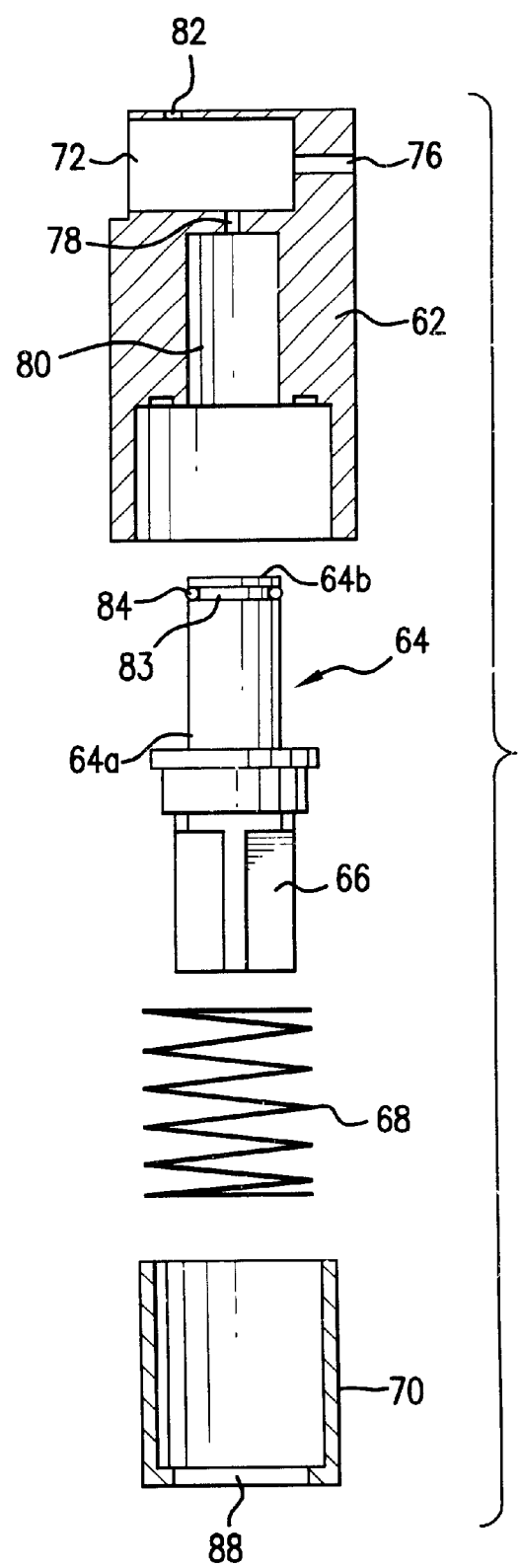
FIG. 19 is an exploded view, in cross section, of the lancing assembly of FIG. 18.
Figure 21:
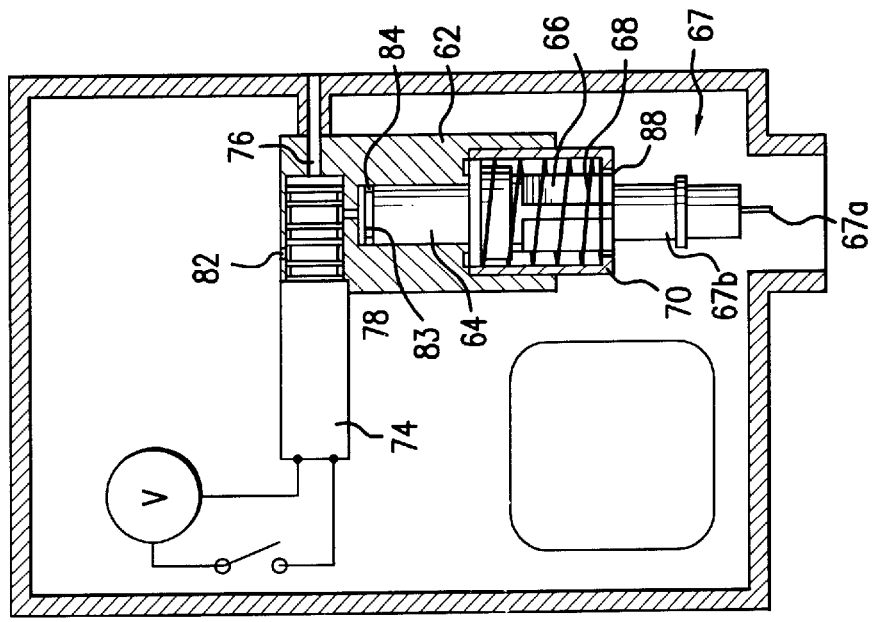
FIG. 21 is a schematic diagram illustrating the positioning of the components of the lancing assembly of this invention. In this figure, the lancet has been inserted into the lancet holder and the valve has been inserted into the valve manifold.
Figure 20:
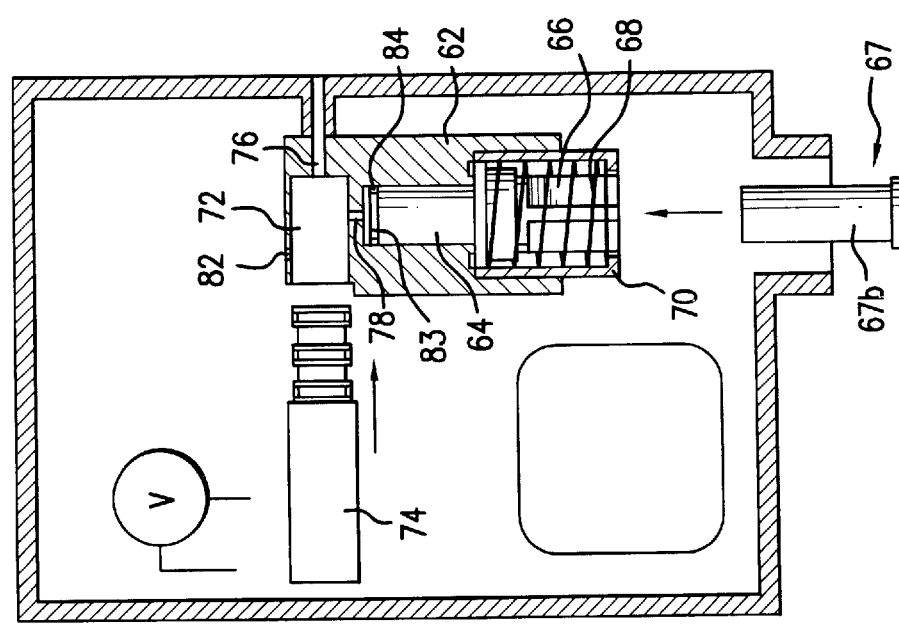
FIG. 20 is a schematic diagram illustrating the positioning of the components of the lancing assembly of this invention. In this figure, the lancet assembly has not yet been inserted into the lancet holder and the valve has not yet been inserted into the valve manifold.
Figure 25:
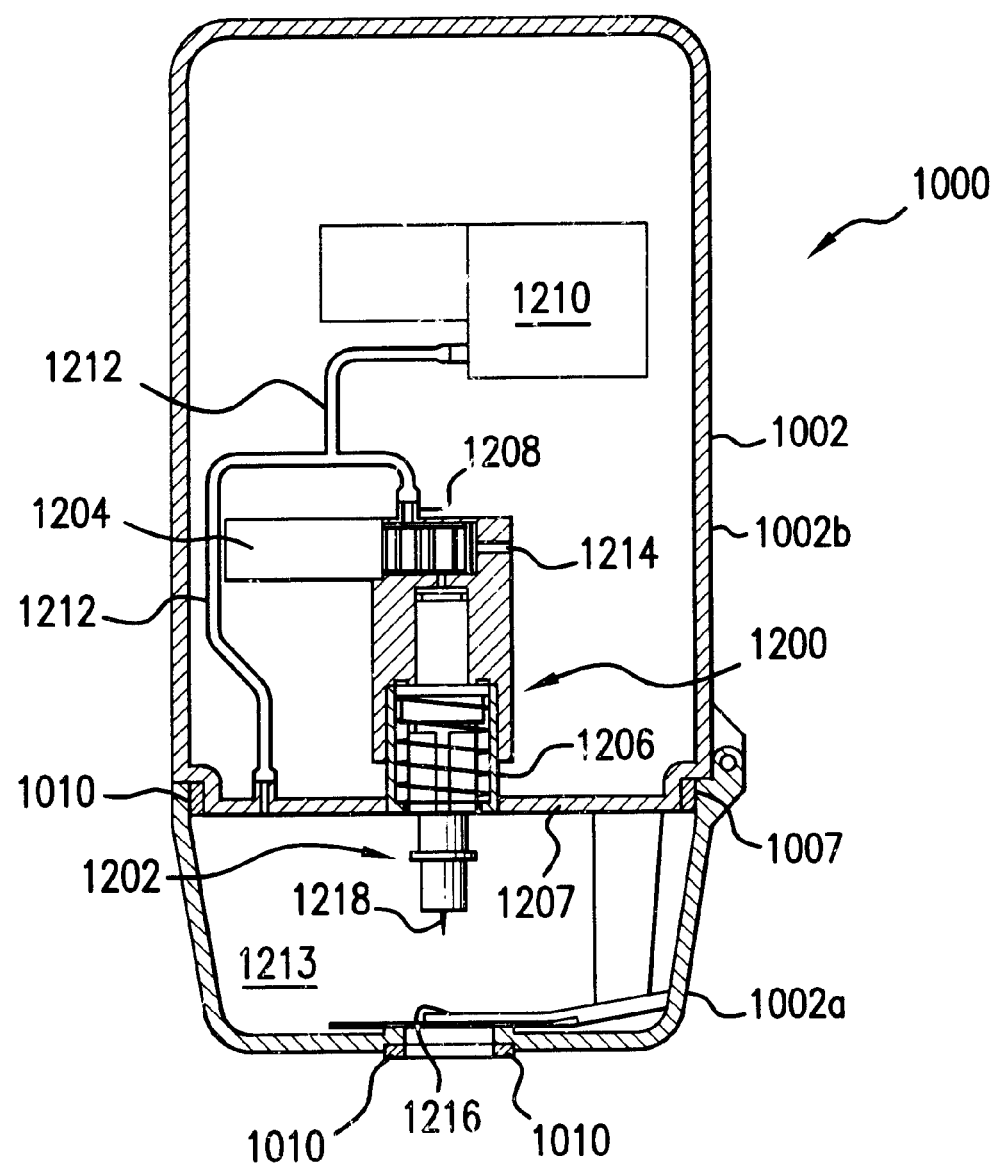
FIG. 25 is an elevational view, in cross section, of the lancing assembly of this invention installed in an embodiment of an apparatus of this invention.

FIG. 25 illustrates a preferred installation of the lancing assembly shown in FIGS. 18 and 19 inside a prototype of an embodiment of the blood collecting apparatus of this invention. The lancing assembly 1200, shown in its retracted pre-thrust position, has been fitted with a standard lancet assembly 1202 and a three-way solenoid valve 1204. The cap 1206 of the lancing assembly 1200 is fitted into the partition 1207 of the apparatus 1000, thereby forming an effective seal against the partition 1207. The apparatus 1000 comprises a housing 1002, which comprises a door portion 1002a and a body portion 1002b. The exit port 1208 of the lancing assembly 1200 is connected to a vacuum pump 1210 by means of a passageway 1212, such as, for example, a connecting tube. The passageway 1212 is also connected to a cavity 1213 inside the door portion 1002a of the apparatus 1000. In this manner, the vacuum pump 1210 can deliver an equal level of vacuum pressure to the cavity 1213 and to the exit port 1208. The vacuum pressure inside the cavity 1213 can be maintained at a level at which the apparatus 1000 operates, because the vacuum pump 1210 can draw evacuated air from the cavity 1213 at a rate faster than the rate at which ambient air leaks into the cavity 1213 by way of the door seal 1007, the seal placed against the skin of a patient 1010, and the seal formed between the cap 1206 and the partition 1207 (not shown). The body 1002b of the housing 1002 of the apparatus 1000 contains air having a pressure level equal to the ambient pressure surrounding the apparatus. The level of pressure inside the body 1002b of the housing 1002 does not change during operation of the apparatus because the body 1002b of the housing 1002 contains a sufficient number of openings (not shown) that communicate with the surrounding ambient air. The air inside the body 1002b of the housing 1002 can enter the lancing assembly 1200 through the inlet port 1214 when the solenoid valve 1204 is activated to begin the lancing step. The difference in air pressure between the ambient air inside the body 1002b of the housing 1002 and the evacuated air inside the cavity 1213 in the door portion 1002a of the housing 1002 brings about the differential gas pressure needed to operate the lancing assembly. During the lancing step, the thrusting motion of the lancet assembly 1202 is halted by a lancet stop 1216. The lancet stop 1216 has an opening (not shown) that allows the lancet 1218 to pass through and penetrate the skin which is placed against the seal 1010. The lancing assembly in FIG. 25 can thus be used in a manner substantially identical to that shown in FIGS. 22A, 22B, and 22C.

It should be noted that the designs of the various housings shown in FIGS. 5–14 can be modified without substantially affecting the functioning of the components disposed within the housing or on the surface of the housing. For example, the shapes of the housings, the shapes of the door portions of the housings, the shapes of the cover portions of the housings, and the shapes of the remaining portiors of the housings can be modified without departing from the scope and spirit of this invention.

This invention provides numerous advantages over blood extraction devices of the prior art. Among these advantages are the following:

1. Ability to use parts of the body, other than the finger, as a site for the extraction of blood;
2. Reduction of pain by eliminating the need to lance the finger;
3. Increase in speed of collection of blood samples by means of pre-treatment comprising a combination of stretching of the skin in conjunction with heat or vacuum or both heat and vacuum;
4. Incorporation of glucose detector in apparatus for extracting the blood sample.

The following examples illustrate various features of the present invention but are not intended to in any way limit the scope of the invention as set forth in the claims. In the following examples, the term "pierce" and forms thereof and the term "puncture" and forms thereof are used interchangeably. Although the term "glucose detector" is used herein, one of ordinary skill in the art will recognize that the apparatus and methods of the present invention may also be used to perform other diagnostic tests.

EXAMPLES

Example 1

This example illustrates that greater volumes of blood can be extracted and collected by applying a vacuum, pulsed or continuous, after piercing than can be extracted and collected when no vacuum is applied. No vacuum was applied prior to piercing.

Each of four people had his forearm (dorsal forearm) punctured four times (at four different positions on the forearm) with a "BD ULTRA-FINE" lancet in a "MEDISENSE" lancet assembly (Model no. 97101) at two different levels of vacuum (−2.5 psig and −5.0 psig) and for each different vacuum pulsing frequencies (0, 0.2, 0.8, 3.2, 12.8, 25, 100 hertz). The vacuum was applied with a pipette tip having a diameter of 8 mm ("RAININ RT-200"). Four control runs without a vacuum were also carried out (one puncture per person). A total of 60 punctures per person were carried out. Accordingly, it can be seen that a total of 240 runs were carried out.

The vacuum was applied for a duration of 30 seconds after puncturing. Blood was collected into capillary tubes. In the control runs, the samples were extracted and collected 30 seconds after puncturing. The amount of blood collected was determined by measuring the length of blood in the tubes. The percentage of collections in which the volume of blood collected exceeded 1.0 µL was calculated. Sensation of pain was also recorded. The following pain scores were used:

Pain of 1=person did not feel anything or not sure if anything was felt

Pain of 2=person felt definite prick, not as painful as piercing of finger by standard finger lancet Pain of 3=person felt definite pain, approximately equal to a piercing of finger by standard finger lancet Blood collection results are set forth in TABLE I.

TABLE 1

| Frequency (hertz) | Average volume of blood sample collected at −2.5 psig (µL) | Percent of samples having >1 µL of blood collected at −2.5 psig | Average volume of blood sample collected at −5.0 psig (µL) | Percent of samples having >1 µL of blood collected at −5.0 psig |
|---|---|---|---|---|
| 0 (Continuous) | 1.6 | 69 | 3.1 | 94 |
| 0.2 | 1.1 | 44 | 3.0 | 94 |
| 0.8 | 1.1 | 63 |  | 75 |
| 3.2 | 1.5 | 56 | 3.8 | 75 |
| 12.8 | 1.8 | 75 | 3.1 | 100 |
| 25 | 2.3 | 75 | 3.2 | 94 |
| 100 | 2.4 | 81 | 2.7 | 88 |

With no vacuum, average volume of blood collected was 0.8 µL and 31% of the samples collected contained more than 1 µL. The pain results were as follows:

pain of 1=81% pain of 2=17% pain of 3=2%

The control runs (no vacuum) provided much lower volumes of blood collected than did the runs where vacuum was applied. Increased vacuum resulted in higher volumes of blood extracted. The pain was minimal, with only 2% of the punctures resulting in pain comparable to that resulting from a piercing of the finger.

Example 2

This example illustrates that application of vacuum prior to piercing as well as after piercing results in a greater volume of blood extracted than does the application of vacuum only after piercing.

Each of four people had his forearm (dorsal forearm, middle of forearm) punctured sixteen times (at sixteen different positions on the forearm) with a "BD ULTRA-FINE" lancet in a modified "MEDISENSE" lancet assembly at four different levels of vacuum. The four levels of vacuum used were −2.5, −5.0, −7.5, and −10.0 psig. The "MEDISENSE" lancet device was modified to allow vacuum to be pulled through the lancet assembly. Four punctures per person were carried out at each of the four levels of continuous vacuum. Accordingly, it can be seen that a total of 64 runs were carried out.

Prior to puncturing, the vacuum was applied for a period of 30 seconds; subsequent to puncturing, the vacuum was applied for a period of 30 seconds. The skin was under vacuum at the time the lancet was triggered. After the lancet was triggered, the lancet assembly was removed, and the vacuum was used to apply the same level of vacuum that had been used for the vacuum prior to puncturing. The vacuum, both prior to puncturing and subsequent to puncturing, was applied with a pipette tip having a diameter of 8 mm ("RAININ RT-200"). The pipette tip of the vacuum device was held level to the plane of the skin. Blood was then collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE II.

TABLE II

| Vacuum level (psig) | Average volume of blood sample collected (µL) | Percent of samples having >1 µL of blood collected |
|---|---|---|
| −2.5 | 4.6 | 94 |
| −5.0 | 7.8 | 100 |
| −7.5 | 9.2 | 100 |
| −10.0 | 14.0 | 100 |

The pain results were as follows:

pain of 1=58% pain of 2=31% pain of 3=11%

A nearly linear relationship between level of vacuum and volume of blood collected was observed. The average volume of blood collected with vacuum applied prior and after piercing was approximately twice that collected with vacuum applied only after piercing without vacuum applied prior to piercing. See the results of Example 1 for this comparison (7.8 µL vs. 3.1 µL). The volume of blood collected was always above 1 µL for all levels of vacuum, except −2.5 psig.

Example 3

This example illustrates that localized heating of the area to be pierced followed by vacuum after piercing results in a greater volume of blood being extracted than does extraction with only vacuum after piercing.

Each of four people had his forearm (dorsal forearm, middle of forearm) punctured eight times (at eight different positions on the forearm) with a "BD ULTRA-FINE" lancet in a "MEDISENSE" lancet assembly with heat applied (45° C.) prior to piercing for two different time periods, 15 seconds and 60 seconds A total of 32 runs were carried out, 16 runs where the pre-heating duration was 15 seconds and 16 runs where the pre-heating duration was 60 seconds.

Heat was applied with a heating block, which was an aluminum block having a square face covered with a "KAPTON" film heater element controlled by an "OMEGA" DP41 temperature controller using a T-type thermocouple. Vacuum was applied after each puncturing for 30 seconds at −5.0 psig. Blood was collected into capillary tubes. The amount of blood collected was determined by measuring the length of blood in the tubes. The percentage of collections in which the volume of blood collected exceeded 1.0 µL was calculated. Pain was also tracked. Blood collection results are set forth in TABLE III.

TABLE III

| Pre-piercing heating duration (seconds) | Average volume of blood samples collected (µL) | Percent of samples having >1 µL of blood collected |
|---|---|---|
| 15 | 6.91 | 94 |
| 60 | 11.6 | 100 |

The pain results were as follows:

pain of 1=91% pain of 2=9% pain of 3=0%

The average volume of blood collected using a pre-heating duration of 15 seconds was more than twice the average volume of blood collected at a post-puncturing vacuum level of −5.0 psig., with no pre-heating. See the results of Example 1 for this comparison (6.91 µL vs. 3.1 µL). The average volume of blood collected using a pre-heating duration of 60 seconds was approximately four times the average volume of blood collected at a post-puncturing vacuum level of −5.0 psig, with no pre-heating. See the results of Example 1 for this comparison (11.6 µL vs. 3.1 µL).

Example 4

This example illustrates the effect that stretching the skin upwardly with a vacuum has on the extraction of blood.

Each of four people had his forearm (dorsal forearm, middle of forearm) punctured eight times (at eight different positions on the forearm) with a "BD ULTRA-FINE" lancet in a "MEDISENSE" lancet assembly. Vacuum was applied for a period of 30 seconds prior to puncturing at −5.0 psig using two different vacuum fixtures. The first fixture was a 15 mm diameter vacuum fixture (i. e., a hollow cylindrical tube) used without a net strung across the opening of the tube. The second fixture was a 15 mm diameter vacuum fixture (i. e., a hollow cylindrical tube) used with a net strung across the opening of the tube. The net prevented skin from being raised up into the vacuum fixture. The same vacuum fixture used prior to puncturing was applied for a period of 30 seconds after puncturing. The fixture was held level with the plane of the skin. Four punctures were carried out per person per condition (without net, with net). Accordingly, it can be seen that a total of 32 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE IV.

TABLE IV

| Net across nosepiece | Average volume of blood sample collected (µL) | Percent of samples having >1 µL of blood collected |
|---|---|---|
| No | 5.2 | 87 |
| Yes | 0.6 | 19 |

The pain results were as follows:

pain of 1=94% pain of 2=6% pain of 3=0%

The magnitude of the difference in volume of blood collected and success rates (i. e., percent of samples having >1 µL of blood collected) between the condition of stretching the skin in combination with a vacuum and the condition of not stretching the skin in combination with a vacuum was unexpected. The pain scores were low. This example demonstrates that the combination of skin stretching and applied vacuum significantly increased the volume of blood extracted.

EXAMPLE 5

This example illustrates the effect the area of the extraction site has on the volume of blood collected.

Each of four people had his forearm (dorsal forearm, middle of forearm) punctured at 32 different positions on the forearm with a "BD ULTRA-FINE" lancet in a modified "MEDISENSE" lancet assembly. The "MEDISENSE" lancet assembly had been modified with a more powerful spring and a port had been added.

Vacuum was applied for less than five seconds prior to puncturing. The forearm was punctured under a vacuum of either −5.0 psig or −7.5 psig. The vacuum applied was maintained for 30 seconds after puncturing. The diameter of the pipette tip used to apply vacuum after puncturing was varied, with diameters of 4, 6, 8, and 10 mm being used. Four punctures per condition (diameter, vacuum level) were carried out per person. Accordingly, it can be seen that a total of 128 runs were carried out. Blood was collected into capillary tubes. The amount of blood collected was determined by measuring the length of blood in the tubes. The percentage of collections in which the volume of blood collected exceeded 1.0 µL was calculated. Sensation of pain was also recorded. Blood collection results are set forth in TABLE VA and VB.

TABLE VA

| vacuum level = −5.0 psig | | |
|---|---|---|
| Vacuum diameter (mm) | Average volume of blood sample collected (µL) | Percent of samples having >1 µL of blood collected |
| 4 | 0.3 | 0 |
| 6 | 1.7 | 69 |
| 8 | 3.4 | 94 |
| 10 | 4.1 | 100 |

TABLE VB

| | vacuum level = −7.5 psig | |
| --- | --- | --- |
| Vacuum diameter (mm) | Average volume of blood sample collected (μL) | Percent of samples having >1 μL of blood collected |
| 4 | 0.8 | 25 |
| 6 | 3.1 | 94 |
| 8 | 3.4 | 81 |
| 10 | 6.3 | 94 |

The pain results were as follows:

pain of 1=89% pain of 2=10% pain of 3=1%

The volume of blood collected and success rates (i.e., percent of samples having >1 μL of blood collected) were found to vary directly with the area of skin raised up into the device by the vacuum. A much greater volume of skin was raised up into the larger diameter pipette tip than into the smaller diameter pipette tips.

Example 6

This example illustrates that a plastic multiple point lancet can be used with heat and vacuum to collect a useful amount of blood.

Each of four people had his forearm (dorsal forearm, middle of forearm) punctured sixteen times (at sixteen different positions on the forearm) with a Greer Derma PIK® System for allergy testing (Greer Laboratories, Inc., Lenoir, N.C. 28645) modified to fit into a "MEDISENSE" lancet assembly. Pre-heating was carried out at approximately 40° C. and 45° C. for 15 and 60 seconds prior to puncturing. Four punctures were carried out per condition (temperature, time) per person. Accordingly, it can be seen that a total of 64 runs were carried out.

Heat was applied with a heating block, which comprised an aluminum block having one face covered with a "KAPTON" film heater element controlled by an "OMEGA" DP41 temperature controller using a T-type thermocouple and the opposite face in contact with the larger base of a frustum of a cone made of copper. The larger base of the frustum had a diameter of 0.50 in. The height of the frustum was 0.50 in. The smaller base of the frustum had a diameter of 0.35 in. The smaller base had a cylindrical opening having a diameter of 0.125 in. The cylindrical opening had a common axis with the frustum. The cylindrical opening reduced the heating surface of the copper frustum. Vacuum (−5.0 psig) was applied for a period of 30 seconds after puncturing. The vacuum in contact with the skin was formed by a pipette tip having a diameter of 8 mm. The pipette tip was held level with the plane of the skin. Blood was collected into capillary tubes. The amount of blood collected was determined by measuring the length of blood in the tubes. The percentage of collections in which the volume of blood collected exceeded 1.0 μL was calculated. Sensation of pain was also recorded. Blood collection results are set forth in TABLE VI.

TABLE VI

| Temperature (° C.)/ Time (seconds) | Average volume of blood sample collected (μL) | Percent of samples having >1 (μL) of blood collected |
| --- | --- | --- |
| 40/15 | 2.4 | 31 |
| 40/60 | 2.6 | 50 |
| 45/15 | 2.3 | 56 |
| 45/60 | 5.2 | 81 |

The pain results were as follows:

pain of 1=100% pain of 2=0% pain of 3=0%

This example demonstrates that a blood extraction process employing a multi-point plastic lancet, pre-piercing heating, skin stretching, and post-piercing vacuum can extract at least 1 μL of blood at least 50% of the time.

Example 7

This example demonstrates that the device shown in FIGS. 12A and 12B can be used successfully to obtain blood in quantities sufficient for analysis in an acceptably short amount of time.

The blood collection device shown in FIGS. 12A and 12B was fitted with a "Becton-Dickinson ULTRA-FINE" lancet in the pneumatic lancet assembly disclosed in co-pending application entitled METHOD AND APPARATUS FOR OBTAINING BLOOD FOR DIAGNOSTIC TESTS, Ser. No. 08/982,561. The blood collection device was also fitted with a glucose detector having a 2.0 mm diameter opening covered with mesh, as disclosed in co-pending application entitled METHOD AND APPARATUS FOR OBTAINING BLOOD FOR DIAGNOSTIC TESTS, Ser. No. 08/982,323. Twenty-nine human volunteers were used in this example, with the dorsal forearm of each volunteer subjected to two separate extraction procedures. For each procedure, the blood collection device was placed against the forearm of the volunteer and, after being exposed to a vacuum of approximately −7.5 psig for approximately 5 seconds, each individual had his or her forearm (dorsal forearm) punctured. After the puncture, blood was collected and, when a sufficient amount of blood had been collected, the vacuum was released and the blood collection device was removed from the individual's skin. This process was repeated a total of two times for each individual. Prior to each extraction, a new lancet and glucose detector were fitted into the blood collection device.

Figure 15:
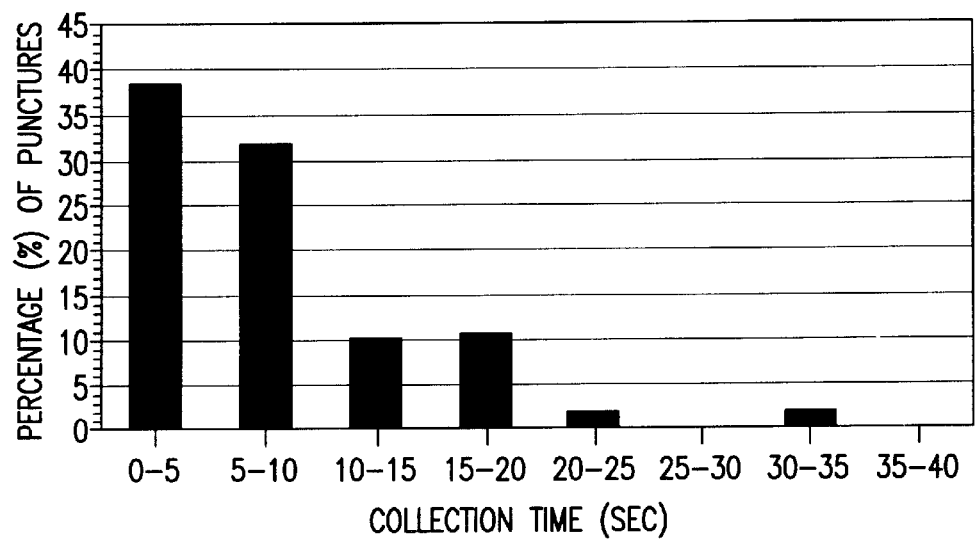
FIG. 15 is a chart indicating blood collection results for an embodiment of the apparatus of this invention.

The time for the glucose detector to collect sufficient blood to perform an analysis was recorded. The glucose detector was considered to have collected sufficient blood when a current of 1.5 μA was generated. Blood collection results are set forth in FIG. 15. The raw data graphically depicted in FIG. 15 is shown for each volunteer in Table VII.

TABLE VII

| Volunteer | Trial 1, Collection Time (sec) | Trial 2, Collection Time (sec) |
| --- | --- | --- |
| 1 | 3.9 | >40 |
| 2 | 13.2 | 14.1 |
| 3 | 1.2 | 2.5 |
| 4 | 34.5 | 9.8 |
| 5 | 0.7 | 8.3 |

TABLE VII-continued

| Volunteer | Trial 1, Collection Time (sec) | Trial 2, Collection Time (sec) |
| --- | --- | --- |
| 6 | 5 | 8 |
| 7 | 0.7 | 2.2 |
| 8 | 7.5 | 3.7 |
| 9 | 3.8 | 3.1 |
| 10 | 17.9 | 3.5 |
| 11 | 18 | 19.3 |
| 12 | 6.7 | 7.9 |
| 13 | 18 | 20.1 |
| 14 | 7.6 | 10.3 |
| 15 | >40 | 2.5 |
| 16 | 12 | >40 |
| 17 | 4.6 | 3.7 |
| 18 | 10.1 | 1.7 |
| 19 | 5 | 6.4 |
| 20 | 6 | 23.9 |
| 21 | 12.7 | 8.8 |
| 22 | 15.7 | 6.9 |
| 23 | 18 | 6.2 |
| 24 | 7.7 | 5.2 |
| 25 | 6 | Malfunction |
| 26 | 13.5 | 5.3 |
| 27 | 4.8 | 6.6 |
| 28 | 3.7 | 2.2 |
| 29 | 1.6 | 2.6 |

The data depicted in FIG. 15 shows that, for over 35% of the punctures, sufficient blood was collected within five seconds to perform an analysis. With the exception of one glucose detector that malfunctioned (volunteer 25, trial 2), for approximately 95% of the punctures, the glucose detectors collected sufficient blood in 40 seconds or less for analysis. For the remaining punctures, the tests were stopped after 40 seconds. With respect to those punctures for which sufficient blood was collected in 40 seconds or less, the average time to collect sufficient blood was 8.2 seconds.

Example 8

This example demonstrates that the device shown in FIGS. 11A through 11C can be successfully used to obtain blood in quantities sufficient for analysis in an acceptably short amount of time.

The blood collection device shown in FIGS. 11A through 11C was fitted with a "BD ULTRA-FINE" lancet in the pneumatic lancet assembly disclosed in co-pending application entitled METHOD AND APPARATUS FOR OBTAINING BLOOD FOR DIAGNOSTIC TESTS, Ser. No. 08/982,561. The blood collection device was also fitted with a glucose detector having a 2.0 mm diameter opening covered with mesh, as disclosed in co-pending application entitled METHOD AND APPARATUS FOR OBTAINING BLOOD FOR DIAGNOSTIC TESTS, Ser. No. 08/982,323. Fifteen human volunteers were used in this example, with the dorsal forearm of each volunteer subjected to four separate extraction procedures. For each procedure, the blood collection device was placed against the forearm of the volunteer and, after being exposed to a vacuum of approximately −7.5 psig for approximately 5 seconds, each individual had his or her forearm (dorsal forearm) punctured. After the puncture, blood was collected and, when a sufficient amount of blood had been collected, the vacuum was released and the blood collection device was removed from the individual's skin. This process was repeated a total of four times for each individual. Prior to each extraction; a new lancet and glucose detector were fitted into the blood collection device.

The time for the glucose detector to collect sufficient blood to perform an analysis was recorded. The glucose detector was considered to have collected sufficient blood when a current of 1.5 µA was generated. Blood collection results are set forth in FIG. 16.

Figure 16:
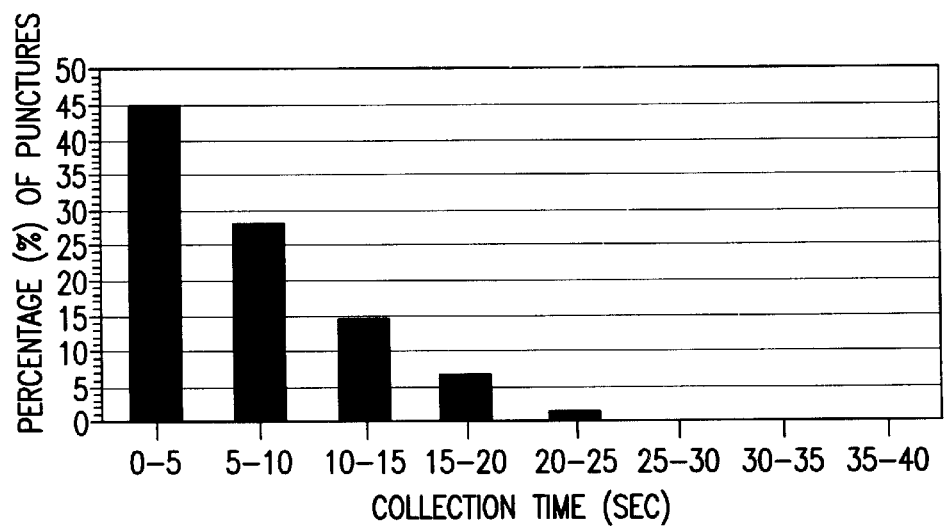
FIG. 16 is a chart indicating blood collection results for an embodiment of the apparatus of this invention.

The data depicted in FIG. 16 shows that, for approximately 45% of the punctures, sufficient blood was collected within five seconds to perform an analysis. For approximately 97% of the punctures, the glucose detectors collected sufficient blood in 40 seconds or less for analysis. For the remaining punctures, the tests were stopped after 40 seconds. With respect to those punctures for which sufficient blood was collected in 40 seconds or less, the average time to collect sufficient blood was 7.0 seconds.

Example 9

This example demonstrates that the device shown in FIGS. 13A through 13E can be successfully used to obtain blood in quantities sufficient for analysis in an acceptably short amount of time.

The blood collection device shown in FIGS. 13A through 13E was fitted with a "BD ULTRA-FINE" lancet in the pneumatic lancet assembly disclosed in co-pending application entitled METHOD AND APPARATUS FOR OBTAINING BLOOD FOR DIAGNOSTIC TESTS, Ser. No. 08/982,561. The blood collection device was also fitted with a glucose detector having a 2.0 mm diameter semicircular notch covered with mesh at one end of the detector, as disclosed in co-pending application entitled METHOD AND APPARATUS FOR OBTAINING BLOOD FOR DIAGNOSTIC TESTS, Ser. No. 08/982,323. Twenty-nine human volunteers were used in this example, with the dorsal forearm of each volunteer subjected to two separate extraction procedures. For each procedure, the blood collection device was placed against the forearm of the volunteer and, after being exposed to a vacuum of approximately −7.5 psig for approximately 5 seconds, each individual had his or her forearm (dorsal forearm) punctured. Fifty milliseconds after the lancet was triggered, the movable projection was triggered and the glucose detector was moved nearer the lanced opening in the individual's skin. After the puncture, blood was collected and, when a sufficient amount of blood had been collected, the vacuum was released and the blood collection device was removed from the individual's skin. This process was repeated a total of two times for each individual. Prior to each extraction, a new lancet and glucose detector were fitted into the blood collection device.

The time for the glucose detector to collect sufficient blood to perform an analysis was recorded. The glucose detector was considered to have collected sufficient blood when a current of 1.5 µA was generated. Blood collection results are set forth in FIG. 17.

Figure 17:
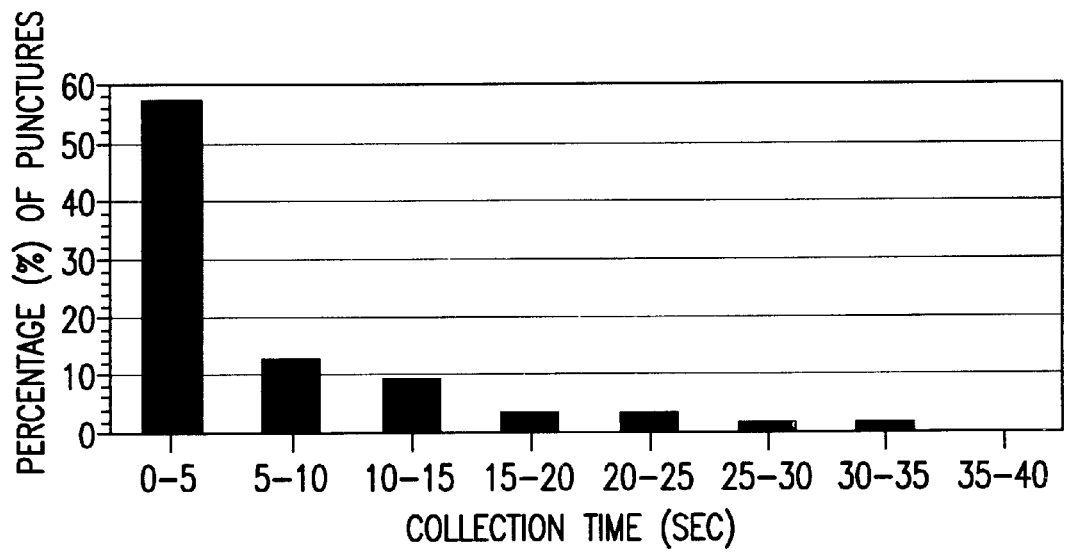
FIG. 17 is a chart indicating blood collection results for an embodiment of the apparatus of this invention.

The data depicted in FIG. 17 shows that for over 55% of the punctures, sufficient blood was collected within 5 seconds to perform an analysis. Two of the glucose detectors did not exceed the trigger current of 1.5 µA due to hardware or software problems. Two of the glucose detectors did not move due to an unknown problem and did not contact the skin. Excluding these four punctures, for 91% of the remaining punctures, the glucose detectors collected sufficient blood in 40 seconds or less for analysis. For the remaining punctures, the tests were stopped after 40 seconds. With respect to those punctures for which sufficient blood was collected in 40 seconds or less, the average time to collect sufficient blood was 6.8 seconds.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. An apparatus suitable for obtaining a sample of blood for analysis in a diagnostic test, comprising:
   (a) a housing having a sealable chamber located therein and a sealable opening in fluid communication with said sealable chamber,
   (b) a power source positioned in said housing,
   (c) a vacuum pump positioned in said housing, said vacuum pump operably connected to said power source, said vacuum pump in communication with said sealable chamber,
   (d) a lancing assembly positioned in said housing, said lancing assembly both capable of moving a lancet towards said sealable opening at a sufficient speed to form an opening in said skin and capable of moving said lancet away from said sealable opening, whereby said lancet forms an unobstructed opening in skin when said skin is adjacent said sealable opening, and
   (e) electronics in said housing for controlling power for said pump, whereby said electronics controls said pump to maintain a vacuum at a specified level.

2. The apparatus of claim 1, wherein said housing comprises:
   (a) a body portion
   (b) a door portion, said door portion positionable over said body portion and including said sealable opening.

3. The apparatus of claim 2, wherein a fluid collector is positioned in a slot in said door portion.

4. The apparatus of claim 3, wherein said slot locates said fluid collector adjacent said sealable opening when said door portion is positioned over said body portion.

5. The apparatus of claim 2, wherein said body portion contains at least one slot for inserting a fluid collector.

6. The apparatus of claim 2, wherein said body portion includes at least one electrical connection.

7. The apparatus of claim 2, wherein said door portion includes at least one electrical connection.

8. The apparatus of claim 2, wherein said body portion comprises a movable projection containing a slot, and a fluid collector is capable of being positioned in said slot.

9. The apparatus of claim 8, wherein said movable projection includes at least one electrical connection.

10. The apparatus of claim 1, wherein said housing comprises:
    (a) a body portion,
    (b) an interior cover portion positionable over said lancing assembly, and
    (c) a door portion positionable over said interior cover portion and including said sealable opening.

11. The apparatus of claim 10, wherein said interior cover portion contains at least one alignment channel to position a fluid collector.

12. The apparatus of claim 10, wherein said door portion contains at least one alignment fixture to position a fluid collector.

13. The apparatus of claim 10, wherein said housing further comprises a projection.

14. The apparatus of claim 13, wherein a fluid collector is positioned in at least one slot in said projection.

15. The apparatus of claim 14, wherein said at least one slot is parallel to the upper surface of said interior cover.

16. The apparatus of claim 14, wherein said at least one slot is not parallel to the upper surface of said interior cover.

17. The apparatus of claim 14, wherein said projection includes at least one electrical connection.

18. The apparatus of claim 1, further comprising a heating element.

19. The apparatus of claim 1, further comprising a reflectometer.

20. The apparatus of claim 1, further comprising a display operably connected to said power source and a fluid collector.

21. The apparatus of claim 1, further comprising a switch operably connected to said vacuum pump and said lancing assembly though said power source.

22. The apparatus of claim 1, wherein the electronics control power to a heating element.

23. The apparatus of claim 1, wherein the electronics control power to the lancing assembly.

24. The apparatus of claim 1, further including a fluid collector positioned in said sealable chamber, said fluid collector in fluid communication with said sealable opening.

25. The apparatus of claim 24, wherein said fluid collector comprises a biosensor.

26. The apparatus of claim 25, wherein said biosensor comprises a glucose detector.

27. The apparatus of claim 24, wherein said fluid collector comprises a reflectance strip.

28. The apparatus of claim 27, wherein said reflectance strip comprises a glucose detector.

29. The apparatus of claim 24, further comprising more than one of said fluid collector.

* * * * *